US009066940B2

(12) United States Patent
Leoni et al.

(10) Patent No.: US 9,066,940 B2
(45) Date of Patent: Jun. 30, 2015

(54) PHARMACEUTICAL COMPOSITIONS COMPRISING IMIDAZOQUINOLIN(AMINES) AND DERIVATIVES THEREOF SUITABLE FOR LOCAL ADMINISTRATION

(75) Inventors: Lorenzo Leoni, Lodrino (CH); Roberto Maj, Saronno (IT); Franco Pattarino, Turin (IT); Carlo Vecchio, Veruno (IT)

(73) Assignee: TELORMEDIX, SA, Bioggio (CH)

( * ) Notice: Subject to any disclaimer, the term of this patent is extended or adjusted under 35 U.S.C. 154(b) by 47 days.

(21) Appl. No.: 13/147,194

(22) PCT Filed: Feb. 5, 2010

(86) PCT No.: PCT/EP2010/000722
§ 371 (c)(1),
(2), (4) Date: Sep. 14, 2011

(87) PCT Pub. No.: WO2010/089128
PCT Pub. Date: Aug. 12, 2010

(65) Prior Publication Data
US 2011/0319442 A1  Dec. 29, 2011

(30) Foreign Application Priority Data
Feb. 6, 2009 (WO) ................ PCT/EP2009/000834

(51) Int. Cl.
A61K 31/4164 (2006.01)
A61K 31/437 (2006.01)
A61K 47/40 (2006.01)
A61K 47/10 (2006.01)
A61K 31/4745 (2006.01)
A61K 9/00 (2006.01)
A61K 47/12 (2006.01)
A61K 47/34 (2006.01)

(52) U.S. Cl.
CPC ........... *A61K 31/4745* (2013.01); *A61K 9/0034* (2013.01); *A61K 47/10* (2013.01); *A61K 47/12* (2013.01); *A61K 47/40* (2013.01); *A61K 9/0014* (2013.01); *A61K 47/34* (2013.01)

(58) Field of Classification Search
USPC .......................................... 514/267, 269, 293
See application file for complete search history.

(56) References Cited

U.S. PATENT DOCUMENTS

| 4,689,338 | A | 8/1987 | Gerster et al. |
|---|---|---|---|
| 4,727,064 | A | 2/1988 | Pitha |
| 4,929,624 | A | 5/1990 | Gerster et al. |
| 4,938,949 | A | 7/1990 | Borch et al. |
| 5,037,986 | A | 8/1991 | Gerster |
| 5,175,296 | A | 12/1992 | Gerster |
| 5,238,944 | A | 8/1993 | Wick et al. |
| 5,352,784 | A | 10/1994 | Nikolaides et al. |
| 5,367,076 | A | 11/1994 | Gerster |
| 5,395,937 | A | 3/1995 | Nikolaides et al. |
| 5,444,065 | A | 8/1995 | Nikolaides et al. |
| 5,624,677 | A | 4/1997 | El-Rashidy et al. |
| 5,627,281 | A | 5/1997 | Nikolaides et al. |
| 5,648,516 | A | 7/1997 | Nikolaides et al. |
| 5,693,811 | A | 12/1997 | Lindstrom |
| 5,736,553 | A | 4/1998 | Wick et al. |
| 5,741,908 | A | 4/1998 | Gerster et al. |
| 5,998,619 | A | 12/1999 | Gerster et al. |
| 6,038,505 | A | 3/2000 | Probst et al. |
| 6,039,969 | A | 3/2000 | Tomai et al. |
| 6,083,505 | A | 7/2000 | Miller et al. |
| 6,150,523 | A | 11/2000 | Gerster et al. |
| 6,200,592 | B1 | 3/2001 | Tomai et al. |
| 6,245,776 | B1 | 6/2001 | Skwiercynski et al. |
| 6,329,381 | B1 | 12/2001 | Kurimoto et al. |
| 6,333,331 | B1 | 12/2001 | Moschel et al. |
| 6,407,079 | B1 | 6/2002 | Muller et al. |
| 6,437,131 | B1 | 8/2002 | Gerster et al. |
| 6,486,168 | B1 | 11/2002 | Skwierczynski et al. |
| 6,534,654 | B2 | 3/2003 | Gerster et al. |
| 6,552,192 | B1 | 4/2003 | Hanus et al. |
| 6,610,319 | B2 | 8/2003 | Tomai et al. |
| 6,613,902 | B2 | 9/2003 | Gerster et al. |
| 6,624,305 | B2 | 9/2003 | Gerster |
| 6,696,076 | B2 | 2/2004 | Tomai et al. |
| 6,706,728 | B2 | 3/2004 | Hedenstrom et al. |

(Continued)

FOREIGN PATENT DOCUMENTS

| CN | 101129373 | 2/2008 |
|---|---|---|
| CN | 101230064 | 7/2008 |

(Continued)

OTHER PUBLICATIONS

Dumortier et al. "A Review of Poloxamer 407 Pharmaceutical and Pharmacological Characteristics". Pharmaceutical Research, vol. 23, No. 12, Dec. 2006.*
Database WPI, Section Ch, Week 200870, Thomson Scientific, London, GB, Feb. 27, 2008.
Smith et al., "Antitumor Effects of Imidazoquinolines in Urothelial Cell Carcinoma of the Bladder," the Journal of Urology, vol. 177, pp. 2347-2351, Jun. 2007.
Julien, R.M., Chapter 2: Pharmacodynamics: How Drugs Act, A Primer of Drug Action, (Ninth Edition); Worth Publishers, (2001), pp. 37-57.
Lippard et al., "Chemical Synthesis: The art of chemistry," Nature, 416, (2002), p. 587.
"I. Pharmaceutical Importance of Crystallin Hydrates", [online]. [retrieved on May 30, 2008]. Retrieved from the Internet: <URL: http://www.netlibrary.com/nlreader.dll?bookid=12783 &filename=Page_ 126. html>, (2008), 126-127.

(Continued)

Primary Examiner — Renee Claytor
(74) Attorney, Agent, or Firm — Grant IP, Inc.

(57) ABSTRACT

The present invention relates in general to the field of modulators of the innate immune system, particularly to pharmaceutical compositions comprising imidazoquinolin(amines) and derivatives thereof, preferably suitable for local administration, such as, intravesical administration. In addition, the present invention concerns the use of imidazoquinolin (amines) and derivatives thereof for intravesical treatment of bladder diseases, such as, for example, bladder cancer and cystitis. The present invention furthermore comprises methods of treatment for these diseases as well as methods of administration of the inventive pharmaceutical compositions.

13 Claims, 26 Drawing Sheets

(56) References Cited

U.S. PATENT DOCUMENTS

| | | | |
|---|---|---|---|
| 6,716,840 B2 | 4/2004 | Chu et al. | |
| 6,733,764 B2 | 5/2004 | Martin | |
| 6,734,187 B1 | 5/2004 | Tanaka et al. | |
| 6,897,314 B2 | 5/2005 | Gerster et al. | |
| 6,960,582 B2 | 11/2005 | Boyce et al. | |
| 7,001,609 B1 | 2/2006 | Matson et al. | |
| 7,157,465 B2 | 1/2007 | Isobe et al. | |
| 7,189,727 B2 | 3/2007 | Boyce | |
| 7,241,890 B2 | 7/2007 | Kasibhatla et al. | |
| 7,521,454 B2 | 4/2009 | Isobe et al. | |
| 7,655,672 B2 * | 2/2010 | Statham et al. | 514/290 |
| 2002/0127224 A1 | 9/2002 | Chen | |
| 2002/0193595 A1 | 12/2002 | Chu et al. | |
| 2003/0187261 A1 | 10/2003 | Havlicek et al. | |
| 2003/0191086 A1 | 10/2003 | Hanus et al. | |
| 2004/0023211 A1 | 2/2004 | Groen et al. | |
| 2004/0132748 A1 | 7/2004 | Isobe et al. | |
| 2004/0202663 A1 | 10/2004 | Hu et al. | |
| 2004/0248895 A1 | 12/2004 | Chu et al. | |
| 2004/0265351 A1 | 12/2004 | Miller et al. | |
| 2005/0004144 A1 | 1/2005 | Carson et al. | |
| 2005/0038027 A1 | 2/2005 | Boyce | |
| 2005/0049263 A1 | 3/2005 | Kasibhatla et al. | |
| 2005/0054590 A1 | 3/2005 | Averett | |
| 2005/0059613 A1 | 3/2005 | Memarzadeh et al. | |
| 2005/0266067 A1 | 12/2005 | Sengupta et al. | |
| 2006/0052403 A1 | 3/2006 | Isobe et al. | |
| 2006/0110746 A1 | 5/2006 | Andre et al. | |
| 2007/0037832 A1 | 2/2007 | Isobe et al. | |
| 2007/0087009 A1 | 4/2007 | Burdin | |
| 2007/0100146 A1 | 5/2007 | Dzwiniel | |
| 2007/0161582 A1 | 7/2007 | Mijikovic et al. | |
| 2007/0173483 A1 | 7/2007 | Kasibhatla et al. | |
| 2007/0264317 A1 * | 11/2007 | Yosha et al. | 424/448 |
| 2007/0292418 A1 | 12/2007 | Fields et al. | |
| 2008/0008682 A1 | 1/2008 | Chong et al. | |
| 2008/0125446 A1 | 5/2008 | Kasibhatla et al. | |
| 2008/0207674 A1 | 8/2008 | Stoesz et al. | |
| 2008/0214580 A1 | 9/2008 | Neagu et al. | |
| 2009/0047249 A1 | 2/2009 | Graupe et al. | |
| 2009/0053186 A1 | 2/2009 | Hu et al. | |
| 2009/0069289 A1 | 3/2009 | Neagu et al. | |
| 2009/0105212 A1 | 4/2009 | Isobe et al. | |
| 2009/0118263 A1 | 5/2009 | Hashimoto et al. | |
| 2009/0131458 A1 | 5/2009 | Lazarides et al. | |
| 2009/0182004 A1 * | 7/2009 | Winckle et al. | 514/293 |
| 2009/0202484 A1 | 8/2009 | Chong et al. | |
| 2009/0202626 A1 | 8/2009 | Carson et al. | |
| 2009/0263470 A1 | 10/2009 | Coller et al. | |
| 2009/0324551 A1 | 12/2009 | Carson et al. | |
| 2011/0098294 A1 | 4/2011 | Carson et al. | |
| 2013/0237561 A1 | 9/2013 | Leoni et al. | |

FOREIGN PATENT DOCUMENTS

| | | |
|---|---|---|
| CN | 101239980 | 8/2008 |
| EP | 0145340 | 6/1985 |
| EP | 0310950 | 4/1989 |
| EP | 0389302 | 9/1990 |
| EP | 0394026 A1 | 10/1990 |
| EP | 0553202 | 8/1993 |
| EP | 0575549 | 12/1993 |
| EP | 0636031 | 2/1995 |
| EP | 0681570 | 11/1995 |
| EP | 0708773 | 5/1996 |
| EP | 0912564 | 5/1999 |
| EP | 0912565 | 5/1999 |
| EP | 0938315 | 9/1999 |
| EP | 1035123 | 9/2000 |
| EP | 1550662 | 7/2005 |
| EP | 1182208 | 7/2007 |
| EP | 1939202 | 7/2008 |
| EP | 2259788 | 2/2010 |
| EP | 2259788 | 12/2010 |
| JP | 11193282 | 7/1999 |
| JP | 2000159767 | 6/2000 |
| JP | 2001213867 | 8/2001 |
| JP | 2004137157 | 5/2004 |
| JP | 2005089334 | 4/2005 |
| JP | 2006/519784 | 8/2006 |
| WO | WO 85/02767 | 7/1985 |
| WO | WO 92/15581 | 9/1992 |
| WO | WO 93/20847 | 10/1993 |
| WO | WO 98/17279 | 4/1998 |
| WO | WO 98/48805 | 11/1998 |
| WO | WO 99/24432 | 5/1999 |
| WO | WO 99/28321 | 6/1999 |
| WO | WO 00/40228 | 7/2000 |
| WO | WO 00/43394 | 7/2000 |
| WO | WO 01/19320 | 3/2001 |
| WO | WO 01/49688 | 7/2001 |
| WO | WO 02/24225 | 3/2002 |
| WO | WO 02/081443 | 10/2002 |
| WO | WO 02/085905 | 10/2002 |
| WO | WO 03/037860 | 5/2003 |
| WO | WO 03/077944 | 9/2003 |
| WO | WO 2004/029054 | 4/2004 |
| WO | WO 2004/032829 | 4/2004 |
| WO | WO 2004/066947 | 8/2004 |
| WO | WO 2005/011708 | 2/2005 |
| WO | WO 2005/020892 | 3/2005 |
| WO | WO 2005/025583 | 3/2005 |
| WO | WO 2005/060966 | 7/2005 |
| WO | WO 2005/092892 | 10/2005 |
| WO | WO 2006/087538 | 8/2006 |
| WO | WO 2006/100226 | 9/2006 |
| WO | WO 2006/117670 | 11/2006 |
| WO | WO 2007/015877 | 2/2007 |
| WO | WO 2007/024707 | 3/2007 |
| WO | WO 2007/034817 | 3/2007 |
| WO | WO 2007/034881 | 3/2007 |
| WO | WO 2007/034882 | 3/2007 |
| WO | WO 2007/034917 | 3/2007 |
| WO | WO 2007/038720 | 4/2007 |
| WO | WO 2007/041863 | 4/2007 |
| WO | WO 2007/142755 | 12/2007 |
| WO | WO 2008/005555 | 1/2008 |
| WO | WO 2008/043031 | 4/2008 |
| WO | WO 2008/045529 | 4/2008 |
| WO | WO 2008/101867 | 8/2008 |
| WO | WO 2008/114008 | 9/2008 |
| WO | WO 2008/114817 | 9/2008 |
| WO | WO 2008/115319 | 9/2008 |
| WO | 2008/118763 A1 | 10/2008 |
| WO | WO 2009/005687 | 1/2009 |
| WO | WO 2009/034386 | 3/2009 |
| WO | WO 2009/035634 | 3/2009 |
| WO | WO 2009/091541 | 7/2009 |
| WO | 2009/099650 A2 | 8/2009 |
| WO | WO 2009/099650 | 8/2009 |
| WO | WO 2009/143457 | 11/2009 |
| WO | WO 2010/089128 | 8/2010 |
| WO | WO 2010/093436 | 8/2010 |
| WO | WO 2011/017611 | 2/2011 |
| WO | WO 2011/139348 | 11/2011 |

OTHER PUBLICATIONS

Akazawa et al., "Adjuvant-mediated tumor regression and tumor-specific cytotoxic response are impaired in MyD88-deficient mice." Cancer research. 2004; 64: 757-764.

Alexandroff et al., "BCG immunotherapy of bladder cancer: 20 years on" Lancet 1999; 353: 1689-1694.

Anderson et al., "Understanding drug release from poly(ethylene oxide)-b-poly(propylene oxide)-b-poly(ethylene oxide) gels,"J Control Release. 2001; 70: 157-167.

Arentsen et al., "Pharmacokinetics and Toxicity of Intravesical TMX-101: A Preclinical Study in Pigs," The Journal of Urology, e380, vol. 183, No. 4, Supplement, Monday 31, 2010.

Atkins et al., "Polarisation of a T-helper cell immune response by activation of dendritic cells with CpGcontaining oligonucleotides: a potential therapeutic regime for bladder cancer immunotherapy." British journal of cancer. 2003; 89: 2312-2319.

(56) References Cited

OTHER PUBLICATIONS

Babjuk et al; European Association of Urology (EAU). EAU guidelines on non-muscle-invasive urothelial carcinoma of the bladder. Eur Urol 2008;54:303-314.

Baenziger et al., "Triggering TLR7 in mice induces immune activation and lymphoid system disruption, resembling HIV-mediated pathology", Blood, 113(2), (Jan. 8, 2009), 377-388.

Barnetson RS, Satchel A, Zhuang L, Slade HB, Halliday GM. Imiquimod induced regression of clinically diagnosed superficial basal cell carcinoma is associated with early infiltration by CD4 T cells and dendritic cells. Clinical and experimental dermatology,2004; 29: 639-43).

Bilensoy et al., "Mucoadhesive, thermosensitive, prolonged-release vaginal gel for clotrimazole:beta-cyclodextrin complex," AAPS PharmSciTech. 2006; June 7(2) E54-E60.

Bohle A, Brandau S. Immune mechanisms in bacillus Calmette-Guerin immunotherapy for superficial bladder cancer. The Journal of urology. 2003; 170: 964-969.

Brewster et al., "Cyclodextrins as pharmaceutical solubilizers." Advanced drug delivery reviews. 2007; 59: 645-666.

Bryan et al., "Interferon (IFN) and IFN Inducers Protect Mouse Bladder Urothelium Against Carcinogenicity by FANFT", Journal of Cancer Research and Clinical Oncolog~, 116(Suppl. Part 1), (Abstract A3.1 06.36), (15th International Cancer Congress, Hamburg, Aug. 16-22, 1990), (1990), p. 308.

Cabana et al, Study of the Gelation Process of Polyethylene Oxide-polypropylene Oxide-Polyethylene Oxide Copolymer (Poloxamer 407) Aqueous Solutions, J. Colloid Interface Sci. 190, 307-312 (1997).

De Boer et al., "Cytokine gene expression in a mouse model: the first instillations with viable bacillus Calmette-Guerin determine the succeeding Th1 response." The Journal of urology. 2003; 170: 2004-2008.

Carson, D. A., et al., "TLR Agonists", U.S. Appl. No. 60/710,337, filed Aug. 22, 2005, 52 pgs.

Chan et al., "Synthesis and immunological characterization of toll-like receptor 7 agonistic conjugates," Bioconjug Chem. Jun. 2009;20(6):1194-1200.

Chang et al., "Prolonged antifungal effects of clotrimazole containing mucoadhesive thermosensitive gels on vaginitis." J Control Release. 2002; 82: 39-50.

Chang Yuchi C et al., Current and potential uses of imiquimod, Southern Medical journal, Southern Medical Association, US, vol. 98, No. 9, Sep. 2005, pp. 913-919.

Chollet et al., "Development of a Topically Active Imiquimod Formulation," Pharmaceutical Development and Technology, 4(1), 35-43, 1999.

Clarke et al., "Comparison of Rat and Human Response to Toll-like Receptor 7 Activation," Journal of Interferon & Cytokine Research (2009), 29(2), 113-126.

Colombo et. al., "Combination of intravesical chemotherapy and hyperthermia for the treatment of superficial bladder cancer: preliminary clinical experience.," Critical Reviews in Oncology/Hematology, 2003, Elsevier, vol. 47, pp. 127-139.

De Jager et al. Long-term complete remission in bladder carcinoma in situ with intravesical TICE bacillus Calmette Guerin. Overview analysis of six phase II clinical trials. Urology. 1991; 38: 507-13.

Dharmapuri et al., "An oral TLR7 agonist is a potent adjuvant of DNA vaccination in transgenic mouse tumor models," Cancer Gene Therapy, (2009) 16(5), 462-472.

Dolan et al., "Metabolism of 06-benzylguanine, an inactivator of 06-alkylguanine-DNA alkyltransferase.", Cancer Res., 54(19), (Oct. 1, 1994),5123-30.

Games J. Nursing implications in the management of superficial bladder cancer. Seminars in urologic oncology.: 1996; 14: 36-40.

Geisse J, Caro I, Lindholm 1, Golitz L, Stampone P, Owens M. Imiquimod 5% cream for the treatment of superficial basal cell carcinoma: Results from two phase III, randomized, vehicle-controlled studies. J Am Acad Dermatol 2004;50:722-733.

Geng et al., "Exploring 9-benzyl purines as inhibitors of glutamate racemase (Murl) in Gram-positive bacteria," Bioorganic & Medicinal Chemistry Letters (2008), 18(15), 4368-4372.

Hasan et al., "Human TLR10 is a functional receptor, expressed by B cells and plasmacytoid dendritic cells, which activates gene transcription through MyD88," The Journal of Immunology, 2005, 174: 2942-2950.

Hayashi et al. Mast cell-dependent anorexia and hypothermia induced by mucosal activation of Toll-like receptor 7. Am J Physiol Regullntegr Comp Physio/. 2008; 295: R123-32).

Hayashi et al., "Prevention of autoimmune disease by induction of tolerance to Toll-like receptor 7," PNAS USA (2009), 106(8), 2764-2769.

Hegele et al., "Antineoplastic effect of immunostimulatory DNA (CpG-ODN) in a murine C57-BL6/MB-49 transitional cell carcinoma model." Anticancer research. 2004; 24: 2225-30.

Hengge U et al., Topical immunomodulators—progress towards treating inflammation, infaction, and cancer, Lancet Infectious Diseases, Elsevier Ltd., US, vol. 1, No. 3, Oct. 2001, pp. 189-198.

Jin, G., et al., "Synthesis and immunostimulatory activity of 8-substituted amino 9-benzyladenines as potent Toll-like receptor 7 agonists.", Bioorg Med Chem Lett., 16(17), (Sep. 1, 2006), 4559-63.

Kawai, T. and S. Akira (2006). "TLR signalling." Cell Death Differ 13(5): 816-825.

Kobayashi et al., "Prepriming: a novel approach to DNA-based vaccination and immunomodulation", Springer Seminars in Immunopathology, 22(Nos. 1-2), (2000), 8.

Kulikov et. al., Pharmaceutical Chemistry Journal, 1997, Springer, vol. 31, No. 4, pp. 173-177.

Kurimoto et al., "Synthesis and structure-activity relationships of 2-amino-8-hydroxyadenines as orally active interferon inducing agents", Bioorg Med Chem., 11(24), (Dec. 1, 2003),5501-8.

Lee et al., "Molecular basis for the immunostimulatory activity of guanine nucleoside analogs: Activation of Toll-like receptor 7", Proc. Natl. Acad. Sci., 100(11), (2003), 6646-6651.

Liu et al., "Tumour growth inhibition by an imidazoquinoline is associated with c-Myc down-regulation in urothelial cell carcinoma." BJU Int 2008; 101 :894-901.

Luo et al., "Role of Th1 and Th2 cytokines in BCG-induced IFN-gamma production: cytokine promotion and simulation of BCG effect," Cytokine. 2003; 21: 17-26.

Malmstrom et al., "An individual patient data meta-analysis of the long-term outcome of randomized studies comparing intravesical Mitomycin C versus Bacillus Caimettte-Guerin for non-muscleinvasive bladder cancer," Eur Urol 2009; 56 (2):247-256.

Mangsbo et al., "CpG therapy is superior to BCG in an orthotopic bladder cancer model and generates CD4+ T-ell immunity." J Immunother. 2008; 31: 34-42.

Mayer et al., "A randomized controlled trial of intravesical bacillus calmette-guerin for treatment refractory interstitial cystitis", Journal of Uroloav. 173, (2005), 1186-1191.

Metzler, David E, "Biosynthesis of triglycerides and phospholipids", Biochemistry: The Chemical Reactions of Living Cells, (1977), 3 pgs.

Miller, R L, et al., "Imiquimod applied topically: a novel immune response modifier and new class of drug", IntJ Immunopharmacol., 21(1), (Jan. 1999),1-14.

Mosmann, T. R., et al., "TH1 and TH2 cells: different patterns of lymphokine secretion lead to different functional properties", Annual Review Immunology, 7, (1989), 145-173.

Musmuca et al., "Small-Molecule Interferon Inducers. Toward the Comprehension of the Molecular Determinants through Ligand-Based Approaches," J Chem Inf Model (2009), 49(7) 1777-1786.

Purdon CH, Azzi CG, Zhang J, Smith EW, Maibach HI. Penetration enhancement of transdermal delivery-current permutations and limitations. Crit Rev Ther Drug Carrier Syst 2004; 21: 97-132.

Rohn et. al., J. Agric. Food Chem., 2004, American Chemical Society, vol. 52, pp. 4725-4729.

Saban et al., "Discriminators of mouse bladder response to intravesical Bacillus Calmette-Guerin (BCG)," BMC immunology. 2007; 8: 6.

Schenk-Braat EA, Bangma CH. Immunotherapy for \superficial bladder cancer. Cancer ImmunolImmunother. 2005; 54: 414-23.

(56) References Cited

OTHER PUBLICATIONS

Schoen, Magarete, et al., "Tumor-Selective Induction of Apoptosis and the Small-Molecule Immune Response Modifier Imiquimod", J Natl Cancer Inst, 95(15), (2003), 1138-1149.

Schon MP, Schon M. Zhang (J. Control. Release, 85 (2002) 73-81)Imiquimod: mode of action. Br J Dermatol2007;157:8-13.

Sidky. Y. A. et al.. "Curative effectiveness of the interferon inducing imiquimod as a signal agent in mouse bladder tumors". (Abstract 2789). Proceedings, Eighty-Fourth Meeting of the American Association for Cancer Research, vol. 34. (May 19-22, 1993. Orlando. FL), (Mar. 1993). p. 467.

Sidky, Y. A, et al., "Inhibition of Murine Tumor Growth by an Interferon-Inducing Imidazoquinolinamine". Cancer Research, 52. (1992). 3528-3533.

Sidky. Y. A. et al.. "Effects of Treatment with an Oral Interferon Inducer. Imidazoquinolinamine (R-837). on the Growth of Mouse Bladder Carcinoma FCB". (Abstract 116-12). Journal of Interferon Research, vol. 10, SUI2I2Iement 1. (Annual Meeting of the ISIR. San Francisco, CA. Nov. 14-18, 1990). (Nov. 1990). p. S123.

Sidky. Y. A. et al.. "Effects of treatment with the oral interferon inducer. R-837. on the growth of mouse colon carcinoma. MC-26". (Abstract 2574). Proceedings, 81st Annual Meeting of the American Association for Cancer Research, vol. 31, (Mar. 1990), p. 433.

Sidky. Y. A. et al.. "Inhibition of tumor-induced angiogenesis by the interferon inducer Imiquimod".(Abstract 458) Proceedings, Eighty-Third Annual Meeting of the American Association of Cancer Research, vol. 33. (May 20-23, 1992. San Diego, CA). (Mar. 1992), p. 77.

Simons MP, O'Donnell MA, Griffith TS. Role of neutrophils in BCG immunotherapy for bladder cancer. Urologic oncology. 2008; 26: 341-345.

Simons. M. P .. et al., "Identification of the Mycobacterial Subcomponents Involved in the Release of Tumor Necrosis Factor-Related Apoptosis-Inducing Ligand from Human Neutrophils". (Abstract 458). Infection and Immunity 75(3). (2007). 1265-1271.

Smith et al., Antitumor effects of imidazoquinolines in urothelial cell carcinoma of the bladder, J Urol. Jun. 2007;177(6):2347-2351.

Smith et al., "Effects of imiquimod, a toll-like receptor-7 agonist on cell proliferation and cytokine production in bladder cancer in vitro and in vivo," Journal of Urology, vol. 173, No. 4, Suppl. S, Apr. 2005, p. 158 & Annual Meeting of the American-Urological-Association, San Antonio, TX, USA; May 21-26, 2005.

Suttmann H, Riemensberger J, Bentien G et al. Neutrophil granulocytes are required for effective Bacillus Calmette-Guerin immunotherapy of bladder cancer and orchestrate local immune responses. Cancer research. 2006; 66: 8250-7.

Sylvester FJ, Van der Meijden AP, Lamm DL. intravesical bacillus Calmetie-Guerin reduces the risk of progression in patients with superficial bladder cancer: a metaanalysis of the published results of randomized clinical trials. J Urol 2002; 168:196470.

Totterman TH, Loskog A, Essand M. The immunotherapy of prostate and bladder cancer. BJU international 2005; 96: 728-735.

Veronese, F. M., et al., "The impact of PEGylation on biological therapies", SioDrugs, 22(5), (2008), 315-329.

Vultaggio et al., "Modified Adenine (9-Benzyl-2-Butoxy-8-Hydroxyadenine) Redirects Th2-Mediated Murine Lung Inflammation by Triggering TLD7," Journal of Immunology (2009), 182(2), 880-889.

Wagstaff AJ, Perry CM. Topical imiquimod: a review of its use in the management of anogenital warts, actinic keratoses, basal cell carcinoma and other skin lesions. Drugs. 2007; 67: 2187-210.

Weterings et al., "2-Azidoalkoxy-7-hydro-8-oxoadenine derivatives as TLR7 agonists inducing dendritic cell maturation," Bioorganic & Medicinal Chemistry Letters (2009), 19(8), 2249-2251.

Wille-Reece, U .. et al.. HIV Gag protein conjugated to a Toll-like receptor 7/8 agonist improves the magnitude and quality of Th1 and CD8+ T cell responses in nonhuman primates . . . Proc. Natl. Acad. Sci. USA, 102(42}, (Oct. 18, 2005).15190-15194.

Witjes JA, Palou J, Soloway M, Lamm 0, Brausi M, Spermon JR, Persad R, Buckley R, Akaza H, Colombel M, Bohle A. Clinical Practice recommendations for the prevention and management of intravesical therapy-associated adverse events. Eur. Urol Suppl2008;7:667-674.

Witt PL, Ritch PS, Reding, McAuliffe TL, Westrick L, Grossberg SE, Borden EC. Phase I trial of an oral immunomodulator and interferon inducer in cancer patients. Cancer Res 1993;53:5176-5180.

Wu et al., "Immunotherapeudic activity of a conjugate of a Toll-like receptor 7 Ligand," PNAS USA (2007), 104(10), 3990-3995.

Zaks. K. et al.. "Efficient immunization and cross-priming by vaccine adjuvants containing TLR3 or TLR9 agoinst complexed to cationic Liposomes". Journal of Immunology, 176 (12). (Jun. 15, 2006). 7335-7345.

Zhang (J. Control. Release, 85 (2002) 73-81).

Office Action dated: Apr. 13, 2012 in U.S. Appl. No. 12/367,172, filed Feb. 6, 2009 and published as: US2009/02022626 on Aug. 13, 2009.

Office Action dated: Jan. 18, 2012 in U.S. Appl. No. 12/367,172, filed Feb. 6, 2009 and published as: US2009/02022626 on Aug. 13, 2009.

Office Action dated: May 27, 2011 in U.S. Appl. No. 12/367,172, filed Feb. 6, 2009 and published as: US2009/02022626 on Aug. 13, 2009.

International Preliminary Report on Patentability dated: Nov. 6, 2012 in International Application No. PCT/US2011/000757 filed, Apr. 29, 2011 and published as: WO/2009/099650 on Aug. 13, 2009.

International Search Report and Written Opinion dated: Dec. 21, 2011 in International Application No. PCT/US2011/000757 filed, Apr. 29, 2011 and published as: WO/2009/099650 on Aug. 13, 2009.

International Preliminary Report on Patentability mailed on: Aug. 9, 2011, in International Application No. PCT/EP2010/000722 filed on Feb. 5, 2010 and published as WO 2010/089128 on Aug. 12, 2010.

International Search Report and Written Opinion mailed on: Mar. 9, 2011, in International Application No. PCT/EP2010/000722 filed on Feb. 5, 2010 and published as WO 2010/089128 on Aug. 12, 2010.

International Preliminary Report on Patentability mailed on: Jun. 28, 2011, in International Application No. PCT/US2010/000369 filed on Feb. 11, 2010 and published as WO 2010/093436 on Aug. 19, 2010.

International Search Report and Written Opinion mailed on: Sep. 21, 2010, in International Application No. PCT/US2010/000369 filed on Feb. 11, 2010 and published as WO 2010/093436 on Aug. 19, 2010.

International Preliminary Report on Patentability mailed on: Aug. 10, 2010, in International Application No. PCT/US2009/000771 filed on Feb. 6, 2009 and published as WO 2010/099650 on Aug. 13, 2009.

International Search Report and Written Opinion mailed on: Aug. 28, 2009,in International Application No. PCT/US2009/000771 filed on Feb. 6, 2009 and published as WO 2010/099650 on Aug. 13, 2009.

International Preliminary Report on Patentability mailed on: Aug. 11, 2009, in International Application No. PCT/US2008/001631 filed on Feb. 7, 2008 and published as WO 2008/115319 on Sep. 25, 2008.

International Search Report and Written Opinion mailed on: Jan. 21, 2009, in International Application No. PCT/US2008/001631 filed on Feb. 7, 2008 and published as WO 2008/115319 on Sep. 25, 2008.

International Preliminary Report on Patentability mailed on: Dec. 3, 2008, in International Application No. PCT/US2007/009840 filed on Apr. 23, 2008 and published as WO 2007/142755 on Dec. 13, 2007.

International Search Report and Written Opinion mailed on: Aug. 5, 2008, in International Application No. PCT/US2007/009840 filed on Apr. 23, 2008 and published as WO 2007/142755 on Dec. 13, 2007.

International Preliminary Report on Patentability mailed on: Feb. 26, 2008, in International Application No. PCT/US2006/032371 filed on Aug. 21, 2006 and published as WO 2007/024707 on Mar. 1, 2007.

International Search Report and Written Opinion mailed on: Jul. 23, 2007, in International Application No. PCT/US2006/032371 filed on Aug. 21, 2006 and published as WO 2007/024707 on Mar. 1, 2007.

Extended European Search Report mailed: Feb. 15, 2011 in European Application Serial No. EP09709019.5, filed Feb. 9, 2009.

Extended Search Report mailed: Oct. 24, 2011 in European Application Serial No. 06813535.9, Extended Search Report mailed: Oct. 24, 2011.

Office Action mailed on Oct. 17, 2014 in U.S. Appl. No. 13/775,906, filed Feb. 25, 2013 and published as US 2013-0237561 on Sep. 12, 2013.

Bonacucina et al., "Effect of hydroxypropyl beta-cyclodextrin on the self-assembling and thermogelation properties of Poloxamer 407" Eur J Pharm Sci (2007) 32(2):115-22.

(56) References Cited

OTHER PUBLICATIONS

Shaker et al., "In-Situ Injectable Thermosensitive Gel Based on Poloxamer as a New Carrier for Tamoxifen Citrate" International Journal of Pharmacy and Pharmaceutical Sciences (2013) 5(Suppl. 4):429-437.

Chen et al., "Mechanical, rheological and release behaviors of a poloxamer 407/poloxamer 188/carbopol 940 thermosensitive composite hydrogel" Molecules (2013) 18:12415-12425.

Charrueau et al., "Poloxamer 407 as a thermogelling and adhesive polymer for rectal administration of short-chain fatty acids." Drug Dev. Ind. Pharm. (2001) 27(4):351-357.

Bourre et al., "Potential efficacy of a delta 5-aminolevulinic acid thermosetting gel formulation for use in photodynamic therapy of lesions of the gastrointestinal tract." Pharmacol. Res. (2002) 45(2):159-165.

Shin et al., "Permeation of piroxicam from the poloxamer gels." Drug Dev. Ind. Pharm. (1999) 25(3):273-278.

Fawaz et al., "Comparative in vitro-in vivo study of two quinine rectal gel formulations." Int. J. Pharm. (2004) 280(1-2):151-162.

Hayashi et al., "Intravesical Toll-like receptor 7 agonist R-847; Optimization of its formulation in an orthotopic mouse model of Bladder Cancer", International Journal of Urology (2010) 17:483-491.

Tyagi et al., "Local drug delivery to bladder using technology innovations," The Urological Clinics of North America, Nov. 2006, vol. 33, No. 4, pp. 519-530.

Office Action mailed on Apr. 30, 2014 in U.S. Appl. No. 13/775,906, filed Feb. 25, 2013 and published as US 2013-0237561 on Sep. 12, 2013.

Spohn et al., "Synthetic lipopeptide adjuvants and Toll-like receptor 2—structure-activity relationships" Vaccine (2004) 22(19):2494-2499.

Shen et al., "Intravesical Treatments of Bladder Cancer: Review" Pharmaceutical Research (2008) 25(7):1500-1510.

Wientjes et al., "Bladder Wall Penetration of Intravesical Mitomycin C in Dogs" Cancer Research (1991) 51:4347-4354.

\* cited by examiner

A

B

PHARMACEUTICAL COMPOSITIONS COMPRISING IMIDAZOQUINOLIN(AMINES) AND DERIVATIVES THEREOF SUITABLE FOR LOCAL ADMINISTRATION

RELATED APPLICATIONS

This application is filed under 35 U.S.C. §371 as the U.S. national phase of International Application PCT/EP2010/000722, filed Feb. 5, 2010, which designated the U.S. and claims priority to the International Application No. PCT/EP2009/000834, filed Feb. 6, 2009. The entire disclosure of both applications, including the drawings, is hereby incorporated herein by reference.

The present invention relates in general to the field of modulators of the innate immune system, particularly to pharmaceutical compositions comprising imidazoquinolin(amines) and derivatives thereof, preferably suitable for local administration, such as, intravesical administration. In addition, the present invention concerns the use of imidazoquinolin(amines) and derivatives thereof for intravesical treatment of bladder diseases, such as, for example, bladder cancer and cystitis. The present invention furthermore comprises methods of treatment for these diseases as well as methods of administration of the inventive pharmaceutical compositions.

Induction and/or enhancement of immune responses of the innate immune system and, depending on the type of trigger, the adaptive immune system, plays an important role in modern medicine in the treatment and prevention of numerous diseases. For such a purpose, immunomodulatory compositions are widely used in the art, which address a small number of receptors, called pattern recognition receptors. These pattern recognition receptors typically recognize conserved molecular patterns that distinguish foreign organism, like viruses, bacteria, fungi and parasites from cells of their hosts. As known of today, pattern recognition receptors include, inter alia, so called members of the Toll-like receptor (TLR) family, the first family of pattern recognition receptors studied in detail.

TLRs are transmembrane proteins which recognize ligands of the extracellular milieu or of the lumen of endosomes. Following ligand-binding they transduce the signal via cytoplasmic adaptor proteins which leads to triggering of a host-defence response and entailing production of antimicrobial peptides, proinflammatory chemokines and cytokines, anti-viral cytokines etc. To date, at least 10 members of Toll-like receptors (TLRs 1-10) have been identified in human and 13 (TLRs 1-13) in mice. Those Toll-like receptors (TLRs) in human include TLR1-TLR2, which recognize Triacyl lipopeptides; Toll-like receptors TLR1-TLR6, which recognize diacyl lipopeptide; Toll-like receptor TLR2, which recognize peptidoglycans; Toll-like receptor TLR3, which is known to recognize dsRNA, a viral product; Toll-like receptor TLR4, which has LPS (lipopolysachharide) of Gram-negative bacteria as a known ligand; Toll-like receptor TLR5, which recognizes bacterial flagellin(s); Toll-like receptors TLR7/8, which known ligands comprise imidazoquinolines, guanosine analogs and ssRNA; Toll-like receptor TLR9, which recognizes unmethylated CpG motifs frequently found in the genome of bacteria, viruses and protozoans, but not in vertebrates; TLR9 furthermore recognizes malaria pigment hemozoin, a digestion product of haemoglobin; Finally, the Toll-like receptor TLR10 was shown to directly associate with MyD88, the common Toll IL-1 receptor domain adapter (see e.g. Hasan et al., *The Journal of Immunology*, 2005, 174: 2942-2950). After recognition of microbial pathogens, these TLRs typically trigger intracellular signalling pathways that result in induction of inflammatory cytokines (e.g. TNF-alpha, IL-6, IL-1-beta and IL-12), type I interferon (IFN-beta and multiple IFN-alpha) and chemokines (Kawai, T. and S. Akira (2006). "TLR signalling." Cell Death Differ 13(5): 816-25).

Among the above TLRs, TLR3, TLR7 and TLR9 are of major importance. TLR7 recognizes small synthetic immune modifiers including imiquimod, R-848, loxoribine, and bropirimine, all of which are already applied or promising for clinical use against viral infections and cancers. Additionally, plasmacytoid dendritic cells express TLR7 and TLR9, and respond to TLR7 and TLR9 ligands by producing a large amount of interferon (IFN-alpha). These results indicate that TLR3, TLR7 and TLR9 may play an important role in detecting and combating viral infections.

A particular example of immune modifiers as described above includes imiquimod (within the following description also referred as R-837, TMX, TMX-101), which belongs to the class of imidazoquinolin(amine) immune modifiers. The immunomodulatory molecule imiquimod (1-isobutyl-1H-imidazo[4,5-c]quinolin-4-amine) was demonstrated to have clinical efficacy in oncological, viral and inflammatory diseases. The mechanism for the immunostimulatory activity of imiquimod is thought to be due in substantial part to enhancement of the immune response by induction of various important cytokines (e.g., interferons, interleukins, tumor necrosis factor, etc.). Even if the exact mechanism of action of imiquimod is not yet known, the binding of imiquimod to the toll-like receptor 7 (TLR7) is regarded to be one essential step in activating the immune system. Cells stimulated by imiquimod via TLR-7 secrete cytokines (primarily interferon-α (IFN-α), interleukin-6 (IL-6) and tumor necrosis factor-α (TNF-α) contributing to the anti-viral, anti-tumor, and anti-inflammatory properties of the agent.

It has been shown that imiquimod is a potent immune modulator currently used as a first line topical therapy for genital warts and superficial basal cell carcinomas (Purdon C H, Azzi C G, Zhang J, Smith E W, Maibach H I. Penetration enhancement of transdermal delivery—current permutations and limitations. *Crit. Rev Ther Drug Carrier Syst.* 2004; 21: 97-132; Chang Y C, Madkan V, Cook-Norris R, Sra K, Tyring S. Current and potential uses of imiquimod. *South Med J* 2005; 98: 914-20; Wagstaff A J, Perry C M. Topical imiquimod: a review of its use in the management of anogenital warts, actinic keratoses, basal cell carcinoma and other skin lesions. *Drugs.* 2007; 67: 2187-210). In addition, imiquimod has been used for the treatment of malignant skin lesions including melanoma and basal cell carcinoma (Wagstaff A J, Perry C M. Topical imiquimod: a review of its use in the management of anogenital warts, actinic keratoses, basal cell carcinoma and other skin lesions. *Drugs.* 2007; 67: 2187-210). Imiquimod induces proinflammatory cytokines and chemokines in vitro and in vivo (Chan M, Hayashi T, Kuy C S et al. Synthesis and Immunological Characterization of Toll-Like Receptor 7 Agonistic Conjugates. *Bioconjugate chemistry.* 2009) that attract immune cells to the local site of administration (Barnetson R S, Satchell A, Zhuang L, Slade H B, Halliday G M. Imiquimod induced regression of clinically diagnosed superficial basal cell carcinoma is associated with early infiltration by CD4 T cells and dendritic cells. *Clinical and experimental dermatology,* 2004; 29: 639-43).

Further, imidazoquinolines have been shown to direct cytotoxic effects to bladder cancer cells and induce them to secrete proinflammatory cytokines (Smith E B, Schwartz M, Kawamoto H et al. Antitumor effects of imidazoquinolines in urothelial cell carcinoma of the bladder. *The Journal of urology.* 2007; 177: 2347-51). It is further described that imidazoquinolines have antitumor effects in orthotopic bladder cancer mouse models (Smith E B, Schwartz M, Kawamoto H et al. Antitumor effects of imidazoquinolines in urothelial cell carcinoma of the bladder. *The Journal of urology.* 2007; 177: 2347-51).

In addition, it was shown that TLR-7 is also expressed in murine and human bladder cancer cell lines and imidazoquinolines have potent direct biological effects on urothelial cell carcinoma cells by decreasing cell viability and inducing apoptosis and cytokine production (Smith E B, Schwartz M, Kawamoto H, et al. Antitumour effects of Imidazoquinolines in urothelial cell carcinoma of the bladder. J Urol 2007; 177:2347). The direct effects appear to be the result of c-Myc down-regulation and might synergize with the immunomodulating action of imidazoquinolines (Liu H, Schwartz M J, Hwang D H, Scherr O S. Tumour growth inhibition by an imidazoquinoline is associated with c-Myc down-regulation in urothelial cell carcinoma. BJU Int 2008; 101:894-901). Additionally, initial results in an immune competent, orthotopic mouse model suggested antitumour effects in vivo (Smith E B, Schwartz M, Kawamoto H, et al. Antitumour effects of Imidazoquinolines in urothelial cell carcinoma of the bladder. J Urol 2007; 177:2347; Liu H, Schwartz M J, Hwang D H, Scherr O S. Tumour growth inhibition by an imidazoquinoline is associated with c-Myc down-regulation in urothelial cell carcinoma. BJU Int 2008; 101: 894-901). Therefore, imidazoquinolines have therapeutic potential as intravesical agent for bladder cancer.

Although some of the beneficial effects of immune modifiers such as imiquimod are known, the ability to provide therapeutic benefit via local administration of these immune modifiers for treatment of a particular condition at a particular location may be hindered by a variety of factors. These factors include insolubility and/or degradation of these immune modifiers in the formulation prior, during or even subsequent to administration, but also physical instability of the formulation, including factors such as separation of components, thickening, precipitation/agglomeration of active ingredients, and the like, as well as poor permeation of the immune modifier(s) into the surrounding tissue or cells upon administration. Specifically, the solubility of the immune modifier imiquimod is critical, and its use in pharmaceutical compositions, in particular, in liquid or semi-liquid compositions is limited due to its hydrophobic properties. Even though imiquimod is soluble in low concentrations in polar organic solvents such as DMSO, dimethyl formide, and N-methyl-2-pyrrolidone, such solvents do not allow for administration of imiquimod at or in the human body due to their various toxic effects. Non-toxic solvents, however, such as water or ethanol solubilise member of the imidazoquinolin(amin)es, such as imiquimod, only slightly and only allow for administration of imiquimod at or in the human body in low (sub-therapeutic) concentrations.

Therefore, according to a first aspect of the present invention, there is a need to provide a pharmaceutical composition, particularly as a liquid or semi-liquid formulation, which allows to solubilise imidazoquinolin(amin)es, such as imiquimod, in an appreciably manner and therefore allows for higher effective concentrations of immune modifiers such as imiquimod, when administered to the subject in need thereof. Particularly, there is a need in the art to provide such liquid or semi-liquid formulation for local administration modes, which do not exhibit toxic effects but exhibit improved solubility and preferably diminished physical instability of the formulation.

However, the use of immune modifiers, particularly of members of the class of imidazoquinolin(amin)es, such as imiquimod, for the treatment of oncological and viral diseases is also limited by its various side effects. E.g. imiquimod is reported to cause, for example, agitation, anemia, angioedema, arrhythmias, capillary leak syndrome, cardiac failure, cardiomyopathy, cerebrovascular accident, depression, dyspnea, erythema multiforme, exfoliative dermatitis, Henoch-Schönlein purpura syndrome, idiopathic thrombocytopenia purpura, insomnia, ischemia, leukopenia, liver function abnormal, lymphoma, multiple sclerosis aggravated, paresis, proteinuria, pulmonary edema, seizure, syncope, thrombocytopenia, and thyroiditis.

In order to reduce the risk of such severe side effects—which may be life-threatening in some cases—it is currently essentially administered locally instead of systemically. In this context, routes for systemic administration in general include, for example, transdermal, oral, or parenteral routes, including subcutaneous, intravenous, intramuscular, intraarterial, intradermal and intraperitoneal injections and/or intranasal administration routes. Such systemic administration typically leads to an overall distribution of the immune modifiers through the humans body and therefore significantly increases the risk of side effects. In contrast, routes for local administration in general include, for example, topical administration routes but also intradermal, transdermal, subcutaneous, or intramuscular injections or intralesional, intracranial, intrapulmonal, intracardial, and sublingual injections, wherein such administration typically occurs at the site of affliction and allows for a direct action of the drug while systemic side effects are significantly reduced, which are envisaged to occur upon systemic administration.

In the context of immune modifiers as defined above, in particular imidazoquinolin(amin)es, such as imiquimod or its derivatives, the specific requirement of local administration due to the above-mentioned physico-chemical properties of these compounds and side effects upon systemic administration limits their therapeutical application and the number of diseases to be treated therewith. At present, the majority of diseases, which may be treated with imiquimod or its derivatives are specific diseases of the skin, including skin cancers, such as, basal cell carcinoma, Bowen's disease, superficial squamous cell carcinoma as well as genital warts (Condylomata acuminata). A further prominent disease, which may be treated with immune modifiers, in particular imidazoquinolin (amin)es, such as imiquimod, includes bladder diseases, in particular bladder cancer and cystitis.

In this context, bladder cancer refers to any of several types of (malignant or non-malignant) neoplastic diseases of the urinary bladder. It is one of the fastest growing cancers worldwide due to the rapidly aging populations of most countries. Every year in the United States more than 60,000 people are newly diagnosed with bladder cancer, 80% of these have non-invasive bladder cancer. Since the mortality rate of bladder cancer is relatively low, the total number of patients in the US and in Europe is above 400,000. Thus, urinary bladder cancer is the fifth most common malignancy among men in Western society. The majority of bladder cancer cases are diagnosed as non-invasive, superficial tumors that are potentially curable by surgical and immune therapy (Schenk-Braat E A, Bangma C H. Immunotherapy for superficial bladder cancer. *Cancer Immunol Immunother* 2005; 54: 414-23).

So far the majority of non-invasive (superficial) bladder cancer patients are treated with so called "bacillus Calmette-Guerin (BCG) solutions", which are administered via the intravesical route. However, such BCG solutions are uncharacterized products composed by an attenuated form of the bacterium *Mycobacterium tuberculosis*, and therefore, exhibiting a poor safety profile.

In addition, superficially growing tumors can be removed by transurethral resection but the recurrence rate is high. To prolong the tumor-free intervals after surgical resection, intravesical treatment with *Mycobacterium bovis* Baccilus-Calmette-Guerin (BCG), the vaccine strain against tuberculosis infection, is currently used as an adjuvant treatment option (Alexandroff A B, Jackson A M, O'Donnell M A, James K. BCG immunotherapy of bladder cancer: 20 years on. *Lancet*. 1999; 353: 1689-94. De Jager R, Guinan P, Lamm D et al. Long-term complete remission in bladder carcinoma in situ with intravesical TICE bacillus Calmette Guerin. Overview analysis of six phase II clinical trials. *Urology*. 1991; 38: 507-13. Totterman T H, Loskog A, Essand M. The immunotherapy of prostate and bladder cancer. *BJU international*. 2005; 96: 728-35.)

However, *M. bovis* BCG treatment induces non-specific local inflammation in the bladder accompanied with various proinflammatory cytokines (IL-2, IL-6, IL-8 and TNFa) (De Boer E C, Rooijakkers S J, Schamhart D H, Kurth K H. Cytokine gene expression in a mouse model: the first instillations with viable bacillus Calmette-Guerin determine the succeeding Th1 response. *The Journal of urology*. 2003; 170: 2004-8) and chemokines that in turn initiate infiltration of immune cells in the bladder urothelium (Suttmann H, Riemensberger J, Bentien G et al. Neutrophil granulocytes are required for effective Bacillus Calmette-Guerin immunotherapy of bladder cancer and orchestrate local immune responses. *Cancer research*. 2006; 66: 8250-7. Simons M P, O'Donnell M A, Griffith T S. Role of neutrophils in BCG immunotherapy for bladder cancer. *Urologic oncology*. 2008; 26: 341-5). BCG instillation causes non-specific stimulation of the immune system, which induces local infiltration of the bladder wall by activated T cells derived by cell mediated Immunity (Bohle A, Brandau S. Immune mechanisms in bacillus Calmette-Guerin immunotherapy for superficial bladder cancer. *The Journal of urology*. 2003; 170: 964-9).

The incidence of non-muscle invasive urothelial cell carcinoma of the bladder (NMIBC) is high (Babjuk M, Oosterlinck W, Sylvester R, Kaasinen E, Böhle A, Palou-Redorta J; European Association of Urology (EAU). EAU guidelines on non-muscle-invasive urothelial carcinoma of the bladder. Eur Urol 2008; 54:303-14) and the prevalence is even higher due to the high recurrence rate after primary trans urethral resection. In patients at high risk of tumour recurrence and/or progression to muscle-invasive disease, intravesical BCG immunotherapy for at least one year is indicated (Babjuk M, Oosterlinck W, Sylvester R, Kaasinen E, Böhle A, Palou-Redorta J; European Association of Urology (EAU). EAU guidelines on non-muscle-invasive urothelial carcinoma of the bladder. Eur Urol 2008; 54:303-14). However, BCG is only partially effective and serious local and systemic side effects may occur (Witjes J A, Palou J, Soloway M, Lamm O, Brausi M, Spermon J R, Persad R, Buckley R, Akaza H, Colombel M, Böhle A. Clinical Practice recommendations for the prevention and management of intravesical therapy-associated adverse events. Eur. Urol Suppl 2008; 7:667-74). Therefore, development of new intravesical treatment options to lower tumour recurrence and progression of NMIBC remains essential.

As a further bladder diseases, cystitis typically comprises an inflammation of the urinary bladder and occurs when the normally sterile lower urinary tract (urethra and bladder) is infected by bacteria and becomes irritated and inflamed. Because of the risk of the infection spreading to the kidneys and due to the high complication rate in the elderly population and in diabetics, prompt treatment is almost always recommended. In order to control the bacterial infection cystitis is usually treated with antibiotics. Commonly used antibiotics for the treatment include, for example, nitrofurantoin, trimethoprim-sulfamethoxazole, amoxicillin, cephalosporins, ciprofloxacin or levofloxacin, and doxycycline. However, such antibiotic therapies often disrupt the normal balance of the intestinal flora causing diarrhea. In addition, an antibiotic-induced disruption of the population of the bacteria normally present as constituents of the normal vaginal flora may also occur, and may lead to overgrowth of yeast species of the genus *Candida* in the vulvo-vaginal area.

For such diseases, particularly for the treatment of bladder diseases such as non-invasive cancer and/or cystitis, the provision of an alternative agent which acts via an activation of the immune system would be desirable. However, even though immune modifiers as defined above, particularly imiquimod or its derivatives, may be used for the treatment of these diseases, administration may be hampered by severe side effects upon systemic administration as explained above. Furthermore, when administered locally, such immune modifiers, particularly imiquimod or its derivatives, are typically not present in a therapeutically effective amount in vivo due to their (pharmaceutically challenging) physico-chemical properties. Such pharmaceutical compositions have also not yet been described in the art, indicating the outstanding challenge in the art. As known to a skilled person, in order to provide such a specific pharmaceutical composition various pharmaceutical aspects, such as dose, excipient compatibility, solubility, stability, sterile manufacturing, scale-up feasibility, deliverable with catheter, costs, and compliance of the patient, as well as pharmacological aspects, such as biological activity, membrane permeability, duration of effect, low systemic circulation (in order to avoid systemic side effects) and toxicity profile have to be considered. As for many other active agents, the provision of pharmaceutical compositions comprising the desired active agent and releasing the agent such that local drug delivery is ensured is one of the major challenges for each pharmacist. Additionally, the (critical) physico-chemical properties of e.g. imidazoquinolin (amines), in particular the hydrophobicity profile of this compound class, have to be taken into account, which (in view of the approaches described in the art) typically lead to an insufficient in vivo concentration of the administered immune modifier compound acting as TLR-7 ligand.

Therefore, according to a second aspect there is an urgent need to provide a pharmaceutical composition suitable for specific local delivery of immune modifiers as defined above, particularly of imiquimod or its derivatives, e.g. for treating bladder diseases, e.g. via an intravesical administration route.

In summary, as outlined above, imiquimod is an active agent efficient for the treatment of oncological, viral, and inflammatory diseases. However, the use of imidazoquinolin (amin)es, such as imiquimod and its derivatives, in manufacturing a medicament is strictly limited by its solubility characteristics. In addition, various side effects are caused by imidazoquinolin(amin)es, such as imiquimod, if administered systemically. Accordingly, administration of this agent in a formulation which allows the agent to be specifically delivered to the target organ by using an appropriate pharmaceutical composition is of utmost importance. Therefore, it would be highly desirable to provide specific pharmaceutical compositions comprising imidazoquinolin(amin)es, such as imiquimod, in sufficiently solubilised amounts to allow efficient treatment of diseases mentioned herein. In addition, it would be preferable, if imidazoquinolin(amin)es, such as imiquimod and derivatives thereof, were formulated in a suitable formulation to be administered locally, in particular, intravesically, in order to combat bladder diseases, thereby significantly reducing the risk of severe systemic side effects.

Thus, it is an object of the present invention to provide a pharmaceutical composition suitable to comprise immune modifiers, in particular imidazoquinolin(amin)es, such as imiquimod, in therapeutically effective amounts. In addition, it is a further object of the present invention to provide pharmaceutical compositions suitable to be used in the manufacture of a medicament for intravesical treatment of bladder diseases, in particular of non-invasive bladder cancer and cystitis, via intravesical administration.

The object(s) of the present invention is (are) solved by the attached claims. Particularly, the object(s) of the present invention is (are) solved by a pharmaceutical composition comprising (a) an imidazoquinolin(amine) or a derivative thereof, e.g. imiquimod or a derivative thereof, and (b) at least one organic acid selected from acetic acid and/or lactic acid or a mixture thereof.

Thus, according to one preferred embodiment of the present invention, the pharmaceutical composition comprises an imidazoquinolin(amine) and at least one organic acid selected from acetic acid and/or lactic acid.

For some embodiments one or more of the following provisos apply:
pharmaceutical compositions for topical application are excluded,
pharmaceutical compositions comprising oil are excluded,
pharmaceutical compositions formulated as a w/o (water in oil) or o/w (oil in water) formulation are excluded,
pharmaceutical compositions formulated as a cream comprising 4% weight by weight imiquimod (1-isobutyl-1H-imidazo[4,5-c]-quinolin-4-amine) in the oil phase and 1% weight by weight lactic acid (85%) in the aqueous phase are excluded,
pharmaceutical compositions for parenteral administration are excluded,
pharmaceutical compositions comprising glycerine and/or sorbitol are excluded,
pharmaceutical compositions for parenteral administration comprising 1% weight by weight 1-isobutyl-1H-imidazo[4,5-c]-quinolin-4-amine and/or 1% weight by weight 1-(2-hydroxy-2-methylpropyl)-1H-imidazo[4,5-c]quinolin-4-amine or N-[4-(4-amino-2-ethyl-1H-imidazo[4,5-c]quinolin-1-yl)butyl]methanesulfoneamide and 1% or 2% weight by weight lactic acid (85%) or 0.6% weight by weight acetic acid are excluded,
pharmaceutical compositions comprising acetic acid and sorbitan monooleate 20 myristate or isopropyl myristate are excluded, and/or
pharmaceutical compositions comprising imiquimod chitosan nanoparticles obtained by mixing chitosan acetic acid solution with imiquimod are excluded.

According to another preferred embodiment of the present invention, the pharmaceutical composition further comprises at least one thermo-sensitive agent, wherein the at least one thermo-sensitive agent is preferably selected from chitosan or its derivatives, or from a poly(ethylene oxide)-poly(propylene oxide)-poly(ethylene oxide) copolymer (also termed PEO-PPO-PEO or poloxamer).

According to a further preferred embodiment of the present invention, the at least one thermo-sensitive agent is selected from chitosan or its derivatives, or from a poly(ethylene oxide)-poly(propylene oxide)-poly(ethylene oxide) copolymer (also termed PEO-PPO-PEO or poloxamer) including Pluronic F 108 Cast Solid Surfacta; Pluronic F 108 Pastille; Pluronic F 108 Prill; Pluronic F 108NF Prill (Poloxamer 338); Pluronic F 127; Pluronic F 127 Prill; Pluronic F 127 NF; Pluronic F 127 NF 500 BHT Prill; Pluronic F 127 NF Prill (Poloxamer 407); Pluronic F 38; Pluronic F 38 Pastille; Pluronic F 68; Pluronic F 68 Pastille; Pluronic F 68 LF Pastille; Pluronic F 68 NF Prill (Poloxamer 188); Pluronic F 68 Prill; Pluronic F 77; Pluronic F 77 Micropastille; Pluronic F 87; Pluronic F 87 NF Prill (Poloxamer 237); Pluronic F 87 Prill; Pluronic F 88 Pastille; Pluronic F 88 Prill; Pluronic F 98; Pluronic F 98 Prill; Pluronic L 10; Pluronic L 101; Pluronic L 121; Pluronic L 31; Pluronic L 35; Pluronic L 43; Pluronic L 44; Pluronic L 44 NF (Poloxamer 124); Pluronic L 61; Pluronic L 62; Pluronic L 62 LF; Pluronic L 62D; Pluronic L 64; Pluronic L 81; Pluronic L 92; Pluronic L44 NF INH surfactant (Poloxamer 124); Pluronic N 3; Pluronic P 103; Pluronic P 104; Pluronic P 105; Pluronic P 123 Surfactant; Pluronic P 65; Pluronic P 84; Pluronic P 85; and Poloxamer 403, or is selected from a mixture formed by any two or more of the afore defined thermo-sensitive agents.

According to a another preferred embodiment of the present invention, the at least one thermo-sensitive agent is selected from a poly(ethylene oxide)-poly(propylene oxide)-poly(ethylene oxide) copolymer (also termed PEO-PPO-PEO or poloxamer) including Pluronic F 108 Cast Solid Surfacta; Pluronic F 108 Pastille; Pluronic F 108 Prill; Pluronic F 108NF Prill (Poloxamer 338); Pluronic F 127; Pluronic F 127 Prill; Pluronic F 127 NF; Pluronic F 127 NF 500 BHT Prill; Pluronic F 127 NF Prill (Poloxamer 407); Pluronic F 38; Pluronic F 38 Pastille; Pluronic F 68; Pluronic F 68 Pastille; Pluronic F 68 LF Pastille; Pluronic F 68 NF Prill (Poloxamer 188); Pluronic F 68 Prill; Pluronic F 77; Pluronic F 77 Micropastille; Pluronic F 87; Pluronic F 87 NF Prill (Poloxamer 237); Pluronic F 87 Prill; Pluronic F 88 Pastille; Pluronic F 88 Prill; Pluronic F 98; Pluronic F 98 Prill; Pluronic L 10; Pluronic L 101; Pluronic L 121; Pluronic L 31; Pluronic L 35; Pluronic L 43; Pluronic L 44; Pluronic L 44 NF (Poloxamer 124); Pluronic L 61; Pluronic L 62; Pluronic L 62 LF; Pluronic L 62D; Pluronic L 64; Pluronic L 81; Pluronic L 92; Pluronic L44 NF INH surfactant (Poloxamer 124); Pluronic N 3; Pluronic P 103; Pluronic P 104; Pluronic P 105; Pluronic P 123 Surfactant; Pluronic P 65; Pluronic P 84; Pluronic P 85; and Poloxamer 403, or is selected from a mixture formed by any two or more of the afore defined thermo-sensitive agents.

In the context of the present invention, the inventive pharmaceutical composition comprises as a first component at least one organic acid selected from acetic acid and/or lactic acid or a mixture thereof. Although the organic acids "acetic acid" and "lactic acid" were already known to a skilled person for formulating pharmaceutical compositions in general, the inventors of the present invention surprisingly found that specifically these short chain carboxylic acids are suitable to efficiently solubilise imidazoquinolin(amin) or derivatives thereof, a finding which has not yet been published or discussed in the art. In addition, it was found that acetic acid and lactic acid exhibit solubilisation properties clearly superior to any other (carboxylic) acid. More specifically and even more surprisingly, acetic acid ($CH_3COOH$) and/or lactic acid (2-hydroxy propionic acid), solubilise imidazoquinolin (amine) 3 to 100 fold better than other short chain (carboxylic) acids, namely, phosphoric acid, succinic acid and citric acid.

These surprising effects are, without being bound to any theory, particularly due to the specific structure of imidazoquinolin(amines) or their derivatives as used herein, e.g. imiquimod, and the specific interaction of specifically acetic acid and lactic acid with the imidazoquinolin(amine) compound, which lead to an unexpected adduct structure. The term "imidazoquinolin(amin)es" refers both to the generic class of imidazoquinolins and, more specifically in a preferred embodiment, also to the subclass of imidazoquinolinamines.

Since imidazoquinolin(amines) or their derivatives as used herein have a basic functional group, particularly an amine moiety, it was assumed in the prior art literature that imidazoquinolin(amines) can be solubilised in any acidic solution at pH values below the $pK_a$ of compounds of that class, e.g. in case of imiquimod, i.e. of about 4. However, it was shown by the inventors of the present invention that the solubility of imidazoquinolin(amines) or their derivatives as used herein does not merely depend on the pH of the solution. Without being bound to any theory, those superior properties appear to be realized by an interaction, which occurs between imidazoquinolin(amines) or their derivatives as used herein and the (organic) acid specifically selected from acetic acid and/or lactic acid, thereby forming specific adducts between both components. Evidently, no such interaction seems to occur between imidazoquinolin(amines) or their derivatives as used herein and any other (organic) acid. Accordingly, it is assumed, that the surprising results of the present invention, particularly the specific superior solubilisation characteristics of imidazoquinolin(amines) or their derivatives as used herein in the organic acids acetic acid and/or lactic acid, seem to depend on specific structural properties which are exclusively realized by lactic and acetic acid but not by any other (organic) acid. Thereby, lactic and/or acetic acid form the anion in the adduct structure and the imidazoquinolin(amin)es being the positively charged cations.

According to a preferred embodiment of the present invention, the inventive pharmaceutical composition as defined above comprises an organic acid selected from acetic acid and/or lactic acid or a mixture thereof in a concentration of about 0.025 M to about 0.200 M, preferably in a concentration of about 0.025 M to about 0.100 M or in a concentration of about 0.100 M to about 0.200 M, or in a concentration of about 0.075 M to about 0.125 M, e.g. in a concentration of about 0.025 M to about 0.200 M, of about 0.030 M to about 0.200 M, of about 0.035 M to about 0.200 M, of about 0.040 M to about 0.200 M, of about 0.045 M to about 0.200 M, of about 0.050 M to about 0.200 M, of about 0.055 M to about 0.200 M, of about 0.060 M to about 0.200 M, of about 0.065 M to about 0.200 M, of about 0.070 M to about 0.200 M, of about 0.075 M to about 0.200 M, of about 0.080 M to about 0.200 M, of about 0.085 to 0 about 0.200 M, of about 0.090 M to about 0.200 M, of about 0.095 M to about 0.200 M, of about 0.095 M to about 0.200 M, of about 0.100 M to about 0.200 M, of about 0.125 M to about 0.200 M, of about 0.130 M to about 0.200 M, of about 0.135 M to about 0.200 M, of about 0.140 M to about 0.200 M, of about 0.145 M to about 0.200 M, of about 0.0150 M to about 0.200 M, of about 0.155 M to about 0.200 M, of about 0.160 M to about 0.200 M, of about 0.165 M to about 0.200 M, of about 0.170 M to about 0.200 M, of about 0.175 M to about 0.200 M, of about 0.180 M to about 0.200 M, of about 0.185 M to about 0.200 M, of about 0.190 M to about 0.200 M, or about 0.195 M to about 0.200 M, or preferably in a concentration of about 0.050 M to about 0.100 M, e.g. in a concentration of about 0.055 M to about 0.100 M, of about 0.060 M to about 0.100 M, of about 0.065 M to about 0.100 M, of about 0.070 M to about 0.100 M, of about 0.075 M to about 0.100 M, of about 0.080 M to about 0.100 M, of about 0.085 M to about 0.100 M, of about 0.090 M to about 0.100 M, or of about 0.095 M to about 0.100 M, or in a concentration of about 0.025 M to about 0.100 M, e.g. in a concentration of about 0.025 M to about 0.100 M, of about 0.030 M to about 0.100 M, of about 0.035 M to about 0.100 M, of about 0.040 M to about 0.100 M, of about 0.045 M to about 0.100 M, of about 0.050 M to about 0.100 M, of about 0.055 M to about 0.100 M, of about 0.060 M to about 0.100 M, of about 0.065 M to about 0.100 M, of about 0.070 M to about 0.100 M, of about 0.075 M to about 0.100 M, of about 0.080 M to about 0.100 M, of about 0.085 to 0 about 0.200 M, of about 0.090 M to about 0.100 M, of about 0.095 M to about 0.100 M, of about 0.095 M to about 0.100 M, or in a concentration of about 0.100 M to about 0.200 M, e.g. in a concentration of about 0.100 M to about 0.200 M, of about 0.125 M to about 0.200 M, of about 0.130 M to about 0.200 M, of about 0.135 M to about 0.200 M, of about 0.140 M to about 0.200 M, of about 0.145 M to about 0.200 M, of about 0.0150 M to about 0.200 M, of about 0.155 M to about 0.200 M, of about 0.160 M to about 0.200 M, of about 0.165 M to about 0.200 M, of about 0.170 M to about 0.200 M, of about 0.175 M to about 0.200 M, of about 0.180 M to about 0.200 M, of about 0.185 M to about 0.200 M, of about 0.190 M to about 0.200 M, or about 0.195 M to about 0.200 M, or in a concentration of about 0.075 M to about 0.125 M, e.g. of about 0.08 M to about 0.125 M, of about 0.085 M to about 0.125 M, of about 0.09 M to about 0.125 M, of about 0.095 M to about 0.125 M, of about 0.1 M to about 0.125 M, or of about 0.075 M to about 0.120 M, of about 0.075 M to about 0.115 M, of about 0.075 M to about 0.110 M, of about 0.075 M to about 0.105 M, of about 0.075 M to about 0.105 M or of about 0.08 M to about 0.120 M, e.g. of about 0.085 M to about 0.115 M, of about 0.09 M to about 0.110 M, of about 0.095 M to about 0.105 M, or of about 0.1 M. In this context, it was shown, that the amount of solubilised imidazoquinolin(amines) or their derivatives as used herein in solution is directly related to the acid concentration, i.e. to the concentration of acetic acid and lactic acid. Accordingly, higher concentrations of acetic acid and/or lactic acid or a mixture of both may be preferred for solubilising, preferably within the above defined ranges.

According to one specific embodiment of the present invention, the inventive pharmaceutical composition as defined above comprises a mixture of (two organic acids selected from) acetic acid and lactic acid, both together preferably exhibiting a "common concentration" of organic acids as defined above for the inventive pharmaceutical composition in general of about 0.025 M to about 0.200 M or of about 0.075 M to about 0.125 M any further concentration as defined above. In this context, the term "common concentration of organic acids" means that molarities of both organic acids acetic acid and lactic acid used for such a mixture, lead to a concentration as defined above. Even more preferably, both components of a mixture of (two organic acids selected from) acetic acid and lactic acid as defined above comprises a ratio of acetic acid:lactic acid of about 1:30 to about 30:1, e.g. of about 2:30, of about 3:30, of about 4:30, of about 5:30, of about 6:30, of about 7:30, of about 8:30, of about 9:30, of about 10:30, of about 11:30, of about 12:30, of about 13:30, of about 14:30, of about 15:30, of about 16:30, of about 17:30, of about 18:30, of about 19:30, of about 20:30, of about 21:30, of about 22:30, of about 23:30, of about 24:30, of about 25:30, of about 26:30, of about 27:30, of about 28:30, of about 29:30, of about 30:29, of about 30:28, of about 30:27, of about 30:26, of about 30:25, of about 30:24, of about 30:23, of about 30:22, of about 30:21, of about 30:20, of about 30:19, of about 30:18, of about 30:17, of about 30:16, of about 30:15, of about 30:14, of about 30:13, of about 30:12, of about 30:11, of about 30:10, of about 30:9, of about 30:8, of about 30:7, of about 30:6, of about 30:5, of about 30:4, of about 30:3, of about 30:2, or of about 30:1. Ranges of acetic acid:lactic acid are disclosed herein, which may be formed on the basis of any of the above values, e.g. 1:30 to 30:24, 1:30 to 23:30, 30:12 to 30:1, 30:8 to 30:1 etc.

According to one further specific embodiment of the present invention, the inventive pharmaceutical composition as defined above comprises exclusively either acetic acid or lactic acid as acid components. In any case, specific embodiments relate to compositions of the invention as described above which do not encompass any other acid, be it an organic or an inorganic acid, except for acetic acid and/or lactic acid. In another specific embodiment, the pharmaceutical composition comprises exclusively acetic acid (and no lactic acid) as (organic) acid component and, more preferably, apart from acetic acid no other acid at all, be it organic or inorganic. Instead, the pharmaceutical composition may (in another specific embodiment) comprise exclusively lactic acid (and no acetic acid) as (organic) acid and, more preferably, apart from lactic acid no other acid at all, be it organic or inorganic. In still another preferred embodiment, the pharmaceutical composition may comprise just acetic and or lactic acid as organic acid components, however, there may be at least one additional inorganic acid be included in the pharmaceutical composition of the invention, e.g. phosphoric acid, HCl etc.

According to another specific embodiment of the present invention, the inventive pharmaceutical composition as defined herein comprises exclusively lactic acid as acid component, preferably exhibiting a concentration of lactic acid as defined above for the inventive pharmaceutical composition in general of about 0.025 M to about 0.200 M or of about 0.075 M to about 0.125 M or any further concentration as defined above. In this specific embodiment it is even more preferred, that the inventive pharmaceutical composition as described above does not encompass any other acid than lactic acid, be it an organic or an inorganic acid. In this context, the inventors of the present invention surprisingly found that lactic acid is even more efficient in solubilising imidazoquinolin(amines) or their derivatives as used herein than acetic acid. Surprisingly, lactic acid is twice as efficient in solubilising imidazoquinolin(amines) or their derivatives as used herein as acetic acid. It was also found, that the solubility of imidazoquinolin(amines) or their derivatives as used herein in lactic acid is not enhanced by the addition of surfactants, such as Tween or Pluronic, which usually function as solubility enhancers in pharmaceutical compositions. This finding suggests that imidazoquinolin(amines) or their derivatives as used herein are not entrapped in micelles formed by surfactants and, therefore, supports the assumption that these imidazoquinolin(amines) interact with lactic acid by forming specifically structured adducts.

According to another specific embodiment of the present invention, the inventive pharmaceutical composition as defined herein comprises lactic acid in a concentration of about 0.075 M to about 0.125 M, e.g. of about 0.08 M to about 0.125 M, of about 0.085 M to about 0.125 M, of about 0.09 M to about 0.125 M, of about 0.095 M to about 0.125 M, of about 0.1 M to about 0.125 M, or of about 0.075 M to about 0.120 M, of about 0.075 M to about 0.115 M, of about 0.075 M to about 0.110 M, of about 0.075 M to about 0.105 M, of about 0.075 M to about 0.105 M or of about 0.08 M to about 0.120 M, e.g. of about 0.085 M to about 0.115 M, of about 0.09 M to about 0.110 M, of about 0.095 M to about 0.105 M, or of about 0.1 M.

According to a further specific embodiment of the present invention, the inventive pharmaceutical composition as defined herein typically comprises an pH-value of about 3 to about 8, preferably of about 3 to about 7, more preferably of about 3 to about 6, even more preferably of about 3 to about 5, and most preferably a pH-value of about 3.5 to about 4, including a pH-value in a range of about 3.5 to about 4.9, of about 3.5 to about 4.8, of about 3.6 to about 4.7, of about 3.6 to about 4.6, of about 3.7 to about 4.5, of about 3.7 to about 4.4, of about 3.8 to about 4.3, of about 3.8 to about 4.2, or of about 3.9 to about 4.1. The inventive pharmaceutical composition may be prepared and administered in a pH-value as defined above. If necessary, the pH-value may be further adjusted for the specific treatment and administration requirements, e.g. to a more neutral pH-value of about 5, 6, or 7 (pH 5 to 7), e.g. using buffers and additives as disclosed herein.

In the context of the present invention, the inventive pharmaceutical composition comprises as a further component an imidazoquinolin(amine) compound, such as imiquimod or a derivative thereof, as a biologically (therapeutically) active agent. In the context of the present invention, the term "imidazoquinolin(amines) or their derivatives as used herein" preferably refers to imidazoquinolin(amines) as defined in the following.

According to one particular embodiment, the inventive pharmaceutical composition comprises imidazoquinolin (amines) selected from following formula (I):

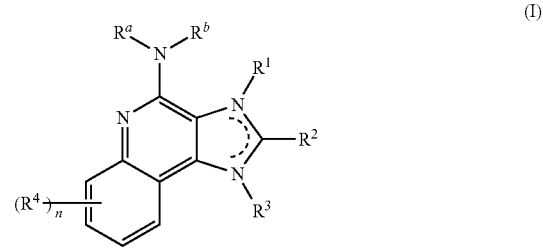

wherein
$R^1$, $R^2$, and $R^3$ are each independently selected from hydrogen; cyclic alkyl of three, four, or five carbon atoms; straight chain or branched chain alkyl containing one to about ten carbon atoms and substituted straight chain or branched chain alkyl containing one to about ten carbon atoms, wherein the substituent is selected from the group consisting of cycloalkyl containing three to about six carbon atoms and cycloalkyl containing three to about six carbon atoms substituted by straight chain or branched chain alkyl containing one to about four carbon atoms; fluoro- or chloroalkyl containing from one to about ten carbon atoms and one or more fluorine or chlorine atoms; straight chain or branched chain alkenyl containing two to about ten carbon atoms and substituted straight chain or branched chain alkenyl containing two to about ten carbon atoms, wherein the substituent is selected from the group consisting of cycloalkyl containing three to about six carbon atoms and cycloalkyl containing three to about six carbon atoms substituted by straight chain or branched chain alkyl containing one to about four carbon atoms; hydroxyalkyl of one to about six carbon atoms; alkoxyalkyl wherein the alkoxy moiety contains one to about four carbon atoms and the alkyl moiety contains one to about six carbon atoms; acyloxyalkyl wherein the acyloxy moiety is alkanoyloxy of two to about four carbon atoms or benzoyloxy, and the alkyl moiety contains one to about six carbon atoms, with the proviso that any such alkyl, substituted alkyl, alkenyl, substituted alkenyl, hydroxyalkyl, alkoxyalkyl, or acyloxyalkyl group does not have a fully carbon substituted carbon atom bonded directly to the nitrogen atom; benzyl; (phenyl)ethyl; and phenyl; said benzyl, (phenyl)ethyl or phenyl substituent being optionally substituted on the benzene ring by one or two moieties independently selected from the group consisting of alkyl of one to about four carbon atoms, alkoxy of one to about four carbon atoms, and halogen, with the proviso that when said benzene ring is substituted by two of said moieties, then the moieties together contain no more than six carbon atoms;
—CHR$_x$R$_y$, wherein R$_y$ is hydrogen or a carbon-carbon bond, with the proviso that when R$_y$ is hydrogen R$_x$ is alkoxy of one to about four carbon atoms, hydroxyalkoxy of one to about four carbon atoms, 1-alkynyl of two to about ten carbon atoms, tetrahydropyranyl, alkoxyalkyl wherein the alkoxy moiety contains one to about four carbon atoms and the alkyl moiety contains one to about four carbon atoms, 2-, 3-, or 4-pyridyl, and with the further proviso that when R$_y$ is a carbon-carbon bond R$_y$ and R$_x$ together form a tetrahydrofuranyl group optionally substituted with one or more substituents independently selected from the group consisting of hydroxy or hydroxyalkyl of one to about four carbon atoms;
straight chain or branched chain alkyl containing one to about eight carbon atoms, straight chain or branched chain hydroxyalkyl containing one to about six carbon atoms, morpholinomethyl, benzyl, (phenyl)ethyl and phenyl, the benzyl, (phenyl)ethyl or phenyl substituent being optionally substituted on the benzene ring by a moiety selected from the group consisting of methyl, methoxy, or halogen;
—C(R$_S$)(R$_T$)(X) wherein R$_S$ and R$_T$ are independently selected from the group consisting of hydrogen, alkyl of one to about four carbon atoms, phenyl, and substituted phenyl wherein the substituent is selected from the group consisting of alkyl of one to about four carbon atoms, alkoxy of one to about four carbon atoms, and halogen;
X is alkoxy containing one to about four carbon atoms, alkoxyalkyl wherein the alkoxy moiety contains one to about four carbon atoms and the alkyl moiety contains one to about four carbon atoms, haloalkyl of one to about four carbon atoms, alkylamido wherein the alkyl group contains one to about four carbon atoms, amino, substituted amino wherein the substituent is alkyl or hydroxyalkyl of one to about four carbon atoms, azido, alkylthio of one to about four carbon atoms, or morpholinoalkyl wherein the alkyl moiety contains one to about four carbon atoms;
$R^4$ is hydrogen, $C_{1-8}$ alkyl, $C_{1-8}$ alkoxy, or halo;
n is 1, 2, 3, or 4;
$R^a$ and $R^b$ are each independently hydrogen, $(C_1-C_6)$alkyl, hydroxy$(C_1-C_6)$ alkyl, amino$(C_1-C_6)$alkyl, aminosulfonyl, $(C_1-C_6)$alkanoyl, aryl, or benzyl, all of them optionally being substituted by one or more amino groups; or
$R^a$ and $R^b$ together with the nitrogen to which they are attached form a pyrrolidino, piperidino, or morpholino group; the dashed lines in the five membered ring of formula (I) above denote an optional bond that connects a nitrogen of the five membered ring to the carbon that is between the two nitrogens of the five membered ring, and when the bond is present, either $R^1$ or $R^3$ is absent; provided, that $R^a$ and $R^b$ together allow formation of a quarternary ammonium ion either at the nitrogen of the central stuctural element $N(R^a)(R^b)$ or by any quaternary ammonium ion being provided by $R^a$ and/or $R^b$;
or a pharmaceutically acceptable salt thereof. A pharmaceutically acceptable salt in the meaning of the present invention typically refers to an acetic or lactic acid salt.

According to one further particular embodiment, the inventive pharmaceutical composition comprises as imidazoquinoline or its derivative an imidazoquinolinamine such as 1H-imidazo[4,5-c]quinolin-4-amines, typically selected from one of following formulas (II) to (VI):
e.g. such compounds may be selected from formula (II)

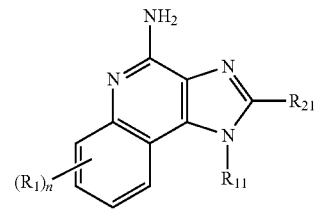

wherein
$R_{11}$ is selected from the group consisting of alkyl of one to about ten carbon atoms, hydroxyalkyl of one to about six carbon atoms, acyloxyalkyl wherein the acyloxy moiety is alkanoyloxy of two to about four carbon atoms or benzoyloxy, and the alkyl moiety contains one to about six carbon atoms, benzyl, (phenyl)ethyl and phenyl, said benzyl, (phenyl)ethyl or phenyl substituent being optionally substituted on the benzene ring by one or two moieties independently selected from the group consisting of alkyl of one to about four carbon atoms, alkoxy of one to about four carbon atoms and halogen, with the proviso that if said benzene ring is substituted by two of said moieties, then said moieties together contain no more than six carbon atoms;
$R_{21}$ is selected from the group consisting of hydrogen, alkyl of one to about eight carbon atoms, benzyl, (phenyl)ethyl and phenyl, the benzyl, (phenyl)ethyl or phenyl substituent being optionally substituted on the benzene ring by one or two moieties independently selected from the group consisting of alkyl of one to about four carbon atoms, alkoxy of one to about four carbon atoms and halogen, with the proviso that when the benzene ring is substituted by two of said moieties, then the moieties together contain no more than six carbon atoms; and each
$R_1$ is independently selected from the group consisting of alkoxy of one to about four carbon atoms, halogen, and alkyl of one to about four carbon atoms, and
n is an integer from 0 to 2, with the proviso that if n is 2, then said $R_1$ groups together contain no more than six carbon atoms;
or a pharmaceutically acceptable salt of any of the foregoing; or may be selected from formula (III)

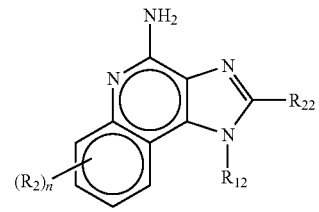

wherein
$R_{12}$ is selected from the group consisting of straight chain or branched chain alkenyl containing two to about ten carbon atoms and substituted straight chain or branched chain alkenyl containing two to about ten carbon atoms, wherein the substituent is selected from the group consisting of straight chain or branched chain alkyl containing one to about four carbon atoms and cycloalkyl containing three to about six carbon atoms; and cycloalkyl containing three to about six carbon atoms substituted by straight chain or branched chain alkyl containing one to about four carbon atoms; and $R_{22}$ is selected from the group consisting of hydrogen, straight chain or branched chain alkyl containing one to about eight carbon atoms, benzyl, (phenyl)ethyl and phenyl, the benzyl, (phenyl)ethyl or phenyl substituent being optionally substituted on the benzene ring by one or two moieties independently selected from the group consisting of straight chain or branched chain alkyl containing one to about four carbon atoms, straight chain or branched chain alkoxy containing one to about four carbon atoms, and halogen, with the proviso that when the benzene ring is substituted by two such moieties, then the moieties together contain no more than six carbon atoms; and each $R_2$ is independently selected from the group consisting of straight chain or branched chain alkoxy containing one to about four carbon atoms, halogen, and straight chain or branched chain alkyl containing one to about four carbon atoms, and n is an integer from zero to 2, with the proviso that if n is 2, then said $R_2$ groups together contain no more than six carbon atoms;

or a pharmaceutically acceptable salt of any of the foregoing;

or may be selected from formula (IV)

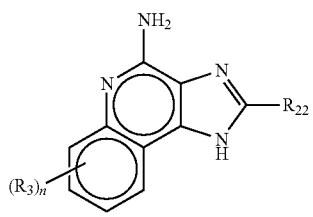

IV wherein $R_{22}$ is selected from the group consisting of hydrogen, straight chain or branched chain alkyl of one to about eight carbon atoms, benzyl, (phenyl)ethyl and phenyl, the benzyl, (phenyl)ethyl or phenyl substituent being optionally substituted on the benzene ring by one or two moieties independently selected from the group consisting of straight chain or branched chain alkyl of one to about four carbon atoms, straight chain or branched chain alkoxy of one to about four carbon atoms, and halogen, with the proviso that when the benzene ring is substituted by two such moieties, then the moieties together contain no more than six carbon atoms; and each $R_3$ is independently selected from the group consisting of straight chain or branched chain alkoxy of one to about four carbon atoms, halogen, and straight chain or branched chain alkyl of one to about four carbon atoms, and n is an integer from zero to 2, with the proviso that if n is 2, then said $R_3$ groups together contain no more than six carbon atoms;

or a pharmaceutically acceptable salt of any of the foregoing;

or may be selected from formula (V)

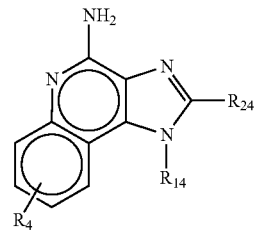

V wherein $R_{14}$ is —$CHR_xR_y$ wherein $R_y$ is hydrogen or a carbon-carbon bond, with the proviso that when $R_y$ is hydrogen $R_x$ is alkoxy of one to about four carbon atoms, hydroxyalkoxy of one to about four carbon atoms, 1-alkynyl of two to about ten carbon atoms, tetrahydropyranyl, alkoxyalkyl wherein the alkoxy moiety contains one to about four carbon atoms and the alkyl moiety contains one to about four carbon atoms, 2-, 3-, or 4-pyridyl, and with the further proviso that when $R_y$ is a carbon-carbon bond $R_y$ and $R_x$ together form a tetrahydrofuranyl group optionally substituted with one or more substituents independently selected from the group consisting of hydroxy and hydroxyalkyl of one to about four carbon atoms;

$R_{24}$ is selected from the group consisting of hydrogen, alkyl of one to about four carbon atoms, phenyl, and substituted phenyl wherein the substituent is selected from the group consisting of alkyl of one to about four carbon atoms, alkoxy of one to about four carbon atoms, and halogen; and is selected from the group consisting of hydrogen, straight chain or branched chain alkoxy containing one to about four carbon atoms, halogen, and straight chain or branched chain alkyl containing one to about four carbon atoms;

or a pharmaceutically acceptable salt of any of the foregoing;

or may be selected from formula (VI)

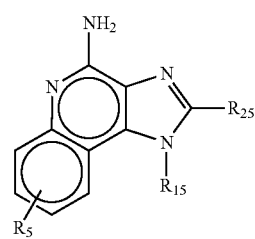

VI wherein $R_{15}$ is selected from the group consisting of: hydrogen; straight chain or branched chain alkyl containing one to about ten carbon atoms and substituted straight chain or branched chain alkyl containing one to about ten carbon atoms, wherein the substituent is selected from the group consisting of cycloalkyl containing three to about six carbon atoms and cycloalkyl containing three to about six carbon atoms substituted by straight chain or branched chain alkyl containing one to about four carbon atoms; straight chain or branched chain alkenyl containing two to about ten carbon atoms and substituted straight chain or branched chain alkenyl containing two to about ten carbon atoms, wherein the substituent is selected from the group consisting of cycloalkyl containing three to about six carbon atoms and cycloalkyl containing three to about six carbon atoms substituted by straight chain or branched chain alkyl containing one to about four carbon atoms; hydroxyalkyl of one to about six carbon atoms; alkoxyalkyl wherein the alkoxy moiety contains one to about four carbon atoms and the alkyl moiety contains one to about six carbon atoms; acyloxyalkyl wherein the acyloxy moiety is alkanoyloxy of two to about four carbon atoms or benzoyloxy, and the alkyl moiety contains one to about six carbon atoms; benzyl; (phenyl)ethyl; and phenyl; said benzyl, (phenyl)ethyl or phenyl, substituent being optionally substituted on the benzene ring by one or two moieties independently selected from the group consisting of alkyl of one to about four carbon atoms, alkoxy of one to about four carbon atoms, and halogen, with the proviso that when said benzene ring is substituted by two of said moieties, then the moieties together contain no more than six carbon atoms; $R_{25}$ is

wherein
$R_S$ and $R_T$ are independently selected from the group consisting of hydrogen, alkyl of one to about four carbon atoms, phenyl, and substituted phenyl wherein the substituent is selected from the group consisting of alkyl of one to about four carbon atoms, alkoxy of one to about four carbon atoms, and halogen;
X is selected from the group consisting of alkoxy containing one to about four carbon atoms, alkoxyalkyl wherein the alkoxy moiety contains one to about four carbon atoms and the alkyl moiety contains one to about four carbon atoms, hydroxyalkyl of one to about four carbon atoms, haloalkyl of one to about four carbon atoms, alkylamido wherein the alkyl group contains one to about four carbon atoms, amino, substituted amino wherein the substituent is alkyl or hydroxyalkyl of one to about four carbon atoms, azido, chloro, hydroxy, 1-morpholino, 1-pyrrolidino, alkylthio of one to about four carbon atoms; and
$R_5$ is selected from the group consisting of hydrogen, straight chain or branched chain alkoxy containing one to about four carbon atoms, halogen, and straight chain or branched chain alkyl containing one to about four carbon atoms;
or a pharmaceutically acceptable salt of any of the foregoing.

According to another particular embodiment, the inventive pharmaceutical composition comprises as imidazoquinoline or its derivative imidazoquinolin(amines) from following formula (VII):

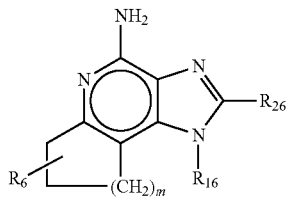

wherein
m is 1, 2, or 3;
$R_{16}$ is selected from the group consisting of hydrogen; cyclic alkyl of three, four, or five carbon atoms; straight chain or branched chain alkyl containing one to about ten carbon atoms and substituted straight chain or branched chain alkyl containing one to about ten carbon atoms, wherein the substituent is selected from the group consisting of cycloalkyl containing three to about six carbon atoms and cycloalkyl containing three to about six carbon atoms substituted by straight chain or branched chain alkyl containing one to about four carbon atoms; fluoro- or chloroalkyl containing from one to about ten carbon atoms and one or more fluorine or chlorine atoms; straight chain or branched chain alkenyl containing two to about ten carbon atoms and substituted straight chain or branched chain alkenyl containing two to about ten carbon atoms, wherein the substituent is selected from the group consisting of cycloalkyl containing three to about six carbon atoms and cycloalkyl containing three to about six carbon atoms substituted by straight chain or branched chain alkyl containing one to about four carbon atoms; hydroxyalkyl of one to about six carbon atoms; alkoxyalkyl wherein the alkoxy moiety contains one to about four carbon atoms and the alkyl moiety contains one to about six carbon atoms; acyloxyalkyl wherein the acyloxy moiety is alkanoyloxy of two to about four carbon atoms or benzoyloxy, and the alkyl moiety contains one to about six carbon atoms, with the proviso that any such alkyl, substituted alkyl, alkenyl, substituted alkenyl, hydroxyalkyl, alkoxyalkyl, or acyloxyalkyl group does not have a fully carbon substituted carbon atom bonded directly to the nitrogen atom; benzyl; (phenyl) ethyl; and phenyl; said benzyl, (phenyl)ethyl or phenyl substituent being optionally substituted on the benzene ring by one or two moieties independently selected from the group consisting of alkyl of one to about four carbon atoms, alkoxy of one to about four carbon atoms, and halogen, with the proviso that when said benzene ring is substituted by two of said moieties, then the moieties together contain no more than six carbon atoms; and
—CHR$_x$R$_y$, wherein R$_y$ is hydrogen or a carbon-carbon bond, with the proviso that when R$_y$ is hydrogen R$_x$ is alkoxy of one to about four carbon atoms, hydroxyalkoxy of one to about four carbon atoms, I-alkynyl of two to about ten carbon atoms, tetrahydropyranyl, alkoxyalkyl wherein the alkoxy moiety contains one to about four carbon atoms and the alkyl moiety contain-sone to about four carbon atoms, 2-, 3-, or 4-pyridyl, and with the further proviso that when R$_y$ is a carbon-carbon bond R$_y$ and R$_x$ together form a tetrahydrofuranyl group optionally substituted with one or more substituents independently selected from the group consisting of hydroxy and hydroxyalkyl of one to about four carbon atoms,
$R_{26}$ is selected from the group consisting of hydrogen, straight chain or branched chain alkyl containing one to about eight carbon atoms, straight chain or branched chain hydroxyalkyl containing one to about six carbon atoms, morpholinomethyl, benzyl, (phenyl)ethyl and phenyl, the benzyl, (phenyl)ethyl or phenyl substituent being optionally substituted on the benzene ring by a moiety selected from the group consisting of methyl, methoxy, and halogen; and
—C(R$_S$)(R$_T$)(X) wherein
$R_S$ and $R_T$ are independently selected from the group consisting of hydrogen, alkyl of one to about four carbon atoms, phenyl, and substituted phenyl wherein the substituent is selected from the group consisting of alkyl of one to about four carbon atoms, alkoxy of one to about four carbon atoms, and halogen;

X is selected from the group consisting of alkoxy containing one to about four carbon atoms, alkoxyalkyl wherein the alkoxy moiety contains one to about four carbon atoms and the alkyl moiety contains one to about four carbon atoms, haloalkyl of one to about four carbon atoms, alkylamido wherein the alkyl group contains one to about four carbon atoms, amino, substituted amino wherein the substituent is alkyl or hydroxyalkyl of one to about four carbon atoms, azido, alkylthio of one to about four carbon atoms, and morpholinoalkyl wherein the alkyl moiety contains one to about four carbon atoms, and $R_6$ is selected from the group consisting of hydrogen, fluoro, chloro, straight•chain or branched chain alkyl containing one to about four carbon atoms, and straight chain or branched chain fluoro- or chloroalkyl containing one to about four carbon atoms and at least one fluorine or chlorine atom;

and pharmaceutically acceptable salts thereof.

According to another particular embodiment, the inventive pharmaceutical composition comprises as imidazoquinoline or its derivative imidazoquinolin(amines) from following formula (VIII):

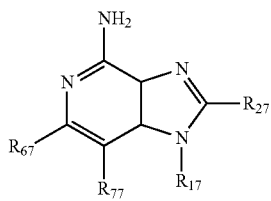

VIII wherein $R_{17}$ is selected from the group consisting of hydrogen; —$CH_2R_W$ wherein $R_W$ is selected from the group consisting of straight chain, branched chain, or cyclic alkyl containing one to about ten carbon atoms, straight chain or branched chain alkenyl containing two to about ten carbon atoms, straight chain or branched chain hydroxyalkyl containing one to about six carbon atoms, alkoxyalkyl wherein the alkoxy moiety contains one to about four carbon atoms and the alkyl moiety contains one to about six carbon atoms, and phenylethyl; and —CH=$CR_ZR_Z$ wherein each $R_Z$ is independently straight chain, branched chain, or cyclic alkyl of one to about six carbon atoms;

$R_{27}$ is selected from the group consisting of hydrogen, straight chain or branched chain alkyl containing one to about eight carbon atoms, straight chain or branched chain hydroxyalkyl containing one to about six carbon atoms, alkoxyalkyl wherein the alkoxy moiety contains one to about four carbon atoms and the alkyl moiety contains one to about six carbon atoms, benzyl, (phenyl)ethyl and phenyl, the benzyl, (phenyl)ethyl or phenyl substituent being optionally substituted on the benzene ring by a moiety selected from the group consisting of methyl, methoxy, and halogen; and morpholinoalkyl wherein the alkyl moiety contains one to about four carbon atoms;

$R_{67}$ and $R_{77}$ are independently selected from the group consisting of hydrogen and alkyl of one to about five carbon atoms, with the proviso that $R_{67}$ and $R_{77}$ taken together contain no more than six carbon atoms, and with the further proviso that when $R_{77}$ is hydrogen then $R_{67}$ is other than hydrogen and $R_{27}$ is other than hydrogen or morpholinoalkyl, and with the further proviso that when $R_{67}$ is hydrogen then $R_{77}$ and $R_{27}$ are other than hydrogen;

and pharmaceutically acceptable salts thereof.

According to an additional particular embodiment, the inventive pharmaceutical composition comprises as imidazoquinoline or its derivative imidazoquinolin(amines) from following formula (IX):

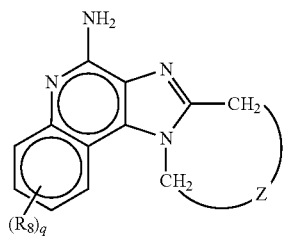

IX wherein

Z is selected from the group consisting of:

—$(CH_2)_p$— wherein p is 1 to 4;

—$(CH_2)_a$—$C(R_DR_E)(CH_2)_b$—, wherein a and b are integers and a+b is 0 to 3, $R_D$ is hydrogen or alkyl of one to four carbon atoms, and $R_E$ is selected from the group consisting of alkyl of one to four carbon atoms, hydroxy, —$OR_F$ wherein $R_F$ is alkyl of one to four carbon atoms, and —$NR_GR'_G$ wherein $R_G$ and $R'_G$ are independently hydrogen or alkyl of one to four carbon atoms; and —$(CH_2)_a$—(Y)—$(CH_2)_b$— wherein a and b are integers and a+b is 0 to 3, and Y is O, S, or —$NR_J$— wherein $R_J$ is hydrogen or alkyl of one to four carbon atoms;

and wherein q is 0 or 1; and $R_8$ is selected from the group consisting of alkyl of one to four carbon atoms, alkoxy of one to four carbon atoms, and halogen, and pharmaceutically acceptable salts thereof.

According to an even preferred embodiment, the inventive pharmaceutical composition comprises as imidazoquinolin (amine) the specific compound imiquimod, preferably having the specific formula 1-isobutyl-1H-imidazo[4,5-c]quinolin-4-amine, even more preferably comprising the following specific structure:

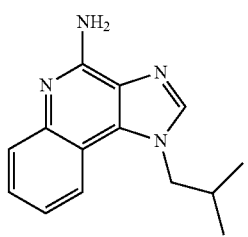

(X)

According to an even preferred embodiment, the inventive pharmaceutical composition comprises as imidazoquinolin (amine) the specific compound resiquimod, preferably comprising the following specific structure:

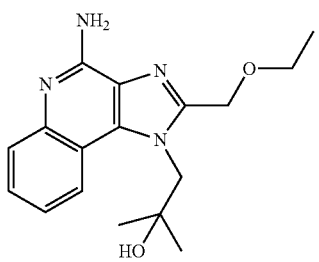

(XI)

The pharmaceutical composition according to the invention may also comprise a mixture of more than one imidazoquinolin(amine) as defined above, typically 2 to 4 imidazoquinolin(amines), which may e.g. be selected from any of the above disclosed compounds according formulae (I) to (XI). Preferably, at least one of the therapeutically active components in such a pharmaceutically active composition comprising more than one imidazoquinolin(amine) corresponds to formula (XI): imiquimod.

In the context of imidazoquinolin(amines) or their derivatives as defined above preferably following further definitions may apply:

In formulas containing the integer n and where n can be zero, one, or two, n is preferably zero or one.

The substituents $R_{11}$-$R_{17}$ above are generally designated "1-substituents" herein. In one embodiment, the 1-substituents are preferably alkyl containing one to six carbon atoms and hydroxyalkyl containing one to six carbon atoms, e.g., the 1-substituent is 2-methylpropyl or 2-hydroxy-2-methylpropyl.

The substituents $R_{21}$-$R_{27}$ above are generally designated "2-substituents" herein. In one embodiment, the 2-substituents are preferably hydrogen, alkyl of one to six carbon atoms, alkoxyalkyl wherein the alkoxy moiety contains one to four carbon atoms and the alkyl moiety contains one to four carbon atoms, and hydroxyalkyl of one to four carbon atoms, e.g., the 2-substituent is hydrogen, methyl, butyl, hydroxymethyl, ethoxymethyl or methoxyethyl.

The term "alkyl" preferably includes straight or branched $C_{1-10}$ alkyl groups, e.g., methyl, ethyl, propyl, butyl, pentyl, isopropyl, isobutyl, 1-methylpropyl, 3-methylbutyl, hexyl, and the like.

The term "lower alkyl" preferably includes straight or branched $C_{1-6}$ alkyl groups, e.g., methyl, ethyl, propyl, 1-methylethyl, butyl, 1-methylpropyl, 2-methylpropyl, 1,1dimethylethyl, pentyl, 1-methylbutyl, 2-methylbutyl, 3-methylbutyl, 1,1dimethylpropyl, 1,2-dimethylpropyl, 2,2-dimethylpropyl, and the like.

The term "alkylene" preferably refers to a divalent straight or branched hydrocarbon chain (e.g. ethylene —$CH_2$—$CH_2$—).

The term "$C_{3-7}$ cycloalkyl" preferably includes groups such as, cyclopropyl, cyclopentyl, cyclohexyl, cycloheptyl, and the like, and alkyl-substituted $C_{3-7}$ cycloalkyl group, preferably straight or branched $C_{1-6}$ alkyl group such as methyl, ethyl, propyl, butyl or pentyl, and $C_{5-7}$ cycloalkyl group such as, cyclopentyl or cyclohexyl, and the like.

The term "lower alkoxy" preferably includes $C_{1-6}$ alkoxy groups, such as methoxy, ethoxy or propoxy, and the like.

The term "lower alkanoyl" preferably includes $C_{1-6}$ alkanoyl groups, such as formyl, acetyl, propanoyl, butanoyl, pentanoyl or hexanoyl, and the like.

The term "$C_{7-11}$ aroyl" includes groups such as benzoyl or naphthoyl;

The term "lower alkoxycarbonyl" preferably includes $C_{2-7}$ alkoxycarbonyl groups, such as methoxycarbonyl, ethoxycarbonyl or propoxycarbonyl, and the like.

The term "lower alkylamino group" preferably means an amino group substituted by $C_{1-6}$ alkyl group, such as, methylamino, ethylamino, propylamino, butylamino, and the like.

The term "di(lower alkyl)amino group" preferably means an amino group substituted by the same or different and $C_{1-6}$ alkyl group (e.g. dimethylamino, diethylamino, ethylmethylamino).

The term "lower alkylcarbamoyl group" preferably means a carbamoyl group substituted by $C_{1-6}$ alkyl group (e.g. methylcarbamoyl, ethylcarbamoyl, propylcarbamoyl, butylcarbamoyl).

The term "Di(lower alkyl)carbamoyl group" preferably means a carbamoyl group substituted by the same or different and $C_{1-6}$ alkyl group (e.g. dimethylcarbamoyl, diethylcarbamoyl, ethyl methylcarbamoyl).

The term "halogen atom" as defined herein preferably means a halogen atom such as fluorine atom, chlorine atom, bromine atom or iodine atom.

The term "aryl" as defined herein preferably refers to a $C_{6-10}$ monocyclic or fused cyclic aryl group, such as phenyl, indenyl, or naphthyl, and the like.

The term "heterocyclic" as defined herein preferably refers to monocyclic saturated heterocyclic groups, or unsaturated monocyclic or fused heterocyclic group containing at least one heteroatom, e.g., 0-3 nitrogen atoms, 0-1 oxygen atom (—O—), and 0-1 sulfur atoms (—S—). In this context, non-limiting examples of saturated monocyclic heterocyclic group includes 5 or 6 membered saturated heterocyclic group, such as tetrahydrofuranyl, pyrrolidinyl, morpholinyl, piperidyl, piperazinyl or pyrazolidinyl. Non-limiting examples of unsaturated monocyclic heterocyclic group includes 5 or 6 membered unsaturated heterocyclic group, such as furyl, pyrrolyl, pyrazolyl, imidazolyl, thiazolyl, thienyl, pyridyl or pyrimidinyl. Non-limiting examples of unsaturated fused heterocyclic groups includes unsaturated bicyclic heterocyclic group, such as indolyl, isoindolyl, quinolyl, benzothizolyl, chromanyl, benzofuranyl, and the like.

Additionally, alkyl, aryl, and heterocyclic groups as defined herein can be optionally substituted with one or more substituents, wherein the substituents are the same or different, and include lower alkyl; $C_{1-6}$ alkoxy, such as methoxy, ethoxy or propoxy; carboxyl; $C_{2-7}$ alkoxycarbonyl, such as methoxycarbonyl, ethoxycarbonyl or propoxycarbonyl) and halogen; cycloalkyl and include $C_{3-6}$ cycloalkyl; hydroxyl; $C_{1-6}$ alkoxy; amino; cyano; aryl; substituted aryl, such as 4-hydroxyphenyl, 4-methoxyphenyl, 4-chlorophenyl or 3,4-dichlorophenyl; nitro and halogen, hydroxyl; hydroxy alkylene, such as hydroxymethyl, 2-hydroxyethyl or 3-hydroxypropyl; lower alkoxy; $C_{1-6}$ alkoxy $C_{1-6}$ alkyl, such as 2-methoxyethyl, 2-ethoxyethyl or 3-methoxypropyl; amino; alkylamino; dialkyl amino; cyano; nitro; acyl; carboxyl; lower alkoxycarbonyl; halogen; mercapto; $C_{1-6}$ alkylthio, such as, methylthio, ethylthio, propylthio or butylthio; substituted $C_{1-6}$ alkylthio, such as methoxyethylthio, methylthioethylthio, hydroxyethylthio or chloroethylthio; aryl; substituted $C_{6-10}$ monocyclic or fused-cyclic aryl, such as 4-hydroxyphenyl, 4-methoxyphenyl, 4-fluorophenyl, 4-chlorophenyl or 3,4-dichlorophenyl; 5-6 membered unsaturated heterocyclic, such as furyl, pyrrolyl, pyrazolyl, imidazolyl, thiazolyl, thienyl, pyridyl or pyrimidinyl; and bicyclic unsaturated heterocyclic, such as indolyl, isoindolyl, quinolyl, benzothiazolyl, chromanyl, benzofuranyl or phthalimino. Furthermore, the heterocyclic ring as defined herein can be optionally substituted with one or more substituents, wherein the substituents are the same or different, and include $C_{1-6}$ alkyl; hydroxy $C_{1-6}$ alkylene; $C_{1-6}$ alkoxy $C_{1-6}$ alkylene; hydroxyl; $C_{1-6}$ alkoxy; and cyano.

Finally, it will be appreciated by those skilled in the art that imidazoquinolin(amines) as defined above in the context of the present invention also may have a chiral center and may be isolated in optically active and racemic forms. Some compounds may exhibit polymorphism. It is to be understood that the present invention encompasses any racemic, optically-active, polymorphic, or stereoisomeric form, or mixtures thereof, of imidazoquinolin(amines) or their derivatives as defined above, which possess the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase) and how to determine nicotine agonist activity using the standard tests described herein, or using other similar tests which are well known in the art.

According to one embodiment the pharmaceutical composition according to the present invention typically comprises an imidazoquinolin(amine) or a derivative thereof as defined herein, preferably imiquimod or a derivative thereof, in an amount of about 0.005% (w/v) to about 5% (w/v), preferably in an amount of about 0.01% (w/v) to about 5% (w/v), more preferably in an amount of about 0.1% (w/v) to about 4% (w/v), even more preferably in an amount of about 0.1% (w/v) to about 3% (w/v), even further preferred in an amount of about 0.2% (w/v) to about 2% (w/v), and most preferably in an amount of about 0.2% (w/v) to about 1% (w/v) or even in an amount of about 0.5% (w/v) to about 1% (w/v), wherein the amounts as defined in % (w/v) may either be determined on the basis of the weight of imidazoquinolin(amine) or a derivative thereof as defined herein, preferably imiquimod or a derivative thereof, with respect to the total volume of the inventive pharmaceutical composition, when e.g. provided as a liquid or semi-liquid formulation. Alternatively, the above amounts may be defined in % (w/w), wherein the amount as defined in % (w/w) may either be determined on the basis of the weight of imidazoquinolin(amine) or a derivative thereof as defined above, preferably imiquimod or a derivative thereof, with respect to the total weight of the inventive pharmaceutical composition.

According to one particular preferred embodiment the pharmaceutical composition according to the present invention typically comprises an imidazoquinolin(amine) or a derivative thereof as defined herein, preferably imiquimod or a derivative thereof, in an amount of about 0.005% (w/v) to about 1, 2, 3, 4, or 5% (w/v), in an amount of about 0.01% (w/v) to about 1, 2, 3, 4, or 5% (w/v), in an amount of about 0.1% (w/v) to about 1, 2, 3, 4, or 5% (w/v), in an amount of about 0.2% (w/v) to about 1, 2, 3, 4, or 5% (w/v), in an amount of about 0.3% (w/v) to about 1, 2, 3, 4, or 5% (w/v), in an amount of about 0.4% (w/v) to about 1, 2, 3, 4, or 5% (w/v), in an amount of about 0.5% (w/v) to about 1, 2, 3, 4, or 5% (w/v), in an amount of about 0.6% (w/v) to about 1, 2, 3, 4, or 5% (w/v), in an amount of about 0.7% (w/v) to about 1, 2, 3, 4, or 5% (w/v), in an amount of about 0.8% (w/v) to about 1, 2, 3, 4, or 5% (w/v), in an amount of about 0.9% (w/v) to about 1, 2, 3, 4, or 5% (w/v), in an amount of about 1.0% (w/v) to about 2, 3, 4, or 5% (w/v), in an amount of about 1.1% (w/v) to about 2, 3, 4, or 5% (w/v), in an amount of about 1.2% (w/v) to about 2, 3, 4, or 5% (w/v), in an amount of about 1.3% (w/v) to about 2, 3, 4, or 5% (w/v), in an amount of about 1.4% (w/v) to about 2, 3, 4, or 5% (w/v), in an amount of about 1.5% (w/v) to about 2, 3, 4, or 5% (w/v), in an amount of about 1.6% (w/v) to about 2, 3, 4, or 5% (w/v), in an amount of about 1.7% (w/v) to about 2, 3, 4, or 5% (w/v), in an amount of about 1.8% (w/v) to about 2, 3, 4, or 5% (w/v), in an amount of about 1.9% (w/v) to about 2, 3, 4, or 5% (w/v), in an amount of about 2.0% (w/v) to about 3, 4, or 5% (w/v), in an amount of about 2.1% (w/v) to about 3, 4, or 5% (w/v), in an amount of about 2.2% (w/v) to about 3, 4, or 5% (w/v), in an amount of about 2.3% (w/v) to about 3, 4, or 5% (w/v), in an amount of about 2.4% (w/v) to about 3, 4, or 5% (w/v), in an amount of about 2.5% (w/v) to about 3, 4, or 5% (w/v), in an amount of about 2.6% (w/v) to about 3, 4, or 5% (w/v), in an amount of about 2.7% (w/v) to about 3, 4, or 5% (w/v), in an amount of about 2.8% (w/v) to about 3, 4, or 5% (w/v), in an amount of about 2.9% (w/v) to about 3, 4, or 5% (w/v), in an amount of about 3.0% (w/v) to about 4, or 5% (w/v), in an amount of about 3.1% (w/v) to about 4, or 5% (w/v), in an amount of about 3.2% (w/v) to about 4, or 5% (w/v), in an amount of about 3.3% (w/v) to about 4, or 5% (w/v), in an amount of about 3.4% (w/v) to about 4, or 5% (w/v), in an amount of about 3.5% (w/v) to about 4, or 5% (w/v), in an amount of about 3.6% (w/v) to about 4, or 5% (w/v), in an amount of about 3.7% (w/v) to about 4, or 5% (w/v), in an amount of about 3.8% (w/v) to about 4, or 5% (w/v), in an amount of about 3.9% (w/v) to about 4, or 5% (w/v), in an amount of about 4.0% (w/v) to about 5% (w/v), in an amount of about 4.1% (w/v) to about 5% (w/v), in an amount of about 4.2% (w/v) to about 5% (w/v), in an amount of about 4.3% (w/v) to about 5% (w/v), in an amount of about 4.4% (w/v) to about 5% (w/v), in an amount of about 4.5% (w/v) to about 5% (w/v), in an amount of about 4.6% (w/v) to about 5% (w/v), in an amount of about 4.7% (w/v) to about 5% (w/v), in an amount of about 4.8% (w/v) to about 5% (w/v), or in an amount of about 4.9% (w/v) to about 5% (w/v). The above values may also be determined in % (w/w). Both terms "% (w/v)" and "% (w/w)" are preferably as defined above.

According to another particular preferred embodiment the pharmaceutical composition according to the present invention typically comprises an imidazoquinolin(amine) or a derivative thereof as defined herein, preferably imiquimod or a derivative thereof, in an amount of about 0.1% (w/v) to about 1% (w/v).

According to one further particular preferred embodiment the pharmaceutical composition according to the present invention typically comprises an imidazoquinolin(amine) or a derivative thereof as defined herein, preferably imiquimod or a derivative thereof, in an amount of about 0.005% (w/v) to about 0.5% (w/v), in an amount of about 0.01% (w/v) to about 0.5% (w/v), in an amount of about 0.1% (w/v) to about 0.6% (w/v), in an amount of about 0.2% (w/v) to about 0.7% (w/v), in an amount of about 0.3% (w/v) to about 0.8% (w/v), in an amount of about 0.4% (w/v) to about 0.9% (w/v), in an amount of about 0.5% (w/v) to about 1.0% (w/v), in an amount of about 0.6% (w/v) to about 1.1% (w/v), in an amount of about 0.7% (w/v) to about 1.2% (w/v), in an amount of about 0.8% (w/v) to about 1.3% (w/v), in an amount of about 0.9% (w/v) to about 1.4% (w/v), in an amount of about 1.1% (w/v) to about 1.5% (w/v), in an amount of about 1.2% (w/v) to about 1.6% (w/v), in an amount of about 1.3% (w/v) to about 1.7% (w/v), in an amount of about 1.4% (w/v) to about 1.8% (w/v), in an amount of about 1.5% (w/v) to about 1.9% (w/v), in an amount of about 1.6% (w/v) to about 2.0% (w/v), in an amount of about 1.7% (w/v) to about 2.1% (w/v), in an amount of about 1.8% (w/v) to about 2.2% (w/v), in an amount of about 1.9% (w/v) to about 2.3% (w/v), in an amount of about 2.0% (w/v) to about 2.5% (w/v), in an amount of about 2.1% (w/v) to about 2.6% (w/v), in an amount of about 2.2% (w/v) to about 2.7% (w/v), in an amount of about 2.3% (w/v) to about 2.8% (w/v), in an amount of about 2.4% (w/v) to about 2.9% (w/v), in an amount of about 2.5% (w/v) to about 3.0% (w/v), in an amount of about 2.6% (w/v) to about 3.1% (w/v), in an amount of about 2.7% (w/v) to about 3.2% (w/v), in an amount of about 2.8% (w/v) to about 3.3% (w/v), in an amount of about 2.9% (w/v) to about 3.4% (w/v), in an amount of about 3.0% (w/v) to about 3.5% (w/v), in an amount of about 3.1% (w/v) to about 3.6% (w/v), in an amount of about 3.2% (w/v) to about 3.7% (w/v), in an amount of about 3.3% (w/v) to about 3.8% (w/v), in an amount of about 3.4% (w/v) to about 3.9% (w/v), in an amount of about 3.5% (w/v) to about 4.0% (w/v), in an amount of about 3.6% (w/v) to about 4.1% (w/v), in an amount of about 3.7% (w/v) to about 4.2% (w/v), in an amount of about 3.8% (w/v) to about 4.3% (w/v), in an amount of about 3.9% (w/v) to about 4.4% (w/v), in an amount of about 4.0% (w/v) to about 4.5% (w/v), in an amount of about 4.1% (w/v) to about 4.6% (w/v), in an amount of about 4.2% (w/v) to about 4.7% (w/v), in an amount of about 4.3% (w/v) to about 4.8% (w/v), in an amount of about 4.4% (w/v) to about 4.9% (w/v), or in an amount of about 4.5% (w/v) to about 5.0% (w/v). The above values may also be determined in % (w/w). Both terms "% (w/v)" and "% (w/w)" are preferably as defined above.

For the preparation of the inventive pharmaceutical composition, e.g. when preparing a (stock) solution during preparation of the inventive pharmaceutical composition, however, imidazoquinolin(amine) or a derivative thereof as defined herein may be dissolved in such a (stock) aqueous solution comprising either lactic acid or acetic acid or a mixture of both as defined above typically in a higher concentration as indicated above for the final inventive pharmaceutical composition. For such a purpose, the (stock) solution may comprise an amount of about 0.005% (w/v) or 0.01% (w/v) to about 30% (w/v), preferably an amount of about 1% (w/v) to about 25% (w/v), more preferably an amount of about 5% (w/v) to about 25% (w/v), even more preferably an amount of about 10% (w/v) to about 25% (w/v), and most preferably an amount of about 15% (w/v) to about 20 or 25% (w/v) of imidazoquinolin(amine) or a derivative thereof as defined herein. The above values may alternatively understood as % (w/w). These percentages "% (w/v)" and "% (w/w)" are preferably as defined above.

According to another embodiment, the inventive pharmaceutical composition may also comprise additives or further components. Advantageously, such additives or further components enhance the solubility and/or membrane penetration of the imidazoquinolin(amine) or a derivative thereof as defined herein in the inventive pharmaceutical composition. Alternatively or additionally, such additives or further components allow to provide a more suitable formulation for a specific disease to be treated, confer a better tolerance to the inventive pharmaceutical composition, etc.

According to a particular embodiment, the inventive pharmaceutical composition may comprise cyclodextrines, which are also designated cycloamyloses. As surprisingly found by the inventors of the present invention, cyclodextrines may be used to enhance solubility and, advantageously, membrane penetration of the imidazoquinolin(amine) or a derivative thereof as defined herein in the inventive pharmaceutical composition, even though the imidazoquinolin(amine) or a derivative thereof may not be sufficiently dissolved by just cyclodextrines. In this context, solubility of the imidazoquinolin(amine) or a derivative thereof as defined herein is not only enhanced in the final inventive pharmaceutical composition using cyclodextrines but also in an intermediate (stock) solution formed by imidazoquinolin(amine) or a derivative thereof as defined herein and an organic acid as defined above, e.g. lactic acid, acetic acid or a mixture thereof. Particularly, it was an unexpected finding in view of the prior art knowledge that cyclodextrin in combination with lactic acid and/or acetic acid leads to a small, but significant increment of the solubility of imidazoquinolin(amine) or a derivative thereof, particularly of imiquimod, of at least 10%, more preferably of at least 15% or at least about 18% compared to the solubility of that therapeutically active agent in combination with lactic acid alone. Accordingly, cyclodextrines may be used in any stage of preparation of the pharmaceutical composition to enhance the solubility of the imidazoquinolin(amine) or a derivative thereof as defined herein. In the context of the present invention, cyclodextrines are preferably understood as members of a family of cyclic oligosaccharides, composed of 5 or more α-D-glucopyranoside units linked between positions 1 and 4, as known for amylose, a fragment of starch. In the context of the present invention, cyclodextrines particularly comprise α-cyclodextrins, which form six membered sugar ring molecules, β-cyclodextrins, which form, seven sugar ring molecules, γ-cyclodextrins, which form eight sugar ring molecules, δ-cyclodextrins and ε-cyclodextrins. Particularly preferably, the inventive pharmaceutical composition comprises α-cyclodextrins, β-cyclodextrins, and/or γ-cyclodextrins, even more preferably, β-cyclodextrins, such as hydroxypropyl-β-cyclodextrin (HP-β-CD).

Surprisingly, the incorporation of HPβCD in the inventive pharmaceutical formulation improved the physical stability, achieving a clear homogeneous solution.

According to a particularly preferred embodiment, the inventive pharmaceutical composition as defined above may comprise cyclodextrines as defined above in an amount of about 0.1% (w/v) to about 30% (w/v), typically in an amount of about 1% (w/v) to about 20% (w/v), preferably in an amount of about 2% (w/v) to about 20% (w/v), more preferably in an amount of about 5% (w/v) to about 20% (w/v), even more preferably in an amount of about 5% (w/v) to about 15% (w/v), and most preferably in an amount of about 10% (w/v) to about 15% (w/v), or in an amount of about 0.1% (w/v) to about 4% (w/v), 0.1 to 2%, more preferably in an amount of 0.5 to 2% or, alternatively, in an amount of about 2% (w/v) to about 6% (w/v), in an amount of about 4% (w/v) to about 8% (w/v), in an amount of about 6% (w/v) to about 10% (w/v), in an amount of about 8% (w/v) to about 12% (w/v), in an amount of about 10% (w/v) to about 14% (w/v), in an amount of about 12% (w/v) to about 16% (w/v), in an amount of about 14% (w/v) to about 18% (w/v), in an amount of about 16% (w/v) to about 20% (w/v), in an amount of about 18% (w/v) to about 22% (w/v), in an amount of about 20% (w/v) to about 24% (w/v), in an amount of about 22% (w/v) to about 26% (w/v), in an amount of about 24% (w/v) to about 28% (w/v), or in an amount of about 26% (w/v) to about 30% (w/v), wherein the amounts as defined in % (w/v) may either be understood to be based on the weight of the cyclodextrine with respect to the total volume of the inventive pharmaceutical composition or an intermediate stock solution, when e.g. provided as a liquid or semi-liquid formulation. Alternatively, the above amounts may be defined in % (w/w), wherein the amount as defined in % (w/w) may either be determined on the basis of the weight of the cyclodextrine with respect to the total weight of the inventive pharmaceutical composition or on the basis of an intermediate stock solution.

According to a another particularly preferred embodiment, the inventive pharmaceutical composition as defined above may comprise cyclodextrines as defined above in an amount of about 2% (w/v) to about 6% (w/v), e.g. of about 2.5% (w/v) to about 6% (w/v), of about 3% (w/v) to about 6% (w/v), of about 3.5% (w/v) to about 6% (w/v), of about 4% (w/v) to about 6% (w/v), of about 4.5% (w/v) to about 6% (w/v), or of about 2.5% (w/v) to about 5.5% (w/v), about 3% (w/v) to about 5.5% (w/v), of about 3.5% (w/v) to about 5.5% (w/v), of about 4% (w/v) to about 5.5% (w/v), of about 4.5% (w/v) to about 5.5% (w/v), or of about 5% (w/v).

According to another particularly preferred embodiment, particularly for certain administration forms and applications, the pharmaceutical composition according to the present invention further comprises at least one thermo-sensitive agent. In the context of the present invention, the term "thermo-sensitive agent" typically refers to a compound, preferably a polymer, which is able to change its state of aggregation or its viscosity at a defined point of transition (cooperative transition) from a liquid or semi-liquid state into a solid or semi solid state, preferably to a solid state. More preferably the term "thermo-sensitive agent" typically refers to a compound, preferably a(n) (organic) polymer, which is able to change its state of aggregation from a liquid or semi-liquid state into a solid or semi solid state (e.g. from a liquid to a gel-like state or to a solid state) at a specific point of transition (also called "lower critical solution temperature" (LCST) or "gel transition temperature"), wherein the specific point of transition is preferably defined by a specific transition temperature in a range of about 15° C. to about 35° C., more preferably in a range of about 15° C. to about 30° C., even more preferably in a range of about 15 or 20° C. to about 30° C., most preferably in a range of about 15 or 20° C. to about 25° C. The "lower critical solution temperature" according to the present invention is measured at ambient pressure and depends on the molar-mass distribution if the thermo-sensitive agent. Preferably, such a thermo-sensitive agent as defined above allows an in situ gel formation of the thermo-sensitive agent and any compound or composition formulated therewith, e.g. the inventive pharmaceutical composition at body temperature, whereas the pharmaceutical composition will typically display (semi)liquid properties. In this context, an in situ gel formation of the thermo-sensitive agent and any compound or composition formulated therewith typically occurs directly upon or directly subsequent to administration of the inventive pharmaceutical composition to the site of affliction of the patient to be treated, i.e. not prior to administration of the inventive pharmaceutical composition. Such an in situ gel formation is in particular advantageous for specific applications, which are intended to release imidazoquinolin(amine) or a derivative thereof of the inventive pharmaceutical composition as defined herein over an extended period of time. Such applications are usually directed to place the formulation in a body cavity, e.g. of a tissue or organ, such as the bladder, and may therefore be particularly suitable for, e.g., vesical administration in the therapy of bladder diseases.

One particular advantage of a pharmaceutical composition of the present invention comprising thermo-sensitive agents is the ease of its administration due to selection of a transition point at a temperature range as defined above. More specifically, the selection of a transition point at a temperature range as defined above allows not only for preparation or storage of the inventive pharmaceutical composition in a liquid or semi-liquid aggregate state. It also allows for administration of the (preferably liquid) inventive pharmaceutical composition by e.g. injection, since the inventive pharmaceutical composition directly solidifies or undergoes gelation subsequent to administration due to the increased temperature of the surrounding tissue or organ, which is preferably higher than the temperature of the transition point. Accordingly, gel formation is induced within the tissue or organ. Administration thereby may be carried out using non-invasive methods (without surgery), such as an injection needle having a cannula of a suitable diameter, an injection tube, endoscopic methods, etc. Furthermore, such gel formation results in increased bioadhesive properties of the inventive pharmaceutical composition of the present invention leading to a prolonged exposure of the imidazoquinolin(amine) or a derivative thereof of the inventive pharmaceutical composition to TLR7-expressing cells and less systemic drug penetration. As mentioned above, the exposure of imidazoquinolin(amine) or a derivative thereof to TLR7-expressing cells induces an immunological response exerting the desired therapeutic effect.

Additionally, the pharmaceutical compositions of the present invention comprising thermo-sensitive agents advantageously avoids or at least significantly reduces systemic side effects of imidazoquinolin(amine) or a derivative thereof due to local administration at the site of affliction, increased in vivo viscosity of the inventive pharmaceutical composition, reduced diffusion of the biologically active agent to surrounding tissues, and, in addition, in some cases also due to increased bioadhesive properties.

Finally, the pharmaceutical compositions of the present invention comprising thermo-sensitive agents advantageously allow for a so called "extended release" (or sometimes termed "long term release") of the imidazoquinolin(amine) or a derivative thereof contained therein. Particularly, the gel formation of the inventive pharmaceutical composition results in a sustained drug release of imidazoquinolin(amine) or a derivative thereof in a zero-order kinetic which enhances the duration of the therapeutic effect. Such prolonged therapeutic effect of the imidazoquinolin(amine) or a derivative thereof contained in the inventive pharmaceutical composition also avoids repeated administration of the inventive pharmaceutical composition, particularly in short time intervals, which typically cannot be avoided when using pharmaceutical compositions without exhibiting sustained drug release. The depot effect of a pharmaceutical composition of the invention typically lasts at least 24 h, more preferably 48 h, more preferably at least 7 days, typically releasing the active agent in app. constant amounts over time (e.g. comparable release amounts within 24 h on e.g day 2 and day 8 after administration).

According to a specific preferred embodiment, the inventive pharmaceutical composition as defined above contains a thermo-sensitive agent as defined herein in an amount of about 0.1% (w/v) to about 40% (w/v), preferably between 0.1 and 5% (more preferably 0.1. and 2%) or, alternatively, typically in an amount of about 2% (w/v) to about 30% (w/v), preferably in an amount of about 5% (w/v) to about 30% (w/v), more preferably in an amount of about 10% (w/v) to about 30% (w/v), and most preferably in an amount of about 10% (w/v) to about 25% (w/v), e.g. in an amount of about 0.1% (w/v) to about 10% (w/v), in an amount of about 5% (w/v) to about 15% (w/v), in an amount of about 10% (w/v) to about 20% (w/v), in an amount of about 11% (w/v) to about 20% (w/v), in an amount of about 12% (w/v) to about 20% (w/v), in an amount of about 13% (w/v) to about 20% (w/v), in an amount of about 14% (w/v) to about 20% (w/v), in an amount of about 15% (w/v) to about 20% (w/v), in an amount of about 16% (w/v) to about 20% (w/v), in an amount of about 10% (w/v) to about 19% (w/v), in an amount of about 10% (w/v) to about 18% (w/v), in an amount of about 10% (w/v) to about 17% (w/v), in an amount of about 10% (w/v) to about 16% (w/v), in an amount of about 11% (w/v) to about 19% (w/v), in an amount of about 11% (w/v) to about 18% (w/v), in an amount of about 11% (w/v) to about 17% (w/v), in an amount of about 11% (w/v) to about 16% (w/v), in an amount of about 12% (w/v) to about 19% (w/v), in an amount of about 12% (w/v) to about 18% (w/v), in an amount of about 12% (w/v) to about 17% (w/v), in an amount of about 12% (w/v) to about 16% (w/v), in an amount of about 13% (w/v) to about 19% (w/v), in an amount of about 13% (w/v) to about 18% (w/v), in an amount of about 13% (w/v) to about 17% (w/v), in an amount of about 13% (w/v) to about 16% (w/v), in an amount of about 14% (w/v) to about 19% (w/v), in an amount of about 14% (w/v) to about 18% (w/v), in an amount of about 14% (w/v) to about 17% (w/v), in an amount of about 14% (w/v) to about 16% (w/v), in an amount of about 15% (w/v) to about 19% (w/v), in an amount of about 15% (w/v) to about 18% (w/v), in an amount of about 15% (w/v) to about 17% (w/v), in an amount of about 15% (w/v) to about 16% (w/v), in an amount of about 15% (w/v) to about 25% (w/v), in an amount of about 20% (w/v) to about 30% (w/v), in an amount of about 25% (w/v) to about 35% (w/v), or in an amount of about 30% (w/v) to about 40% (w/v), wherein the amounts as defined in % (w/v) may either be understood to be given on the basis of the weight of the thermo-sensitive agent as defined herein with respect to the total volume of the inventive pharmaceutical composition or an intermediate stock solution, when e.g. provided as a liquid or semi-liquid formulation. Alternatively, the above amounts may be defined in % (w/w), wherein the amount as defined in % (w/w) may either be understood to be based on the weight of the thermo-sensitive agent as defined herein with respect to the total weight of the inventive pharmaceutical composition.

According to another preferred embodiment of the present invention, the pharmaceutical composition comprises an imidazoquinolin(amine), at least one organic acid selected from acetic acid and/or lactic acid and at least one thermo-sensitive agent, wherein the at least one thermo-sensitive agent is preferably selected from chitosan or its derivatives, or from a poly(ethylene oxide)-poly(propylene oxide)-poly(ethylene oxide) copolymer (also termed PEO-PPO-PEO or poloxamer).

According to one preferred embodiment, the inventive pharmaceutical composition as defined above contains as a thermo-sensitive agent a chitosan or a derivate thereof. In the context of the present invention such a chitosan is preferably understood as a linear polysaccharide composed of randomly distributed β-(1-4)-linked D-glucosamine (deacetylated unit) and of N-acetyl-D-glucosamine (acetylated unit). Chitosan is typically produced commercially by deacetylation of chitin, which is the structural element in the exoskeleton of crustaceans such as crabs, shrimps, etc. The degree of deacetylation (% DA) is typically determined by NMR spectroscopy, wherein the % DA in commercial chitosans is typically in the range 60-100%. Chitosans in the context of the present invention furthermore include derivatives thereof such as trimethylchitosan, wherein the amino group of chitosan has been trimethylated or oligomeric derivatives (3-6 kDa) of chitosans.

According to one further more preferred embodiment, the inventive pharmaceutical composition as defined above contains as a thermo-sensitive agent a poloxamer. Poloxamers, solubilised at relatively high concentrations (>17.5%) in water, are able to produce systems that are liquid at low temperature (below room temperature) and that form jelly-like, semi-solid or solid structures or gels at elevated temperatures. Poloxamers are commercially available under the trade name Pluronic and Lutrol (BASF AG, Ludwigshafen, Germany). Poloxamers are present in many marketed pharmaceutical products as solubilizers, surfactants, viscosizing and jellifying agents. In this context, the inventive pharmaceutical composition preferably does not comprise any further components exhibiting surfactant properties apart from such thermo-sensitive components, e.g. poloxamers, which additionally exhibit surfactant properties.

Pharmaceutical compositions according to the present invention comprising a thermo-sensitive agent are particularly advantageous. For instance, intravesical application of pharmaceutical compositions according to the present invention comprising a thermo-sensitive agent, such as for instance, poloxamer avoids systemic absorption, and, in addition, provides an increase of the local contact of imidazoquinoline(amine) to the urothelium. Thus, addition of a thermo-sensitive agent reduces systemic absorption of imidazoquinoline(amine) from bladder urothelium with sustained local infiltration of immune cells.

Poloxamers in the context of the present invention are typically to be understood as a poly(ethylene oxide)-poly (propylene oxide)-poly(ethylene oxide) copolymer, also abbreviated "PEO-PPO-PEO". Such poloxamers are therefore nonionic triblock copolymers composed of a central hydrophobic chain of polyoxypropylene (poly(propylene oxide)) flanked by two hydrophilic chains of polyoxyethylene (poly(ethylene oxide)). The molecular weight of such poloxamers is generally not specifically defined and may be varied suitably for each specific purpose. Because the lengths of the polymer blocks can be customized, a multitude of poloxamers may be provided having slightly different properties. For the generic term "poloxamer", these copolymers are commonly named with the letter "P" (for poloxamer) followed by three digits, the first two digits×100 give the approximate molecular mass of the polyoxypropylene core, and the last digit×10 gives the percentage polyoxyethylene content (e.g., P407=Poloxamer with a polyoxypropylene molecular mass of 4,000 g/mol and a 70% polyoxyethylene content). For the Pluronic/Lutrol tradename, coding of these copolymers starts with a letter to define its physical form at room temperature (L=liquid, P=paste, F=flake (solid)) followed by two or three digits. The first digit (two digits in a three-digit number) in the numerical designation, multiplied by 300, indicates the approximate molecular weight of the hydrophobe; and the last digit×10 gives the percentage polyoxyethylene content (e.g., L61=Pluronic with a polyoxypropylene molecular mass of 1,800 g/mol and a 10% polyoxyethylene content). In the example given, poloxamer 181 (P181)=Pluronic L61.

Poloxamers suitable for the inventive pharmaceutical composition as a thermo-sensitive agent preferably comprise any poly(ethylene oxide)-poly(propylene oxide)-poly(ethylene oxide) copolymer or mixture of such copolymers suitable for the inventive purpose, i.e. any PEO-PPO-PEO polymer or mixture of such copolymers exhibiting thermo-sensitive properties as defined above. Such PEO-PPO-PEO polymers include also commercially available PEO-PPO-PEO polymers and mixtures thereof, e.g. Pluronic F 108 Cast Solid Surfacta; Pluronic F 108 Pastille; Pluronic F 108 Prill; Pluronic F 108NF Prill (Poloxamer 338); Pluronic F 127; Pluronic F 127 Prill; Pluronic F 127 NF; Pluronic F 127 NF 500 BHT Prill; Pluronic F 127 NF Prill (Poloxamer 407); Pluronic F 38; Pluronic F 38 Pastille; Pluronic F 68; Pluronic F 68 Pastille; Pluronic F 68 LF Pastille; Pluronic F 68 NF Prill (Poloxamer 188); Pluronic F 68 Prill; Pluronic F 77; Pluronic F 77 Micropastille; Pluronic F 87; Pluronic F 87 NF Prill (Poloxamer 237); Pluronic F 87 Prill; Pluronic F 88 Pastille; Pluronic F 88 Prill; Pluronic F 98; Pluronic F 98 Prill; Pluronic L 10; Pluronic L 101; Pluronic L 121; Pluronic L 31; Pluronic L 35; Pluronic L 43; Pluronic L 44; Pluronic L 44 NF (Poloxamer 124); Pluronic L 61; Pluronic L 62; Pluronic L 62 LF; Pluronic L 62D; Pluronic L 64; Pluronic L 81; Pluronic L 92; Pluronic L44 NF INH surfactant (Poloxamer 124); Pluronic N 3; Pluronic P 103; Pluronic P 104; Pluronic P 105; Pluronic P 123 Surfactant; Pluronic P 65; Pluronic P 84; Pluronic P 85; and Poloxamer 403. Such PEO-PPO-PEO polymers furthermore include mixtures formed by any two or more (3, 4, 5, 6, etc.) of these PEO-PPO-PEO polymers.

More preferably, poloxamers suitable for the inventive pharmaceutical composition as a thermo-sensitive agent include poloxamers or mixtures thereof, the poloxamers selected from Poloxamer 124, Poloxamer 188, Poloxamer 237, Poloxamer 338, Poloxamer 403, and Poloxamer 407. Thus, using the poloxamer coding labels of BASF, suitable poloxamers are selected from Pluronic/Lutrol F 44 (poloxamer 124), Pluronic/Lutrol F 68 (poloxamer 188), Pluronic/Lutrol F 87 (poloxamer 237), Pluronic/Lutrol F 108 (poloxamer 338), Pluronic/Lutrol F 123 (poloxamer 403), Pluronic/Lutrol F 127 (poloxamer 407).

Even more preferably, poloxamers suitable for the inventive pharmaceutical composition as a thermo-sensitive agent include poloxamers or mixtures thereof, the poloxamers selected from Poloxamer 188, Poloxamer 403, and Poloxamer 407.

Among the different PEO-PPO-PEO polymers suitable for the inventive pharmaceutical composition as a thermo-sensitive agent, Poloxamer 407 is most preferably selected and represents the first choice-polymer for the production of thermo-responsive gels within the context of the present invention. Poloxamer 407 as a thermo-sensitive agent may be used either alone or in admixture with other poloxamers as described above, preferably with Poloxymer 188, to produce a mixture of thermo-sensitive agents that "jellify" at a selected temperature, preferably slightly above room temperature (>20° C.), but below the body temperature (<37° C.).

According to one particularly preferred embodiment, the inventive pharmaceutical composition comprises as a thermo-sensitive agent Poloxamer 407 in an amount as defined above in general for thermo-sensitive agents, more preferably in an amount of about 0.1, 1, 2, 3, 4, 5, 6, 7, 8, 9 or 10% (w/v) to about 30% (w/v), even more preferably in an amount of about 5% (w/v) to about 25% (w/v), and most preferably in an amount of about 10% (w/v) to about 25% (w/v), e.g. in an amount of about 0.1, 1, 2, 3, 4, 5, 6, 7, 8, 9 or 10% (w/v) to about 25% (w/v), in an amount of about 10.5% (w/v) to about 25% (w/v), in an amount of about 11% (w/v) to about 25% (w/v), in an amount of about 11.5% (w/v) to about 25% (w/v), in an amount of about 12% (w/v) to about 25% (w/v), in an amount of about 12.5% (w/v) to about 25% (w/v), in an amount of about 13% (w/v) to about 25% (w/v), in an amount of about 13.5% (w/v) to about 25% (w/v), in an amount of about 14% (w/v) to about 25% (w/v), in an amount of about 14.5% (w/v) to about 25% (w/v), in an amount of about 15% (w/v) to about 25% (w/v), in an amount of about 15.5% (w/v) to about 25% (w/v), in an amount of about 16% (w/v) to about 25% (w/v), in an amount of about 16.5% (w/v) to about 25% (w/v), in an amount of about 17% (w/v) to about 25% (w/v), in an amount of about 17.5% (w/v) to about 25% (w/v), in an amount of about 18% (w/v) to about 25% (w/v), in an amount of about 18.5% (w/v) to about 25% (w/v), in an amount of about 19% (w/v) to about 25% (w/v), in an amount of about 19.5% (w/v) to about 25% (w/v), in an amount of about 20% (w/v) to about 25% (w/v), in an amount of about 20.5% (w/v) to about 25% (w/v), in an amount of about 21% (w/v) to about 25% (w/v), in an amount of about 21.5% (w/v) to about 25% (w/v), in an amount of about 22% (w/v) to about 25% (w/v), in an amount of about 22.5% (w/v) to about 25% (w/v), in an amount of about 23% (w/v) to about 25% (w/v), in an amount of about 23.5% (w/v) to about 25% (w/v), in an amount of about 24% (w/v) to about 25% (w/v), or in an amount of about 24.5% (w/v) to about 25% (w/v), or more particularly in an amount of about 12% (w/v) to about 25% (w/v), in an amount of about 13% (w/v) to about 25% (w/v), in an amount of about 14% (w/v) to about 25% (w/v), in an amount of about 15% (w/v) to about 25% (w/v), in an amount of about 16% (w/v) to about 25% (w/v), in an amount of about 17% (w/v) to about 25% (w/v), in an amount of about 18% (w/v) to about 25% (w/v), in an amount of about 19% (w/v) to about 25% (w/v), in an amount of about 20% (w/v) to about 25% (w/v), in an amount of about 21% (w/v) to about 25% (w/v), in an amount of about 22% (w/v) to about 25% (w/v), in an amount of about 23% (w/v) to about 25% (w/v), in an amount of about 24% (w/v) to about 25% (w/v), or more particularly in an amount of about 12% (w/v) to about 24% (w/v), in an amount of about 12% (w/v) to about 23% (w/v), in an amount of about 12% (w/v) to about 22% (w/v), in an amount of about 12% (w/v) to about 21% (w/v), in an amount of about 12% (w/v) to about 20% (w/v), in an amount of about 12% (w/v) to about 19% (w/v), in an amount of about 12% (w/v) to about 18% (w/v), in an amount of about 12% (w/v) to about 17% (w/v), in an amount of about 12% (w/v) to about 16% (w/v), or more particularly in an amount of about 13% (w/v) to about 24% (w/v), in an amount of about 13% (w/v) to about 23% (w/v), in an amount of about 13% (w/v) to about 22% (w/v), in an amount of about 13% (w/v) to about 21% (w/v), in an amount of about 13% (w/v) to about 20% (w/v), in an amount of about 13% (w/v) to about 19% (w/v), in an amount of about 13% (w/v) to about 18% (w/v), in an amount of about 13% (w/v) to about 17% (w/v), in an amount of about 13% (w/v) to about 16% (w/v), or more particularly in an amount of about 14% (w/v) to about 24% (w/v), in an amount of about 14% (w/v) to about 23% (w/v), in an amount of about 14% (w/v) to about 22% (w/v), in an amount of about 14% (w/v) to about 21% (w/v), in an amount of about 14% (w/v) to about 20% (w/v), in an amount of about 14% (w/v) to about 19% (w/v), in an amount of about 14% (w/v) to about 18% (w/v), in an amount of about 14% (w/v) to about 17% (w/v), in an amount of about 14% (w/v) to about 16% (w/v), or more particularly in an amount of about 15% (w/v) to about 24% (w/v), in an amount of about 15% (w/v) to about 23% (w/v), in an amount of about 15% (w/v) to about 22% (w/v), in an amount of about 15% (w/v) to about 21% (w/v), in an amount of about 15% (w/v) to about 20% (w/v), in an amount of about 15% (w/v) to about 19% (w/v), in an amount of about 15% (w/v) to about 18% (w/v), in an amount of about 15% (w/v) to about 17% (w/v), in an amount of about 15% (w/v) to about 16% (w/v), or more particularly in an amount of about 24% (w/v) to about 25% (w/v), wherein the amounts as defined in % (w/v) may either be understood to be based on the weight of the thermo-sensitive agent as defined herein with respect to the total volume of the inventive pharmaceutical composition or an intermediate stock solution, when e.g. provided as a liquid or semi-liquid formulation. Alternatively, the above amounts may be defined in % (w/w), wherein the amount as defined in % (w/w) may either be understood to be based on the weight of the thermo-sensitive agent as defined herein with respect to the total weight of the inventive pharmaceutical composition.

According to a further preferred embodiment, the inventive pharmaceutical composition may comprise as a thermo-sensitive agent any of the poloxamers as defined above, preferably any of the poloxamers selected from Poloxamer 124, Poloxamer 188, Poloxamer 237, Poloxamer 338, and Poloxamer 403. Such poloxamers are preferably present in the inventive pharmaceutical composition as a thermo-sensitive agent in amounts as described above for thermo-sensitive agents in general or more specifically as described above for Poloxamer 407.

According to a particularly preferred embodiment, the inventive pharmaceutical composition may also comprise as a thermo-sensitive agent a mixture of any of the thermo-sensitive agents as defined above. Such a mixture of thermo-sensitive agents preferably comprises an overall amount of the thermo-sensitive agent of such a mixture similar as described above in general for thermo-sensitive agents or more specifically as described above for Poloxamer 407. Furthermore, such a mixture of thermo-sensitive agents preferably comprises a ratio of the different poloxamers, which leads to a mixture of thermo-sensitive agents that "jellifies" at a desired temperature, preferably at a temperature range as defined above. In this context, the ratio and/or the amount of different poloxamers in the mixture may influence the "Lower Critical Solution Temperature" (LCST) and thus the gel transition temperature. For example, it has been found that decreasing the percentage of Poloxamer 407 in an admixture with Poloxamer 188 results in an increase of the LCST. Furthermore, the amount and/or ratio of the different poloxamers in the mixture is preferably selected with respect to the drug solubility. Preferably, any of two of the thermo-sensitive agents as defined above, particularly when provided in an amount as defined above, may be contained in the inventive pharmaceutical composition as a mixture in a ratio of about 1:20 to about 20:1, preferably in a ratio of about 1:20, 2:20, 3:30, 4:20, 5:20, 6:20, 7:20, 8:20, 9:20, 10:20, 11:20, 12:20, 13:20, 14:20, 15:20, 16:20, 17:20, 18:20, 19:20, 20:20 (=1:1), or in a ratio of about 20:20, 19:20, 18:20, 17:20, 16:20, 15:20, 14:20, 13:20, 12:20, 11:20, 10:20, 9:20, 8:20, 7:20, 6:20, 5:20, 4:20, 3:20, 2:20, or about 1:20, or in a ratio of about 1:20, 1:19, 2:18, 3:17, 4:16, 5:15, 6:14, 7:13, 8:12, 9:11, 10:10 (1:1), 11:9, 12:8, 13:7, 14:6, 15:5, 16:4, 17:3, 18:2, 19:1 or 20:1, or in a range formed by any of two of the ratio values as defined above. Even more preferably, any of two of the thermo-sensitive agents as defined above, particularly when provided in an amount as defined above, may be contained in the inventive pharmaceutical composition as a mixture in a range of about 1:10 to about 10:1, e.g. in a ratio of about 1:10, 2:10, 3:10, 4:10, 5:10, 6:10, 7:10, 8:10, 9:10, or 10:10 (i.e. 1:1), or in a ratio of about 10:9, 10:8, 10:7, 10:6, 10:5, 10:4, 10:3, 10:2, or 10:1, or in a range formed by any of two of the ratio values as defined above.

Even more preferably, the inventive pharmaceutical composition may comprise as a thermo-sensitive agent a mixture of Poloxamer 407 and any of the above described poloxamers, even more preferably selected from Poloxamer 124, Poloxamer 188, Poloxamer 237, Poloxamer 338, and Poloxamer 403. Likewise, such a mixture of thermo-sensitive agents preferably comprises an overall amount of the thermo-sensitive agents of the mixture similar as described above in general for thermo-sensitive agents or more specifically as described above for Poloxamer 407.

According to a particularly preferred embodiment, the inventive pharmaceutical composition may comprise as a thermo-sensitive agent a mixture of Poloxamer 407 and Poloxamer 188. Preferably such a mixture of Poloxamer 407 and Poloxamer 188 is contained in the inventive pharmaceutical composition in an overall amount as described above in general for thermo-sensitive agents or more specifically as described above for Poloxamer 407. Preferably such a mixture of Poloxamer 407 and Poloxamer 188 also occurs in the inventive pharmaceutical composition in a ratio as described above in general for mixtures of polyoxamers used as a thermo-sensitive agent in the inventive pharmaceutical composition. Even more preferably, such a ratio is selected from a ratio of Poloxamer 407:Poloxamer 188 of about 1:20, 1:19, 2:18, 3:17, 4:16, 5:15, 6:14, 7:13, 8:12, 9:11, 10:10 (1:1), 11:9, 12:8, 13:7, 14:6, 15:5, 16:4, 17:3, 18:2, 19:1 or 20:1, or a ratio formed by any of two of the values as defined above. Most preferably, such a ratio is selected from a ratio of Poloxamer 407:Poloxamer 188 of about 7:3, 7.5:2.5, 8:2, 8.5:1.5, 9:1, or 9.5:0.5, or a ratio formed by any of two of these values. Accordingly, the absolute content of Poloxamer 188 and of Poloxamer 407 in the inventive pharmaceutical composition may be determined on basis of the overall amount and on the specific ratio of both poloxamers in the inventive pharmaceutical composition.

According to a specific embodiment, the inventive pharmaceutical composition may comprise as a thermo-sensitive agent Poloxamer 407 in an (overall) amount of about 17.5% (w/v)/(w/w) to about 22.5% (w/v)/(w/w), more preferably in an overall amount of about 17.5% (w/v)/(w/w), of about 18.0% (w/v)/(w/w), of about 18.5% (w/v)/(w/w), of about 19.0% (w/v)/(w/w), of about 19.5% (w/v)/(w/w), of about 20.0% (w/v)/(w/w), of about 20.5% (w/v)/(w/w), of about 21.0% (w/v)/(w/w), of about 21.5% (w/v)/(w/w), of about 22.0% (w/v)/(w/w), or of about 22.5% (w/v)/(w/w), or in an (overall) amount of about 10% (w/v)/(w/w) to about 22.5% (w/v)/(w/w), more preferably in an overall amount of about 11% (w/v)/(w/w) to about 22.5% (w/v)/(w/w), of about 12.0% (w/v)/(w/w) to about 22.5% (w/v)/(w/w), of about 13% (w/v)/(w/w) to about 22.5% (w/v)/(w/w), of about 14.0% (w/v)/(w/w) to about 22.5% (w/v)/(w/w), of about 15.0% (w/v)/(w/w) to about 22.5% (w/v)/(w/w), of about 15.5% (w/v)/(w/w) to about 22.5% (w/v)/(w/w), of about 16.0% (w/v)/(w/w) to about 22.5% (w/v)/(w/w), or of about 11% (w/v)/(w/w) to about 20.0% (w/v)/(w/w), of about 12.0% (w/v)/(w/w) to about 20.0% (w/v)/(w/w), of about 13% (w/v)/(w/w) to about 20.0% (w/v)/(w/w), of about 14.0% (w/v)/(w/w) to about 20.0% (w/v)/(w/w), of about 15.0% (w/v)/(w/w) to about 20.0% (w/v)/(w/w), of about 15.5% (w/v)/(w/w) to about 20.0% (w/v)/(w/w), of about 16.0% (w/v)/(w/w) to about 20.0% (w/v)/(w/w), or of about 11% (w/v)/(w/w) to about 19.0% (w/v)/(w/w), of about 12.0% (w/v)/(w/w) to about 19.0% (w/v)/(w/w), of about 13% (w/v)/(w/w) to about 19.0% (w/v)/(w/w), of about 14.0% (w/v)/(w/w) to about 19.0% (w/v)/(w/w), of about 15.0% (w/v)/(w/w) to about 19.0% (w/v)/(w/w), of about 15.5% (w/v)/(w/w) to about 19.0% (w/v)/(w/w), of about 16.0% (w/v)/(w/w) to about 19.0% (w/v)/(w/w), or of about 11% (w/v)/(w/w) to about 18.0% (w/v)/(w/w), of about 12.0% (w/v)/(w/w) to about 18.0% (w/v)/(w/w), of about 13% (w/v)/(w/w) to about 18.0% (w/v)/(w/w), of about 14.0% (w/v)/(w/w) to about 18.0% (w/v)/(w/w), of about 15.0% (w/v)/(w/w) to about 18.0 (w/v)/(w/w), of about 15.5% (w/v)/(w/w) to about 18.0% (w/v)/(w/w), of about 16.0% (w/v)/(w/w) to about 18.0% (w/v)/(w/w), or of about 11% (w/v)/(w/w) to about 17.0% (w/v)/(w/w), of about 12.0% (w/v)/(w/w) to about 17.0% (w/v)/(w/w), of about 13% (w/v)/(w/w) to about 17.0% (w/v)/(w/w), of about 14.0% (w/v)/(w/w) to about 17.0% (w/v)/(w/w), of about 15.0% (w/v)/(w/w) to about 17.0% (w/v)/(w/w), of about 15.5% (w/v)/(w/w) to about 17.0% (w/v)/(w/w), of about 16.0% (w/v)/(w/w) to about 17.0% (w/v)/(w/w), or of about 11% (w/v)/(w/w) to about 16.5% (w/v)/(w/w), of about 12.0% (w/v)/(w/w) to about 16.5% (w/v)/(w/w), of about 13% (w/v)/(w/w) to about 16.5% (w/v)/(w/w), of about 14.0% (w/v)/(w/w) to about 16.5% (w/v)/(w/w), of about 15.0% (w/v)/(w/w) to about 16.5% (w/v)/(w/w), of about 15.5% (w/v)/(w/w) to about 16.5% (w/v)/(w/w). (The term (w/v)/(w/w) means either (w/v) or (w/w)) or any range formed by any of two of these values as defined above.

According to a further specific embodiment, the inventive pharmaceutical composition may comprise as a thermo-sensitive agent a mixture of Poloxamer 407 and Poloxamer 188 in an overall amount of about 22.5% (w/v)/(w/w) to about 27.5% (w/v)/(w/w), more preferably in an overall amount of about 25% (w/v)/(w/w), and preferably in a ratio of Poloxamer 407:Poloxamer 188 of about 15:5, 16:4, 17:3, 18:2, 19:1 or 20:1, or a ratio formed by any of two of these values, more preferably in a ratio of about 9.5:0.5, of about 9:1, of about 8.5:1.5, or of about 8:2, or a ratio formed by any of two of these values. Accordingly, when the inventive pharmaceutical composition comprises a mixture of Poloxamer 407 and Poloxamer 188, Poloxamer 407 may be present in the inventive pharmaceutical composition in an amount of about 15.5% (w/v)/(w/w) to about 26.5% (w/v)/(w/w), preferably in an amount of about 17.5% (w/v)/(w/w) to about 22.5% (w/v)/(w/w), whereas Poloxamer 188 may be present in the pharmaceutical composition in an amount of about 1.0% (w/v)/(w/w) to about 6.0% (w/v)/(w/w), preferably in an amount of about 2.5% (w/v)/(w/w) to about 4.5% (w/v)/(w/w). (The term (w/v)/(w/w) means either (w/v) or (w/w)).

The inventive pharmaceutical composition may furthermore comprise additives or further components, such as e.g. cyclodextrin as defined above. In this context, the content of additives, particularly cyclodextrin, may have an influence on above defined so called "lower critical solution temperature" (LCST) or "gel transition temperature. As a particular example, increasing percentages of cyclodextrin result in an increase of LCST of Poloxamer 407 or a mixture of Poloxamer 407 and Poloxamer 188 as defined above. This may suitable applied to other poloxamers as defined above and to other thermo-sensitive agents as defined herein.

Likewise, the LCST of the pharmaceutical compositions of the present invention are differently influenced by acetic acid and lactic acid. Both acids generally increase the LCST of the compositions. However, while e.g. imiquimod does not influence at all the gel transition temperature of inventive pharmaceutical compositions comprising only acetic acid, the LCST of compositions comprising lactic acid is enhanced. Thus, the final percentage of thermo-sensitive agents as defined herein may depend on the used acid and whether cyclodextrin is present or not.

According to a further embodiment, the pharmaceutical composition according to the invention may further comprise a pharmaceutically acceptable carrier and/or vehicle. In the context of the present invention, a pharmaceutically acceptable carrier typically includes a liquid basis of the inventive pharmaceutical composition, e.g. pyrogen-free water; the free water solution may be combined in any appropriate ratio with a water-miscible, pharmaceutically acceptable organic solvent, e.g. an alcohol (e.g. ethanol or isipropanol); the following may also be used: isotonic saline or buffered (aqueous) solutions, e.g phosphate, citrate, etc. buffered solutions, an aqueous buffered solution, containing e.g. a sodium salt, preferably at least 50 mM of a sodium salt, a calcium salt, preferably at least 0.01 mM of a calcium salt, and/or a potassium salt, preferably at least 3 mM of a potassium salt. According to a preferred embodiment, the sodium, calcium and/or potassium salts may occur in the form of their halogenides, e.g. chlorides, iodides, or bromides, in the form of their hydroxides, carbonates, hydrogen carbonates, or sulfates, etc. Without being limited thereto, examples of sodium salts include e.g. NaCl, NaI, NaBr, $Na_2CO_3$, $NaHCO_3$, $Na_2SO_4$, examples of the optional potassium salts include e.g. KCl, KI, KBr, $K_2CO_3$, $KHCO_3$, $K_2SO_4$, and examples of calcium salts include e.g. $CaCl_2$, $CaI_2$, $CaBr_2$, $CaCO_3$, $CaSO_4$, $Ca(OH)_2$. Furthermore, organic anions of the aforementioned cations may be contained in the composition of the invention. According to a more preferred embodiment, the composition of the invention suitable for injection purposes as defined above, may contain salts selected from sodium chloride (NaCl), calcium chloride ($CaCl_2$) and optionally potassium chloride (KCl), wherein further anions may be present additional to the chlorides. $CaCl_2$ can also be replaced by another salt like KCl. The composition of the invention may be hypertonic, isotonic or hypotonic with reference to the specific reference medium, i.e. the composition of the invention may have a higher, identical or lower salt content with reference to the specific reference medium, wherein preferably such concentrations of the afore mentioned salts may be used, which do not lead to damage of cells due to osmosis or other concentration effects. Reference media are e.g. liquids occurring in "in vivo" methods, such as blood, lymph, cytosolic liquids, or other body liquids, or e.g. liquids, which may be used as reference media in "in vitro" methods, such as common buffers or liquids. Such common buffers or liquids are known to a skilled person.

However, one or more compatible solid or liquid fillers or diluents or encapsulating compounds may be used as well for the inventive pharmaceutical composition, which are suitable for administration to a patient to be treated. The term "compatible" as used here means that these constituents of the inventive pharmaceutical composition are capable of being mixed with the imidazoquinolin(amines) or derivatives thereof as defined according to the present invention in such a manner that no interaction occurs which would substantially reduce the pharmaceutical effectiveness of the inventive pharmaceutical composition under typical use conditions. Pharmaceutically acceptable carriers, fillers and diluents must, of course, have sufficiently high purity and sufficiently low toxicity to make them suitable for administration to a person to be treated. Some examples of compounds which can be used as pharmaceutically acceptable carriers, fillers or constituents thereof are sugars, such as, for example, lactose, glucose and sucrose; starches, such as, for example, corn starch or potato starch; cellulose and its derivatives, such as, for example, sodium carboxymethylcellulose, ethylcellulose, cellulose acetate; powdered tragacanth; malt; gelatin; tallow; solid glidants, such as, for example, stearic acid, magnesium stearate; calcium sulfate; vegetable oils, such as, for example, groundnut oil, cottonseed oil, sesame oil, olive oil, corn oil and oil from theobroma; polyols, such as, for example, polypropylene glycol, glycerol, sorbitol, mannitol and polyethylene glycol; alginic acid.

Further additives which may be included in the inventive pharmaceutical composition are emulsifiers, such as, for example, Tween®; wetting agents, such as, for example, sodium lauryl sulfate; colouring agents; taste-imparting agents, pharmaceutical carriers; tablet-forming agents; stabilizers; antioxidants; preservatives.

According to another embodiment, the inventive pharmaceutical composition may comprise an adjuvant. In this context, an adjuvant may be understood as any compound, which is suitable to initiate or increase an immune response of the innate immune system, i.e. a non-specific immune response. With other words, when administered, the inventive pharmaceutical composition typically elicits an innate immune response due to the adjuvant, optionally contained therein. Such an adjuvant may be selected from any adjuvant known to a skilled person and suitable for the present case, i.e. supporting the induction of an innate immune response in a mammal. Preferably, the adjuvant may be selected from the group consisting of, without being limited thereto, any of the following including chitosan, TDM, MDP, muramyl dipeptide, pluronics, alum solution, aluminium hydroxide, ADJUMER™ (polyphosphazene); aluminium phosphate gel; glucans from algae; algammulin; aluminium hydroxide gel (alum); highly protein-adsorbing aluminium hydroxide gel; low viscosity aluminium hydroxide gel; AF or SPT (emulsion of squalane (5%), Tween 80 (0.2%), Pluronic L121 (1.25%), phosphate-buffered saline, pH 7.4); AVRIDINE™ (propanediamine); BAY R1005™ ((N-(2-deoxy-2-L-leucylamino-b-D-glucopyranosyl)-N-octadecyl-dodecanoylamide hydroacetate); CALCITRIOL™ (1-alpha, 25-dihydroxy-vitamin D3); calcium phosphate gel; CAPTM (calcium phosphate nanoparticles); cholera holotoxin, cholera-toxin-A1-protein-A-D-fragment fusion protein, sub-unit B of the cholera toxin; CRL 1005 (block copolymer P1205); cytokine-containing liposomes; DDA (dimethyldioctadecylammonium bromide); DHEA (dehydroepiandrosterone); DMPC (dimyristoylphosphatidylcholine); DMPG (dimyristoylphosphatidylglycerol); DOC/alum complex (deoxycholic acid sodium salt); Freund's complete adjuvant; Freund's incomplete adjuvant; gamma inulin; Gerbu adjuvant (mixture of: i) N-acetylglucosaminyl-(P1-4)-N-acetylmuramyl-L-alanyl-D-glutamine (GMDP), ii) dimethyldioctadecylammonium chloride (DDA), iii) zinc-L-proline salt complex (ZnPro-8); GM-CSF); GMDP (N-acetylglucosaminyl-(b1-4)-N-acetylmuramyl-L-alanyl-D-isoglutamine); ImmTher™ (N-acetylglucosaminyl-N-acetylmuramyl-L-Ala-D-isoGlu-L-Ala-glycerol dipalmitate); DRVs (immunoliposomes prepared from dehydration-rehydration vesicles); interferon-gamma; interleukin-1beta; interleukin-2; interleukin-7; interleukin-12; ISCOMS™; ISCOPREP 7.0.3™; liposomes; LOXORIBINE™ (7-allyl-8-oxoguanosine); LT oral adjuvant (*E. coli* labile enterotoxin-protoxin); microspheres and microparticles of any composition; MF59™; (squalene-water emulsion); MONTANIDE ISA 51™ (purified incomplete Freund's adjuvant); MONTANIDE ISA 720™ (metabolisable oil adjuvant); MPL™ (3-Q-desacyl-4'-monophosphoryl lipid A); MTP-PE and MTP-PE liposomes ((N-acetyl-L-alanyl-D-isoglutaminyl-L-alanine-2-(1,2-dipalmitoyl-sn-glycero-3-(hydroxyphosphoryloxy))-ethylamide, monosodium salt); MURAMETIDE™ (Nac-Mur-L-Ala-D-Gln-OCH$_3$); MURAPALMITINE™ and D-MURAPALMITINE™ (Nac-Mur-L-Thr-D-isoGln-sn-glyceroldipalmitoyl); NAGO (neuraminidase-galactose oxidase); nanospheres or nanoparticles of any composition; NISVs (non-ionic surfactant vesicles); PLEURAN™ (β-glucan); PLGA, PGA and PLA (homo- and co-polymers of lactic acid and glycolic acid; microspheres/nanospheres); PLURONIC L121™; PMMA (polymethyl methacrylate); PODDS™ (proteinoid microspheres); polyethylene carbamate derivatives; poly-rA: poly-rU (polyadenylic acid-polyuridylic acid complex); polysorbate 80 (Tween 80); protein cochleates (Avanti Polar Lipids, Inc., Alabaster, Ala.); STIMULON™ (QS-21); Quil-A (Quil-A saponin); S-28463 (4-amino-otec-dimethyl-2-ethoxymethyl-1H-imidazo[4,5-c]quinoline-1-ethanol); SAF1™ ("Syntex adjuvant formulation"); Sendai proteoliposomes and Sendai-containing lipid matrices; Span-85 (sorbitan trioleate); Specol (emulsion of Marcol 52, Span 85 and Tween 85); squalene or Robane® (2,6,10,15,19,23-hexamethyltetracosan and 2,6,10,15,19,23-hexamethyl-2,6,10,14,18,22-tetracosahexane); stearyltyrosine (octadecyltyrosine hydrochloride); Theramid® (N-acetylglucosaminyl-N-acetylmuramyl-L-Ala-D-isoGlu-L-Ala-dipalmitoxypropylamide); Theronyl-MDP (Termurtide™ or [thr 1]-MDP; N-acetylmuramyl-L-threonyl-D-isoglutamine); Ty particles (Ty-VLPs or virus-like particles); Walter-Reed liposomes (liposomes containing lipid A adsorbed on aluminium hydroxide), and lipopeptides, including Pam3Cys, in particular aluminium salts, such as Adjuphos, Alhydrogel, Rehydragel; emulsions, including CFA, SAF, IFA, MF59, Provax, TiterMax, Montanide, Vaxfectin; copolymers, including Optivax (CRL1005), L121, etc.; liposomes, including Stealth, cochleates, including BIORAL; plant derived adjuvants, including QS21, Quil A, Iscomatrix, ISCOM; adjuvants suitable for costimulation including Tomatine, biopolymers, including PLG, PMM, Inulin; microbe derived adjuvants, including Romurtide, DETOX, MPL, CWS, Mannose, CpG nucleic acid sequences, CpG7909, ligands of human TLR 1-10, ligands of murine TLR 1-13, ISS-1018, IC31, Ampligen, Ribi529, IMOxine, IRIVs, VLPs, cholera toxin, heat-labile toxin, Pam3Cys, Flagellin, GPI anchor, LNFPIII/Lewis X, antimicrobial peptides, UC-1V150, RSV fusion protein, cdiGMP; and adjuvants suitable as antagonists including CGRP neuropeptide.

The inventive pharmaceutical composition may additionally contain one or more auxiliary substances in order to further increase its immunomoulatory effect. A synergistic action of the imidazoquinolin(amines) or a derivative thereof as defined according to the present invention and of an auxiliary substance, which may be optionally contained in the inventive pharmaceutical composition as described above, is preferably achieved thereby. Depending on the various types of auxiliary substances, various mechanisms can come into consideration in this respect. For example, compounds that permit the maturation of dendritic cells (DCs), for example lipopolysaccharides, TNF-alpha or CD40 ligand, form a first class of suitable auxiliary substances. In general, it is possible to use as auxiliary substance any agent that influences the immune system in the manner of a "danger signal" (LPS, GP96, etc.) or cytokines, such as GM-CSF, which allow for an immune response produced by the immune-stimulating adjuvant according to the invention to be enhanced and/or influenced in a targeted manner. Particularly preferred auxiliary substances are cytokines, such as monokines, lymphokines, interleukins or chemokines, that further promote the innate immune response, such as IL-1, IL-2, IL-3, IL-4, IL-5, IL-6, IL-7, IL-8, IL-9, IL-10, IL-12, IL-13, IL-14, IL-15, IL-16, IL-17, IL-18, IL-19, IL-20, IL-21, IL-22, IL-23, IL-24, IL-25, IL-26, IL-27, IL-28, IL-29, IL-30, IL-31, IL-32, IL-33, INF-alpha, IFN-beta, INF-gamma, GM-CSF, G-CSF, M-CSF, LT-beta or TNF-alpha, growth factors, such as hGH.

The inventive pharmaceutical composition can also additionally or alternatively contain any further compound, which is known to be immune-stimulating due to its binding affinity (as ligands) to human Toll-like receptors TLR1, TLR2, TLR3, TLR4, TLR5, TLR6, TLR7, TLR8, TLR9, TLR10, or due to its binding affinity (as ligands) to murine Toll-like receptors TLR1, TLR2, TLR3, TLR4, TLR5, TLR6, TLR7, TLR8, TLR9, TLR10, TLR11, TLR12 or TLR13.

Another class of compounds, which may be added to an inventive pharmaceutical composition in this context, may be CpG nucleic acids, in particular CpG-RNA or CpG-DNA. A CpG-RNA or CpG-DNA can be a single-stranded CpG-DNA (ss CpG-DNA), a double-stranded CpG-DNA (dsDNA), a single-stranded CpG-RNA (ss CpG-RNA) or a double-stranded CpG-RNA (ds CpG-RNA). The CpG nucleic acid is preferably in the form of CpG-RNA, more preferably in the form of single-stranded CpG-RNA (ss CpG-RNA). The CpG nucleic acid preferably contains at least one or more (mitogenic) cytosine/guanine dinucleotide sequence(s) (CpG motif(s)). According to a first preferred alternative, at least one CpG motif contained in these sequences, that is to say the C (cytosine) and the G (guanine) of the CpG motif, is unmethylated. All further cytosines or guanines optionally contained in these sequences can be either methylated or unmethylated. According to a further preferred alternative, however, the C (cytosine) and the G (guanine) of the CpG motif can also be present in methylated form.

The inventive pharmaceutical composition typically comprises a "safe and effective amount" of the above components of the inventive pharmaceutical composition, particularly of the imidazoquinolin(amines) and derivatives thereof as defined according to the present invention. As used herein, a "safe and effective amount" means an amount of these component, particularly of the imidazoquinolin(amines) and derivatives thereof, that is sufficient to significantly induce a positive modification of a disease or disorder as defined herein. At the same time, however, a "safe and effective amount" is small enough to avoid serious side-effects, that is to say to permit a sensible relationship between advantage and risk. The determination of these limits typically lies within the scope of sensible medical judgment. A "safe and effective amount" of the components of the inventive pharmaceutical composition, particularly of the imidazoquinolin (amines) and derivatives thereof, will furthermore vary in connection with the particular condition to be treated and also with the age and physical condition of the patient to be treated, the body weight, general health, sex, diet, time of administration, rate of excretion, drug combination, their activity, the severity of the condition, the duration of the treatment, the nature of the accompanying therapy, of the particular pharmaceutically acceptable carrier used, and similar factors, within the knowledge and experience of the accompanying doctor. The inventive pharmaceutical composition may be used for human and also for veterinary medical purposes, preferably for human medical purposes.

Without being bound thereto, in some embodiments, the inventive pharmaceutical composition will contain or release sufficient active imidazochinolin(amine) or a derivative thereof to provide a dose of about 10, 20, 50, or 100 nanograms per kilogram (ng/kg) to about 50 milligrams per kilogram (mg/kg), preferably about 10 micrograms per kilogram (µg/kg) to about 5 mg/kg, of the compound or a salt thereof to the subject. In other embodiments, the inventive pharmaceutical composition will contain or release sufficient active imidazochinolin(amine) or a derivative thereof to provide a dose of, for example, from about 0.0001, 0.001, 0.01 or 0.01 mg/m$^2$ to about 5.0 mg/m$^2$, computed according to the Dubois method, in which the body surface area of a subject (m$^2$) is computed using the subject's body weight: m$^2$=(wt kg$^{0.425}$×height cm$^{0.725}$)×0.007184, although in some embodiments the methods may be performed by administering a compound or salt or composition in a dose outside this range. In some of these embodiments, the method includes administering sufficient imidazochinolin(amine) or a derivative thereof to provide a dose of from about 0.0001, 0.001, 0.01, or 0.1 mg/m$^2$ to about 2.0 mg/m$^2$ to the subject, for example, a dose of from about 0.004, 0.04, or 0.4 mg/m$^2$ to about 1.2 mg/m$^2$.

The inventive pharmaceutical composition may be administered locally. Routes for local administration in general include, for example, topical administration routes but also intravesical, intradermal, transdermal, subcutaneous, or intramuscular injections or intralesional, intracranial, intrapulmonal, intracardial, and sublingual injections. More preferably, the inventive pharmaceutical composition may be administered by an intravesical route. The suitable amount of the inventive pharmaceutical composition to be administered can be determined by routine experiments with animal models. Such models include, without implying any limitation, rabbit, sheep, mouse, rat, dog and non-human primate models. Preferred unit dose forms for injection include sterile solutions of water, physiological saline or mixtures thereof.

The following embodiments are specifically preferred compositions of the invention being restricted to specific components.

Preferably, the inventive pharmaceutical composition as defined above comprises at least one imidazoquinolin(amine) or a derivative thereof as defined herein and at least one organic acid as defined above selected from lactic acid and/or acetic acid—preferably in such a concentration that its final pH is from pH 3 to 5, preferably 3.5 to 4.5. Thereby, the components of the inventive composition form the inventive adduct structures. The inventive pharmaceutical composition as defined above comprises preferably at least one imidazoquinolin(amine) or a derivative thereof as defined herein and at least one organic acid as defined above selected from lactic acid and/or acetic acid, however containing no more than 4, 3, 2, 1 or most preferably no further organic and/or inorganic acid as defined herein or, alternatively, less than 2 inorganic acids and no further organic acid or, still alternatively, just on additional organic acid and no inorganic acids.

Preferably, the inventive pharmaceutical composition as defined above comprises at least one imidazoquinolin(amine) or a derivative thereof as defined herein, and at least one organic acid as defined above selected from lactic acid and/or acetic acid, and less than 4, or 3 thermo-sensitive agents or more preferably just one thermo-sensitive agent. Alternatively, the inventive composition may also comprise no thermosensitive agent. The combination of a restricted number of thermo-sensitive agents in the inventive pharmaceutical composition and a restricted number of acids as defined above are also provided. Accordingly, the inventive pharmaceutical composition as defined above may comprise e.g. at least one imidazoquinolin(amine) or a derivative thereof as defined herein and at least one organic acid as defined above selected from lactic acid and/or acetic acid, and less than 4, 3, 2, or 1 further organic and/or inorganic acids as defined herein, and less then 4, 3, or 2 thermo-sensitive agents, preferably all of them belonging to the class of pluronics, more preferably those pluronic compounds which are defined as being preferred herein.

Preferably, the inventive pharmaceutical composition may comprise no surfactants apart from thermo-sensitive agents (if any), which may have additionally surfactant properties. Accordingly, the inventive composition may comprise also no surfactant and no thermo-sensitive agent.

Preferably, the inventive pharmaceutical composition may contain less than 4, 3, or 2 cyclodextrines or, alternatively, no cyclodextrine at all. These embodiments may be combined with the preferred above embodiments. Accordingly, the inventive composition may e.g. contain no thermosensitive agent, no cyclodextrine and no surfactant. In addition, the inventive composition may contain no further solubility enhancer, be it a surfactant, a cyclodextrin or be it another solubility enhancing compound, apart from lactic and/or acetic acid.

Preferably, the inventive composition comprises at least one imidaziquinoli(amine) compound, acetic and/or lactic acid and 1, 2 or no thermosensitive agent(s) and no further solubility enhancing compound and no further therapeutically active ingredient and no cellulose or cellulose derivative. In that embodiment, the inventive composition may exclusively additionally contain one or more of the following standard components belonging to the class of stabilizers and preservatives.

According to one specific embodiment, the inventive pharmaceutical composition comprises acetic acid and/or lactic acid in a concentration of about 0.025 to about 0.2 M, imidazoquinolin(amine) in an amount of about 0.1% (w/v) to about 1% (w/v), cyclodextrin(s) in an amount of about 2% (w/v) to about 6% (w/v) and Poloxamer 407 in an amount of about 10% (w/v) to about 25% (w/v), preferably the inventive pharmaceutical composition comprises acetic acid and/or lactic acid in a concentration of about 0.075 to about 0.125 M, e.g. e.g. of about 0.08 M to about 0.125 M, of about 0.085 M to about 0.125 M, of about 0.09 M to about 0.125 M, of about 0.095 M to about 0.125 M, of about 0.1 M to about 0.125 M, or of about 0.075 M to about 0.120 M, of about 0.075 M to about 0.115 M, of about 0.075 M to about 0.110 M, of about 0.075 M to about 0.105 M, of about 0.075 M to about 0.105 M or of about 0.08 M to about 0.120 M, e.g. of about 0.085 M to about 0.115 M, of about 0.09 M to about 0.110 M, of about 0.095 M to about 0.105 M, or of about 0.1 M, imidazoquinolin(amine) in an amount of about 0.1% (w/v) to about 1% (w/v), e.g. in an amount of about 0.1, 0.2, 0.3, 0.4, 0.5, 0.6, 0.7, 0.8, 0.9 or 1.0 (w/v), cyclodextrin(s) in an amount of about 2% (w/v) to about 6% (w/v), e.g. e.g. of about 2.5% (w/v) to about 6% (w/v), of about 3% (w/v) to about 6% (w/v), of about 3.5% (w/v) to about 6% (w/v), of about 4% (w/v) to about 6% (w/v), of about 4.5% (w/v) to about 6% (w/v), or of about 2.5% (w/v) to about 5.5% (w/v), about 3% (w/v) to about 5.5% (w/v), of about 3.5% (w/v) to about 5.5% (w/v), of about 4% (w/v) to about 5.5% (w/v), of about 4.5% (w/v) to about 5.5% (w/v), or of about 5% (w/v), and Poloxamer 407 in an amount of about 12% (w/v) to about 25% (w/v), e.g. in an amount of about 12% (w/v) to about 24% (w/v), in an amount of about 12% (w/v) to about 23% (w/v), in an amount of about 12% (w/v) to about 22% (w/v), in an amount of about 12% (w/v) to about 21% (w/v), in an amount of about 12% (w/v) to about 20% (w/v), in an amount of about 12% (w/v) to about 19% (w/v), in an amount of about 12% (w/v) to about 18% (w/v), in an amount of about 12% (w/v) to about 17% (w/v), in an amount of about 12% (w/v) to about 16% (w/v), or more particularly in an amount of about 13% (w/v) to about 24% (w/v), in an amount of about 13% (w/v) to about 23% (w/v), in an amount of about 13% (w/v) to about 22% (w/v), in an amount of about 13% (w/v) to about 21% (w/v), in an amount of about 13% (w/v) to about 20% (w/v), in an amount of about 13% (w/v) to about 19% (w/v), in an amount of about 13% (w/v) to about 18% (w/v), in an amount of about 13% (w/v) to about 17% (w/v), in an amount of about 13% (w/v) to about 16% (w/v), or more particularly in an amount of about 14% (w/v) to about 24% (w/v), in an amount of about 14% (w/v) to about 23% (w/v), in an amount of about 14% (w/v) to about 22% (w/v), in an amount of about 14% (w/v) to about 21% (w/v), in an amount of about 14% (w/v) to about 20% (w/v), in an amount of about 14% (w/v) to about 19% (w/v), in an amount of about 14% (w/v) to about 18% (w/v), in an amount of about 14% (w/v) to about 17% (w/v), in an amount of about 14% (w/v) to about 16% (w/v), or more particularly in an amount of about 15% (w/v) to about 24% (w/v), in an amount of about 15% (w/v) to about 23% (w/v), in an amount of about 15% (w/v) to about 22% (w/v), in an amount of about 15% (w/v) to about 21% (w/v), in an amount of about 15% (w/v) to about 20% (w/v), in an amount of about 15% (w/v) to about 19% (w/v), in an amount of about 15% (w/v) to about 18% (w/v), in an amount of about 15% (w/v) to about 17% (w/v), in an amount of about 15% (w/v) to about 16% (w/v), or in an amount of about 16% (w/v).

According to a further aspect of the present invention the object of the present invention is solved by the use of imidazoquinolin(amines) and derivatives thereof as defined herein (for the manufacture of a pharmaceutical composition, e.g. as defined herein,) for the prophylaxis, treatment and/or amelioration of any of the diseases and disorders as defined herein, e.g. skin disorders including precancerous conditions, such as actinic keratosis, genital warts (condylomata), VIN (vulvar intraepithelial neoplasia), VAIN (vaginal intraepithelial neoplasia), etc., Molluscum contagiosum, skin cancers, such as basal cell carcinoma, Bowen's disease, squamous cell carcinoma, superficial malignant melanomas, etc., bladder diseases, such as, for example, bladder cancer and cystitis, etc, cancer, including peritoneal cancer, ovarian cancer, etc.

Transurethral bladder tumour resection and adjuvant intravesical immunotherapy with BCG is standard treatment for high grade NMIBC. However, many patients show recurrence of disease and the impact on disease progression is only limited (Sylvester F J, Van der Meijden A P, Lamm D L. intravesical bacillus Calmette-Guerin reduces the risk of progression in patients with superficial bladder cancer: a metaanalysis of the published results of randomized clinical trials. J Urol 2002; 168:196470) or even absent (Malmström P U, Sylvester R J, Crawford E D, Friedrich M, Krege S, Rintala E, Solsona E, Di Stasi S M, Witjes J A. An individual patient data meta-analysis of the long-term outcome of randomized studies comparing intravesical Mitomycin C versus Bacillus Calmette-Guerin for non-muscle-invasive bladder cancer. Eur Urol 2009; 56 (2):247256). Moreover, BCG treatment can lead to serious local and systemic side effects (Witjes J A, Palou J, Soloway M, Lamm O, Brausi M, Spermon J R, Persad R, Buckley R, Akaza H, Colombel M, Böhle A. Clinical Practice recommendations for the prevention and management of intravesical therapy-associated adverse events. Eur. Urol Suppl 2008; 7: 667-74). Therefore, novel therapeutic treatment options to improve the overall treatment success rates, possibly with a lower toxicity profile, for non-muscle invasive bladder cancers are urgently needed.

Surprisingly, it could be shown that intravesically administered imidazoquinolin(amines) in pigs is well tolerated, causes no bladder wall toxicity and formulations with poloxamer and HPβCD stay longer in the bladder with less systemic absorption. The safety profile of intravesical imidazoquinolin(amines) compares favorable to that of current therapies such as BCG.

Accordingly, to a particularly preferred embodiment, the object of the present invention is solved by the use of imidazoquinolin(amines) and derivatives thereof as defined herein, (for the manufacture of a pharmaceutical composition, e.g. as defined herein,) for the (intravesical) treatment of bladder diseases, such as, for example, bladder cancer, such as for instance non-muscle invasive bladder cancers, and cystitis, etc. For this specific purpose, imidazoquinolin(amines) and derivatives thereof as defined herein are preferably provided in a formulation as described above for the inventive pharmaceutical composition.

Finally, the present invention furthermore comprises methods of treatment of diseases and disorders as defined herein, including skin disorders including precancerous conditions, such as actinic keratosis, genital warts (condylomata), VIN (vulvar intraepithelial neoplasia), VAIN (vaginal intraepithelial neoplasia), etc., Molluscum contagiosum, skin cancers, such as basal cell carcinoma, Bowen's disease, squamous cell carcinoma, superficial malignant melanomas, etc., bladder diseases, such as, for example, bladder cancer, such as for instance non-muscle invasive bladder cancers, and cystitis, etc, cancer, including peritoneal cancer, ovarian cancer, etc., using the inventive pharmaceutical composition, preferably as defined above. In this context, such methods of treatment as defined above preferably comprise administration of the inventive pharmaceutical composition using any administration mode as defined above, preferably including, topical administration routes but also intravesical, intradermal, transdermal, subcutaneous, or intramuscular injections or intralesional, intracranial, intrapulmonal, intracardial, and sublingual injections.

Particularly preferred, the present invention comprises methods of (intravesical) treatment of bladder diseases, such as, for example, bladder cancer, such as for instance non-muscle invasive bladder cancers, and cystitis, etc., using the inventive pharmaceutical composition, preferably as defined above. In this context, such methods of (intravesical) treatment of bladder diseases typically comprises the intravesical administration of the inventive pharmaceutical composition. Furthermore, the inventive pharmaceutical composition may be administered using non-invasive methods, such as an injection needle having a cannula of a suitable diameter, an injection tube, endoscopic methods, etc.

It is to be understood that this invention is not limited to the particular methodology, protocols and reagents described herein as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art.

FIGURES

The following Figures are intended to illustrate the invention further. They are not intended to limit the subject matter of the invention thereto.

Figure 12:
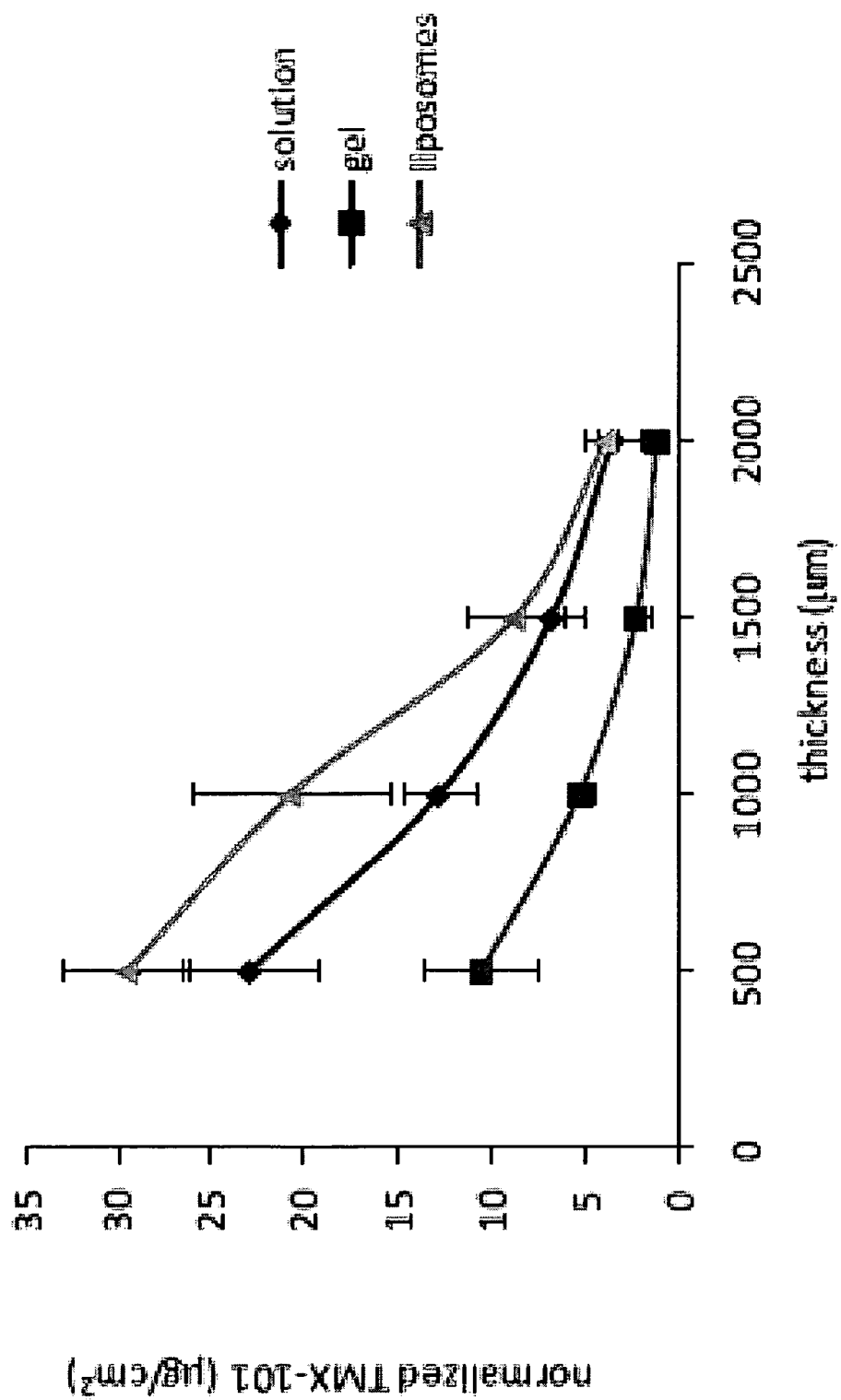

FIG. 12 shows the amount of imiquimod (TMX-101) recovered in BE (bladder epithelium) after 4 hours of contact with the formulation (see Example 5), namely for 0.9% Imiquimod—15% HP-β-CD dissolved in 0.1 M lactic acid solution, or in 19% Poloxamer 407 gel containing 15% HP-β-CD (0.1 M lactic acid) or in liposome dispersion (1% soybean lecithin in 0.1 M lactic acid solution). It is shown that the inventive formulations show a considerably better effect in long term release than the liposomal formulation which is given herein for comparative purposes.

Figure 13:
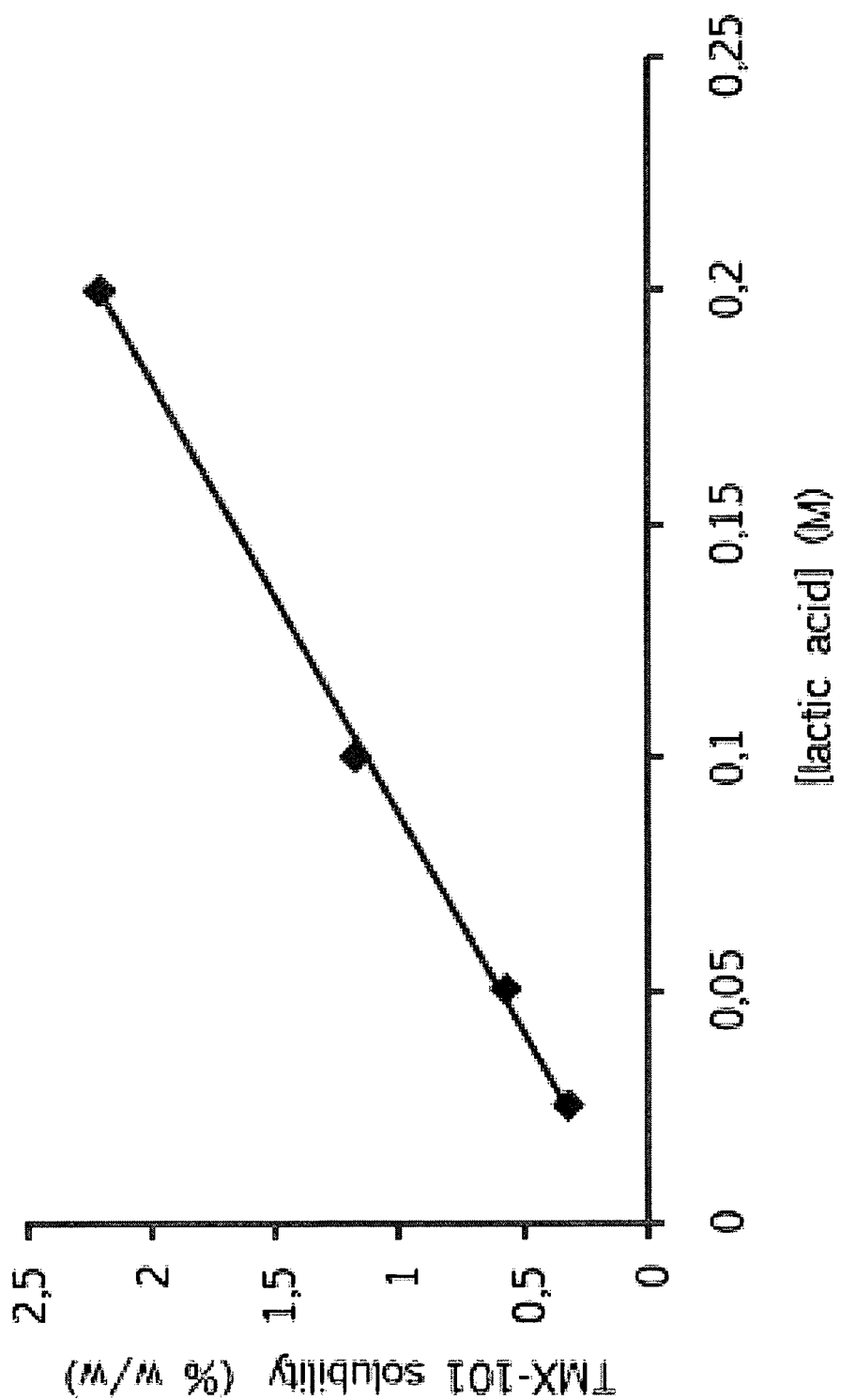

FIG. 13 shows imiquimod (TMX-101) solubility in presence of different lactic acid concentrations. Solubility increases as a function of the lactic acid concentration.

Figure 14:
Figure 14:
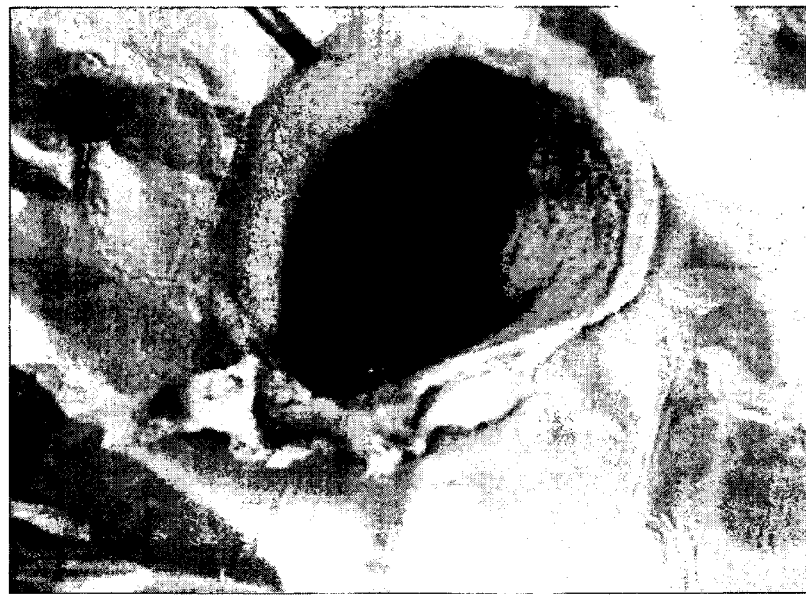

FIG. 14. In the top part bladders from pigs are shown which were excised, washed and transferred into NaCl solution at 37° C. Formulations according to the invention were applied to the bladder and the bladder sectioned after 10 minutes. The gel state of the formulation applied were observed. In the bottom part, the bladder after addition of an inventive formulation comprising imiquimod in 20% Polaxamer 4077 in lactic acid solution (0.1 M)), which was previously stained by Coomassie Blue, is shown and the gel is still observed. No adhesion of the gel is observed.

Figure 15:
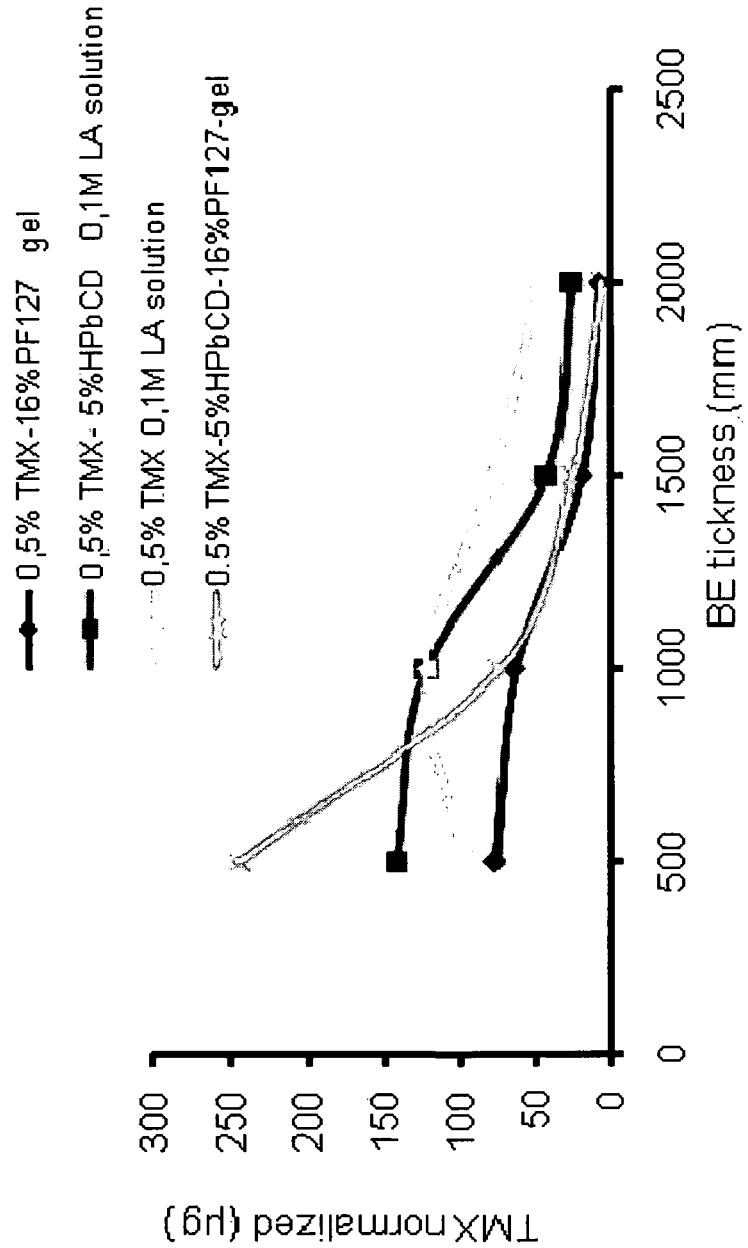

FIG. 15 shows the amount of imiquimod (TMX) recovered in bladder epithelium (BE) after 4 hours of contact with the different imiquimod formulations (data are normalized for the absorption areal and are the mean of 3 experiments).

Figure 16:
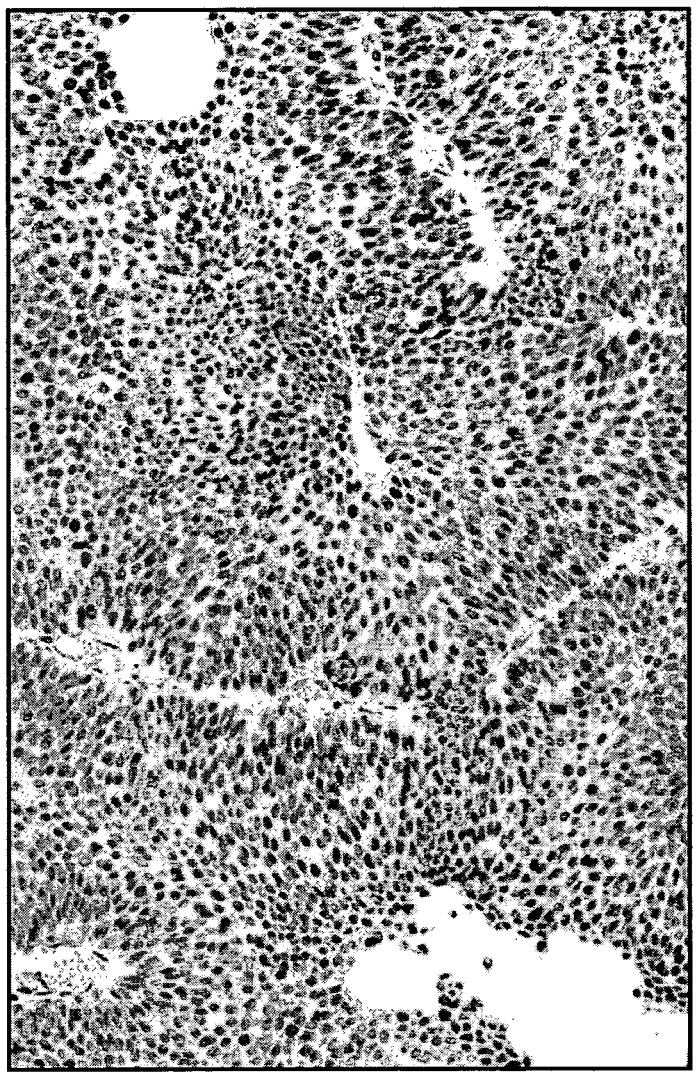

FIG. 16 shows an immunohistochemical staining for TLR-7 of human bladder cancer (sub)mucosa according to example 10.3.1 (original magnification 40×).

Figure 17:

FIG. 17 shows an immunohistological staining for TLR-7 of pig bladder (sub)mucosa according to example 10.3.1 (original magnification 40×).

Figure 18:
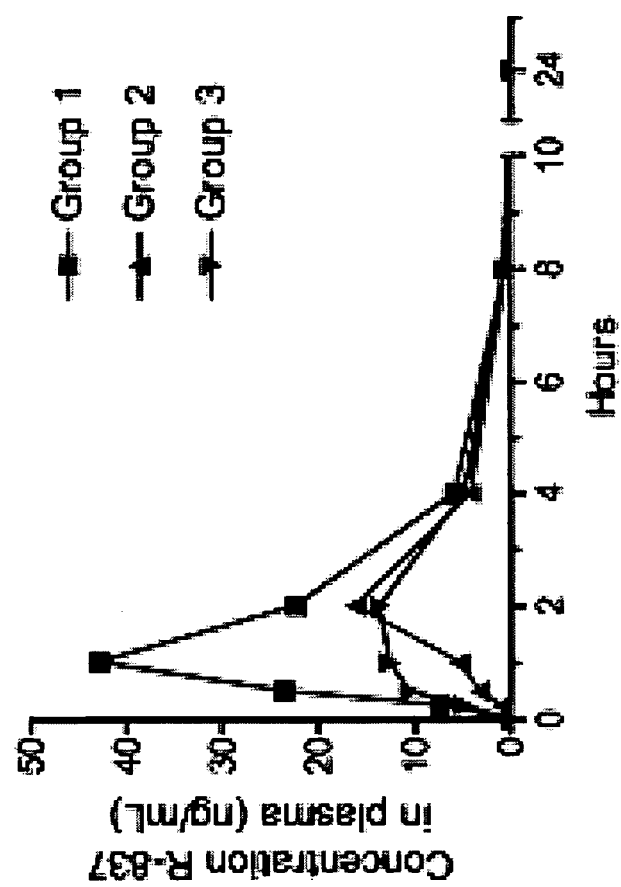

FIG. 18 shows the pharmacokinetic plasma parameters of imiquimod (R-837) administered to groups of pigs treated with different formulations of imiquimod. Animals received a solution of imiquimod 0.5% dissolved in 0.1 M lactic acid (group 1); a solution of imiquimod 0.5% dissolved in 0.1 M lactic acid, poloxamer 407 16% as emulsifying agent and HPβCD (hydroxypropyl-β-cyclodextrin) 15% as stabilizing agent (group 2); a solution of imiquimod 0.5% dissolved in 0.1 M lactic acid, poloxamer 407 16% and HPβCD 5% (group 3).

Figure 19:

FIG. 19 shows normal (sub)mucosal appearance of a pig bladder (original magnification 20×)

Figure 20:

FIG. 20 shows moderate predominantly lymphocytic submucosal inflammatory reaction one day after instillation of study drug (group 3) of example 10.3.2 (original magnification 20×).

Figure 21:

FIG. 21 shows leucocytoclastic vasculitis with fibrinoid vessel wall necrosis in pig bladder submucosa (group 1) of example 10.3.2 (original magnification 20×).

Figure 22:
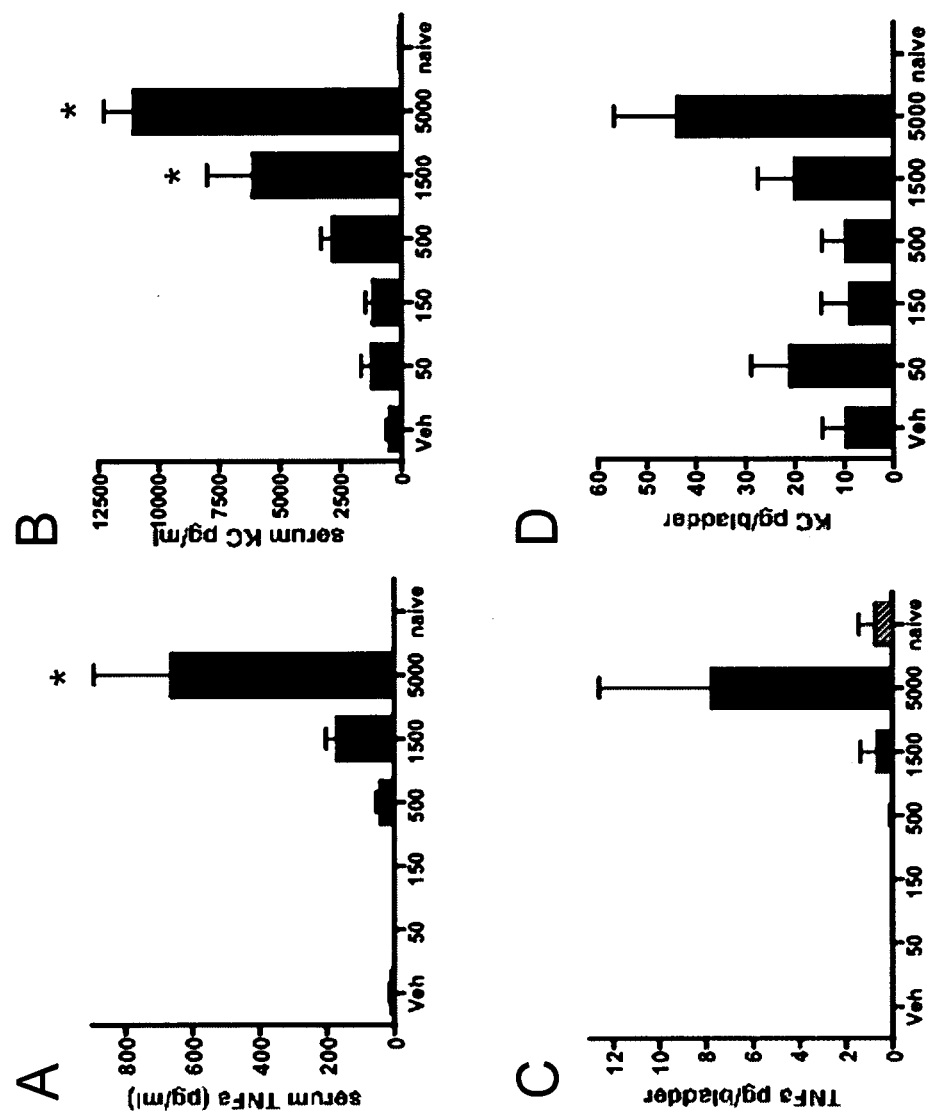

FIG. 22 shows cytokine and chemokine induction by intravesical administration of imiquimod in 0.1% lactic acid according to example 11.3.1. Mice (n=8) intravesically received various doses of imiquimod in lactic acid formulation. Two hours after administration, sera and bladder lavage were collected. The levels of TNFα (A) and KC (B) in serum, and TNFα (C) and KC (D) in the bladder lavage, were measured. Data shown are representative of two independent experiments (mean±SEM.). * denotes p<0.05 compared to the mice treated with vehicle (Veh) by one way ANOVA tests with Dunnett's post hoc testing.

Figure 23:
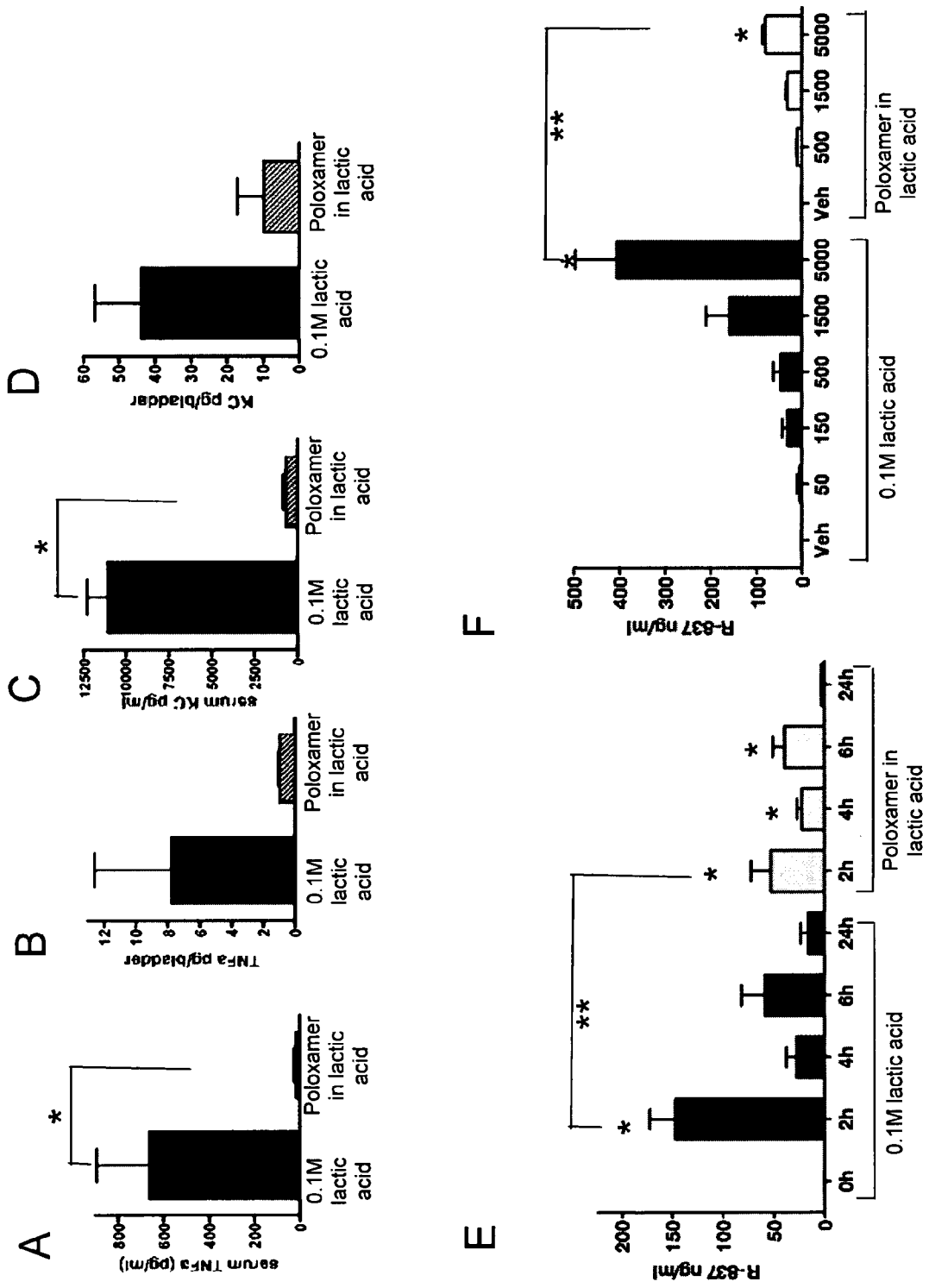

FIG. 23 shows pharmacokinetics of imiquimod (R-837) in mice after intravesical administration according to example 11.3.2. (A-D) Mice (n=8) were administered 5000 nmoles imiquimod in lactic acid or poloxamer formulation. The levels of serum TNFα (A), TNFα in bladder lavage (B), serum KC (C), and KC in bladder lavage (D) were measured. * denotes p<0.01 assessed by the unpaired Student t test. (E) Mice (n=6 to 8) were administered 1500 nmoles imiquimod in lactic acid or poloxamer formulation. Sera were collected 2, 4, 6, 24 hours after the administration. (F) Mice (n=6) were administered various doses of imiquimod in 100 µL in lactic acid or poloxamer formulations. Sera were collected 2 to 4 hours after the administration. The levels of imiquimod were determined by Chiman SRL. Data shown are pooled values from two independent experiments (mean±SEM.). * denotes p<0.05 by one way ANOVA tests with Dunnett's post hoc testing compared to treated mice at 0 hour time point or mice treated with vehicle alone (Veh). ** denotes statistical significance (p<0.01) assessed by one way ANOVA tests with Bonferroni's post hoc testing.

Figure 24:
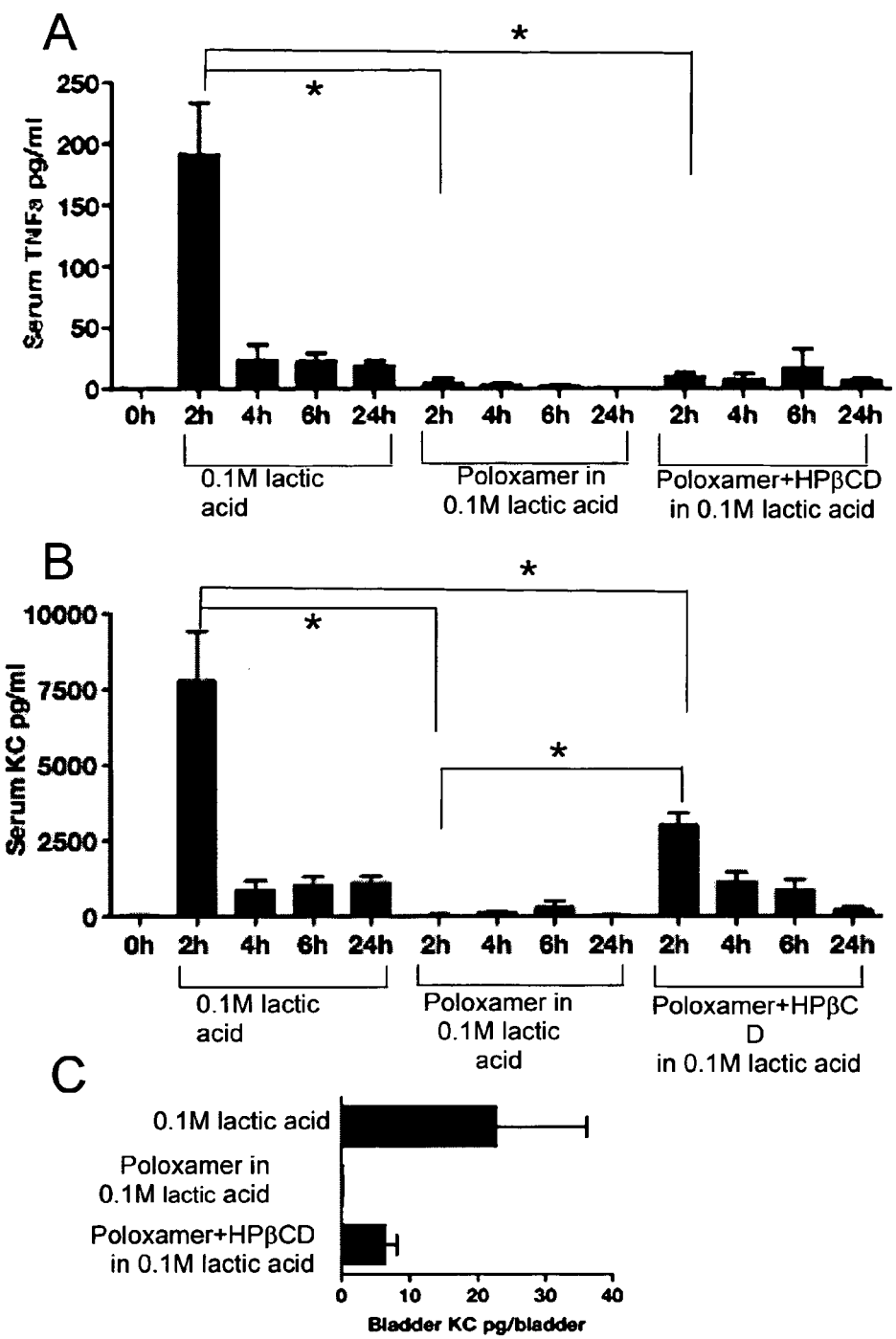

FIG. 24 shows incorporation of HPβCD partially restores systemic TNFα and KC levels according to example 11.3.3. Mice (n=8) were administered 1500 nmoles imiquimod in lactic acid, poloxamer or poloxamer-HPβCD formulation. The levels of TNFα (A) and KC (B) are shown. Data presented are pooled values from two independent experiments (mean±SEM). * denotes p<0.05 by one way ANOVA tests with Dunnett's post hoc testing. (C) C57BL/6 mice were injected 5000 nmoles imiquimod in lactic acid, poloxamer, or poloxamer-HPβCD formulations. The levels of KC in the lavage were assessed by Luminex beads assay. Data presented are pooled values from three independent experiments (mean±SEM.).

Figure 25:
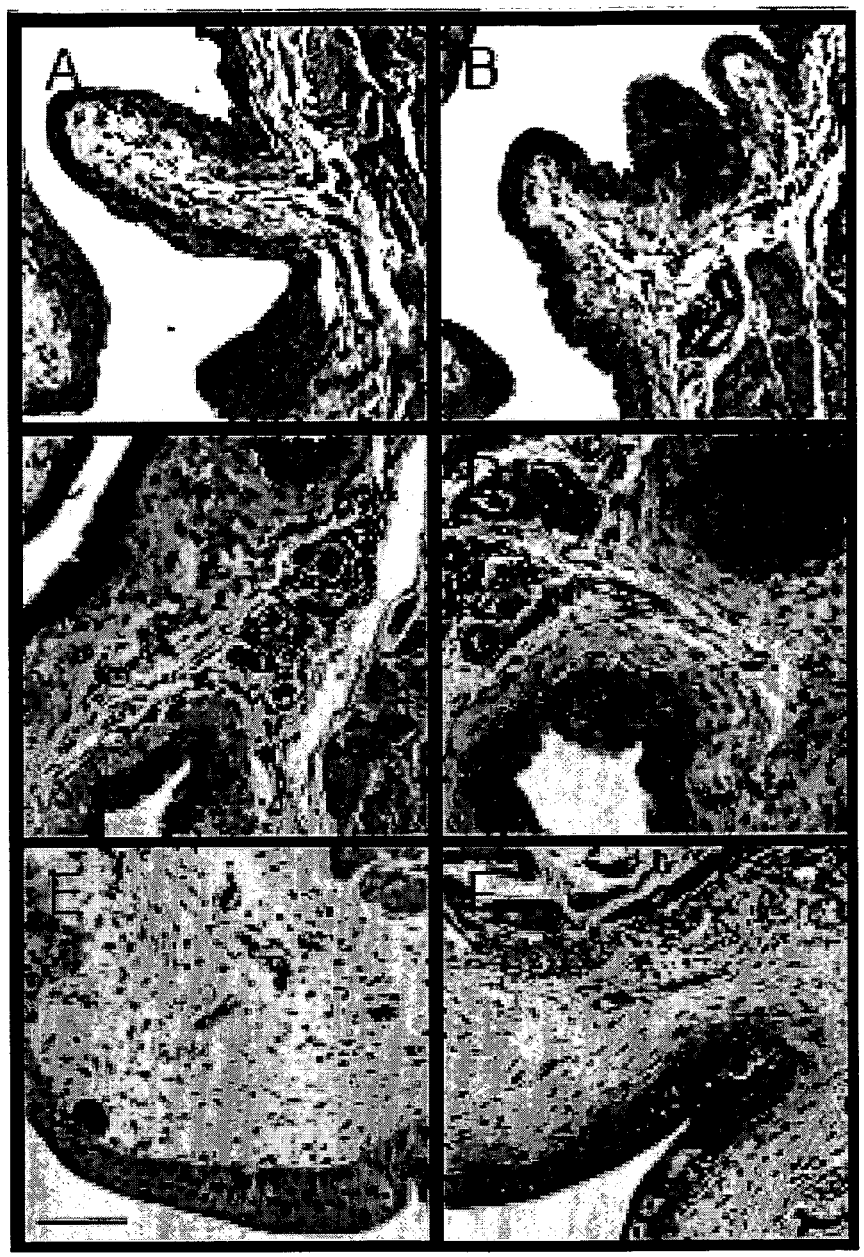

FIG. 25 shows representative histology of murine bladder treated with 0.1% imiquimod (R-837) in poloxamer-HPβCD formulation according to example 11.3.4. A: Single treatment Veh (wild type C57BL/6) B: Three times treatment Veh (wild type C57BL/6) C: Single treatment imiquimod (wild type C57BL/6) D: Three times treatment imiquimod (wild type C57BL/6) E: Three times treatment saline (wild type C57BL/6) F: Three times treatment imiquimod (TLR7 ko) C57BL/6 (A-E) or TLR7 deficient mice (ko) (F) were intravesically treated with 0.1% imiquimod in poloxamer-HPβCD formulation on day 0 (single treatment), 50 µL on days 0, 4, and 8 (three times treatment). The bladders were collected on day 1 for single treatment (A and C) or on day 9 for three times treatment (B, D, E and F) and stained with H&E. Mice treated with vehicle alone (Veh, n=4) and naïve mice served as controls (B and E). Scale bar: 100 µm. Original magnification was 200×.

Figure 26:
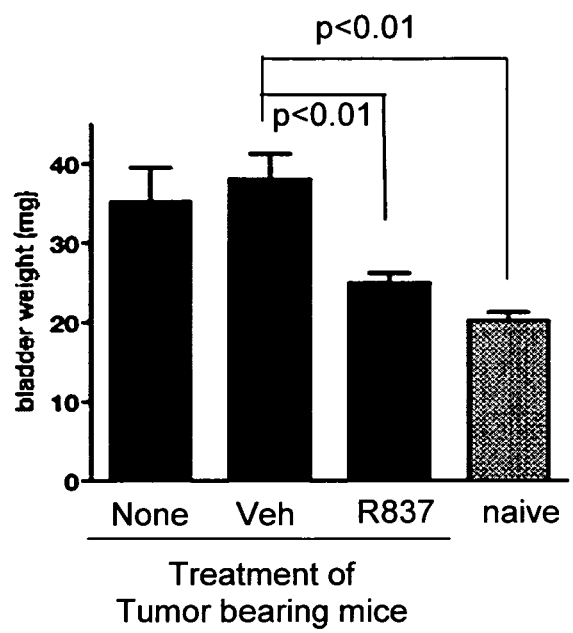

FIG. 26 shows reduced bladder weight of mice bearing MB49 treated 0.1% imiquimod in poloxamer-HPβCD formulation according to example 11.3.5. Mice (n=11) bearing MB49 bladder tumor intravesically received 50 µL 0.1% imiquimod in poloxamer-HPβCD formulation on days 3, 6 and 9. Mice were sacrificed on day 11 and the bladder weight was measured. Naive mice without tumor implantation (naïve), MB49 implanted-mice with no treatment (None) or vehicle treated mice (Veh) served as controls. Data shown are pooled values of three independent experiments (mean±SEM.). Statistical significance was assessed by one-way ANOVA tests with Kruskal-Wallis test.

EXAMPLES

The following Examples are intended to illustrate the invention further. They are not intended to limit the subject matter of the invention thereto.

1. Example

Solubility of Imiquimod 1.1. Preliminary Tests
1.1.1. Solubility of Imiquimod in Hydrochloric Acid 48 mg of imiquimod was weighed and added of hydrochloric acid solutions at different concentrations: in particular 48.2 mg imiquimod were treated with 8 ml hydrochloric acid 0.1N, 48.6 mg imiquimod with 9 ml hydrochloric acid 0.2 N and 48.4 mg imiquimod with 8 ml hydrochloric acid 2 N. After vortexing for 5 minutes, the samples were visually inspected.

The drug is slightly soluble in hydrochloric acid 0.1N, 0.2 N and 2 N. The system prepared with HCl 2 N is a transparent solution at 74° C. The theoretical concentration of the drug dissolved in it was 0.042 M corresponding to 1.0%.

1.1.2. Solubility of Imiquimod in Glacial Acetic Acid

A weighed amount of drug (48.2 mg) was dissolved under agitation in 2 ml glacial acetic acid. After complete solubilisation a weighed aliquot of imiquimod (150 mg) was added to this solution in order to visually evaluate the maximum concentration of dissolved drug. This preliminary experiment demonstrates that it is possible to solubilise 10 g of imiquimod in 100 ml of 100% acetic acid at room temperature (10% (w/v).

1.1.3. Solubility of Imiquimod in Buffers

The solubility of imiquimod at different pH values was determined. Two different procedures were used. The drug was dispersed in the buffer (without acetic acid as co-solvent). 72 mg imiquimod were dispersed with 10 ml citrate buffer, 155 mg imiquimod in 10 ml phosphate buffer and 192 mg in 10 ml acetate buffer. After vortexing for 5 minutes, each sample was visually inspected.

Imiquimod was completely dissolved in glacial acetic acid and 1 ml of this solution (2.41% imiquimod) was diluted with 9 ml of water, 0.9% w/w NaCl solution, phosphate buffer pH 7.0 (0.1 M), citrate buffer pH 6.0 (0.1 M) or acetate buffer pH 5.0 (0.1 M). A visual inspection of the systems was carried out.

The results of these preliminary tests indicate that imiquimod is slightly soluble in buffers. When the drug was dissolved in glacial acetic acid and then diluted with buffers, clear, transparent solutions were obtained: the pH of these systems was always lower than 3.6.

1.2. Analysis of Imiquimod 1.2.1. Calibration Curve of Imiquimod in Acetic Acid by Spectrophotometer A weighed amount of drug (0.0124 g) was dissolved in 100 ml of solvent (acetic acid/water 1:9). The solution concentration was 0.0005 M. Different amounts of this solution were opportunely diluted with the same solvent to prepare five standard solutions with concentrations ranging from $2\times10^{-6}$-$5\times10^{-5}$ M (in particular $2\times10^{-6}$ M, $5\times10^{-6}$ M, $10\times10^{-6}$ M, $20\times10^{-6}$ M, $50\times10^{-6}$ M). These solutions were spectrophotometrically analyzed. The absorbance was determined at three wavelengths (250, 305, 319 nm).

The concentrations of standard solutions used for the calibration of the method and the corresponding absorbance values at 319, 305 and 250 nm are shown in Table 1 below.

TABLE 1

Concentrations and absorbance values of standard imiquimod solutions.

| Concentration ($10^{-6}$ mol/l) | Abs $\lambda = 319$ nm | $\lambda = 305$ nm | $\lambda = 250$ nm |
|---|---|---|---|
| 2.0 | 0.0308 | 0.0254 | 0.0652 |
| 5.0 | 0.0669 | 0.0625 | 0.2853 |
| 10.0 | 0.13,29 | 0.1146 | 0.4213 |
| 20.0 | 0.2548 | 0.2082 | 0.6687 |
| 50.0 | 0.6164 | 0.4858 | 1.3974 |

1.2.2. Calibration Curve of Imiquimod in Acetic Acid by HPLC

A weighed amount of imiquimod (0.0316 g) was dissolved in 250 ml of solvent (acetonitrile (ACN)/water pH 3.5). The solution concentration was 0.0005 M. Different amounts of this solution were appropriately diluted with the same solvent to prepare standard solutions with concentrations in the range $2\times10^{-6}$-$3\times10^{-5}$ M (in particular $2\times10^{-6}$ M, $3\times10^{-6}$ M, $10\times10^{-6}$ M, $20\times10^{-6}$ M, $30\times10^{-6}$ M). These solutions were analyzed by HPLC for imiquimod.

The samples were analyzed in the following conditions:
Column: Symmetry Shield RP18 (150×4.6 mm, 3.5 µm)
Pre-column: Symmetry C18 (3.9×20 mm, 5 µm)
Mobil phase: Solution A: Acetonitrile
Solution B: solution containing 50 mM ammonium acetate (3.85 g in 1 l of water)
Flow (ml/min): 1.0
Gradient: see Table 2
Oven temperature (° C.): 40
Wavelength (nm): 250
Injection volume (µl): 20

TABLE 2

Gradient for calibration by HPLC

| time (minutes) | solution A (%) | solution B (%) | elution |
|---|---|---|---|
| 0 | 20 | 80 | equilibration |
| 0-16 | 20-30 | 80-70 | linear gradient |
| 16-18 | 30 | 70 | isocratic |
| 18-26 | 30-50 | 70-50 | linear gradient |
| 26-31 | 50-80 | 50-20 | linear gradient |
| 31-40 | 80 | 20 | isocratic |
| 40-42 | 80-20 | 20-80 | linear gradient |
| 42-50 | 20 | 80 | re-equilibration |

Under these analysis conditions the retention time of imiquimod was 18 minutes.

The concentrations of standard solutions used for the method calibration and the corresponding peak areas are shown in Table 3 below.

TABLE 3

Concentrations and peak areas of imiquimod standard solutions.

| Concentration ($10^{-6}$ mol/l) | Area (U.A.) |
|---|---|
| 2.0 | 55868.98 |
| 3.0 | 74818.33 |
| 10.0 | 262028.00 |
| 20.0 | 526459.49 |
| 30.0 | 824246.64 |

1.3. Solubility Study 1.3.1. Imiquimod Solubility in Glacial Acetic Acid and Buffers As reported the solubility of imiquimod in glacial acetic acid, at room temperature, was 100 mg/ml (10% w/v).

The solubility was experimentally determined weighing 1200 mg of drug, adding 10 ml of glacial acetic acid and gently shaking the dispersion for 24 hours. This sample, after filtration (0.22 µm Millipore membrane filter) was analyzed by HPLC for the imiquimod content and its pH was measured.

Imiquimod (738 mg) was initially dissolved in glacial acetic acid (10 ml). A volume of this solution was appropriately diluted with phosphate buffer pH 7.0 (0.1 M), citrate buffer pH 6.0 (0.1 M) or acetate buffer pH 5.0 (0.1 M) to prepare systems containing 2.0% of drug. The samples, after filtration by 0.22 µm Millipore membrane filter, were spectrophotometrically and chromatographically analyzed for the imiquimod content. The pH was determined.

The drug solubility values in glacial acetic acid or in acetic acid diluted with phosphate, citrate or acetate buffers (0.1 M) determined by HPLC and/or spectrophotometry and the corresponding pH values are shown in Table 4.

TABLE 4

Compositions, solution pH and imiquimod solubility of systems

| Percent of | | | | Imiquimod (% w/v) | | |
|---|---|---|---|---|---|---|
| glacial acetic acid | phosphate buffer pH 7.0 | citrate buffer pH 6.0 | acetate buffer pH 5.0 | UV | HPLC | pH |
| 100 | | | | | 7.50 | |
| 27 | 73 | | | 1.55 | 1.69 | 2.92 |
| 27 | | 73 | | 0.72 | 0.86 | 3.20 |
| 27 | | | 73 | 1.92 | 1.89 | 2.92 |

1.3.2. Solubility of Imiquimod in Short-Chain Acids

Some inorganic and organic acids were considered as potential solubilizers of the drug. 100 mg imiquimod were dissolved in 10 ml of phosphoric acid 0.1 M, succinic acid 0.1 M, citric acid 0.1 M, acetic acid 0.01 M, 0.05 M, 0.1 M and lactic acid 0.01 M, 0.05 M, 0.088 M, and 0.1 M. These systems, after filtration, were spectrophotometrically analyzed for imiquimod and their pH was measured.

1.3.3. Solubility of Imiquimod in Presence of Cyclodextrin

Exactly weighed amounts of imiquimod (200 mg) and hydroxypropyl-β-cyclodextrin (HP-β-CD) (4000 mg) were dissolved in 10 ml of:

water
water at pH 5.0 (corrected with HCl)
water at pH 3.0 (corrected with HCl)
lactic acid solution (0.1 M)

After shaking for 24 hours and filtration (0.22 μm Millipore membrane filter) the solubilised imiquimod was spectrophotometrically determined. The solution pH was also measured.

1.3.4. Solubility of Imiquimod in Presence of Surfactants

Imiquimod (200 mg) was weighed and mixed with different amounts of surfactants (Tween 20, Tween 80, Cremophor EL or Pluronic F-68) in order to prepare formulations containing 0.5, 2.5 and 5% of surface active agent. Each mixture was added to 10 ml of lactic acid (0.1 M), gently shaken for 24 hours, filtered and analyzed by spectrophotometry and submitted to pH measurement.

The imiquimod present in solution in compositions prepared with different acids and surfactants is spectrophotometrically determined and is shown in Table 5 together with the pH value.

Among the acids considered as solubilizer for imiquimod, acetic and lactic acids confirm their ability to interact with the drug and solubilize it. The amount of drug in solution is directly related to the acid concentration (this is also confirmed by Example 6.1.). As solubilizer lactic acid is more efficient than acetic acid.

The surfactants associated to lactic acid do not ameliorate the solubility of imiquimod. The obtained results demonstrate that for these systems, the drug solubility depends primarily from the lactic acid and indicate that the drug is not entrapped in the micelles the surfactants form.

About the inclusion agent, while a single, high concentration of HP-β-CD has been used, it can be affirmed that this complexing agent does not substantially modify the drug solubility: the increasing concentrations observed in the different experiments are due to the decreasing pH value.

When HP-β-CD was used in association with lactic acid a small, but significant increment (about 18%) of solubility can be observed.

TABLE 5

Composition, pH value and amount of imiquimod in the formulations

| Acid (M) | | | | | excipient (%) | | | | | | |
|---|---|---|---|---|---|---|---|---|---|---|---|
| phosphoric acid | succinic acid | citric acid | acetic acid | lactic acid | Tween 20 | Tween 80 | Cremophor EL | Pluronic F68 | HP-β-CD | imiquimod (% w/v) | pH |
| 0.100 | | | | | | | | | | 0.159 | 1.80 |
| | 0.100 | | | | | | | | | 0.079 | 2.94 |
| | | 0.100 | | | | | | | | 0.010 | 2.10 |
| | | | 0.010 | | | | | | | 0.070 | 4.37 |
| | | | 0.050 | | | | | | | 0.220 | 4.08 |
| | | | 0.100 | | | | | | | 0.430 | 3.97 |
| | | | | 0.010 | | | | | | 0.130 | 4.20 |
| | | | | 0.050 | | | | | | 0.530 | 3.90 |
| | | | | 0.088 | | | | | | 0.840 | 3.71 |
| | | | | 0.100 | | | | | | 0.980 | 3.61 |
| | | | | 0.100 | 0.5 | | | | | 0.945 | 3.88 |
| | | | | 0.100 | 2.5 | | | | | 1.004 | 3.86 |
| | | | | 0.100 | 5.0 | | | | | 1.001 | 3.89 |
| | | | | 0.100 | | 0.5 | | | | 0.997 | 3.83 |
| | | | | 0.100 | | 2.5 | | | | 1.009 | 3.82 |
| | | | | 0.100 | | 5.0 | | | | 0.872 | 3.82 |
| | | | | 0.100 | | | 0.5 | | | 0.881 | 3.90 |
| | | | | 0.100 | | | 2.5 | | | 0.989 | 3.87 |
| | | | | 0.100 | | | 5.0 | | | 0.969 | 3.88 |
| | | | | 0.100 | | | | 0.5 | | 1.048 | 3.85 |
| | | | | 0.100 | | | | 2.5 | | 1.088 | 3.87 |
| | | | | 0.100 | | | | 5.0 | | 0.972 | 3.89 |
| | | | | | | | | | 40.0 | 0.004 | 7.09 |
| | | | | | | | | | 40.0 | 0.143 | 5.17 |
| | | | | | | | | | 40.0 | 0.655 | 3.05 |
| | | | | 0.100 | | | | | 40.0 | 1.141 | 4.46 |

1.3.5. Solubility of Imiquimod in Glycerol or Propylene Glycol

Imiquimod was weighed (100 mg) and added of glycerol or propylene glycol to a volume of 10 ml. After shaking (at 120° C. for 24 hours) and cooling, 10 ml of water were added: the dispersions were filtered and the imiquimod amount in the liquid phases was determined. The system prepared with glycerol as solvent showed a pH value of 5.42 and an imiquimod concentration of 0.02%. When propylene glycol was used the pH was 3.03 and the concentration of imiquimod in solution was 0.02%.

1.4. Discussion of the Results

Imiquimod is appreciably soluble in pure acetic and lactic acid (>7.5% w/v). These two acids can be used as co-solvent to prepare formulations containing relatively high amount of the active substance.

2. Example

Thermo-Reversible Gel Formulations of Imiquimod 2.1. Formulations of Semisolid Systems 2.1.1. Formulations with Poloxamer 407

Poloxamer 407 was used to prepare semisolid systems that contained as liquid phase:
water
10% acetic acid solution
0.1M acetic acid solution
0.1M lactic acid solution All systems were constituted of 25% polymer (overall amount/concentration of thermo-sensitive agent)

2.1.2. Formulations with Poloxamer 407 and Hydroxypropylmethylcelluslose

The effect of a cellulose derivative, hydroxypropylmethylcellulose (HPMC—Methocel KL5M, Colorcon, MW 15000), on the thermogelling properties of poloxamer was evaluated: pure HPMC shows gel phase transition between 40 and 50° C. and its Lower Critical Solution Temperature (LCST) can be lowered by chemical modification (by reducing degree of substitution, the gel transition temperature can be lowered to about 40° C.). Different amounts of this polymer were used: the composition of formulations containing HPMC is the following:

TABLE 6

Compositions containing HPMC
Composition (%)

| Poloxamer 407 | HPMC | water |
|---|---|---|
| 25 | 0 | 75.0 |
| 25 | 0.5 | 74.5 |
| 25 | 1.0 | 74 |
| 25 | 2.0 | 73 |

As a result, addition of cellulose derivatives do not significantly modify the rheological behavior of the formulations.

2.1.3. Formulations with Poloxamer 407 and Cyclodextrin

The literature reports the use of cyclodextrin as component of thermo-sensible semisolid systems (CDG. Palmieri et al., 15$^{th}$ Int. Symp. on Microencapsulation, Parma, Italy 18-21 Sep. 2005). Hydroxypropyl-β-cyclodextrin (HP-β-CD) at high percentages, ranging from 0 to 20% was used in systems constituted of Poloxamer 407 and water and the LCST of these formulations was determined.

2.1.4. Formulations with Poloxamer and Poloxamer 188

Mixtures of poloxamers as jellifying systems were also assessed. Poloxamer 188, PEO-PPO-PEO copolymer with MW lower than Poloxamer 407, can be used to modulate the LCST of the gel. Poloxamer 407 was in part substituted by Poloxamer 188 to obtain hydrogels that contain an amount of polymers corresponding to 25%.

TABLE 7

Different mixtures of poloxamers
Composition (%)

| Poloxamer 407 | Poloxamer 188 | water | Polymer-ratio |
|---|---|---|---|
| 23.75 | 1.25 | 75 | 9.5/0.5 |
| 22.50 | 2.5 | 75 | 9/1 |
| 21.25 | 3.75 | 75 | 8.5/1.5 |
| 21 | 4 | 75 | 8/2 |

2.1.5. Formulations with Poloxamers and Lactic or Acetic Acid

The liquid phase (water) was substituted by lactic or acetic acid: their effects and those of the drug on the rheological behavior of thermo-sensitive systems were evaluated. Among the different gel formulations prepared with organic acids (lactic or acetic acid), those that show gel transition temperatures at about 20° C. were considered. Thus, the jelled systems we selected contained:

20% w/w Poloxamer 407

25% w/w Poloxamer 407/Poloxamer 188 (9:1 weight ratio)

2.1.6. Formulations with Imiquimod

The composition of the investigated gels was the following:

Imiquimod PPG-LA 01

| Imiquimod | 0.90 g |
|---|---|
| Poloxamer 407 | 22.50 g |
| Poloxamer 188 | 2.50 g |
| Lactic acid solution (0.135M) | 74.02 g |

Imiquimod PG-LA 01

| Imiquimod | 0.90 g |
|---|---|
| Poloxamer 407 | 20.00 g |
| Lactic acid solution (0.125M) | 79.02 g |

Imiquimod PPG-AA 01

| Imiquimod | 0.40 g |
|---|---|
| Poloxamer 407 | 22.50 g |
| Poloxamer 188 | 2.50 g |
| Acetic acid solution (0.135M) | 74.02 g |

Imiquimod PG-AA 01

| Imiquimod | 0.40 g |
|---|---|
| Poloxamer 407 | 20.00 g |
| Acetic acid solution (0.125M) | 79.02 g |

2.2. Influence of the Components on the Lower Critical Solution Temperature (LCST)

The LCST values cannot be determined by DSC: while systems constituted of pure Poloxamer 407 showed an endothermic peak that can be linked to the gel transition, using mixtures of poloxamers, HP-β-CD/Poloxamer 407 or HPMC/Poloxamer 407 as gelling agents, the DSC transition signal was lost. So, the gel transition temperature was determined by viscosity measurement. The viscosity of the systems was evaluated in the range of temperature 1-40° C., using a Rheometer BROOKFIELD DV-II+, equipped with the Small Sample Adapter and the spindle S-25.

2.2.1. Viscosity of Systems Containing Different Amounts of Poloxamer 407

Figure 1:
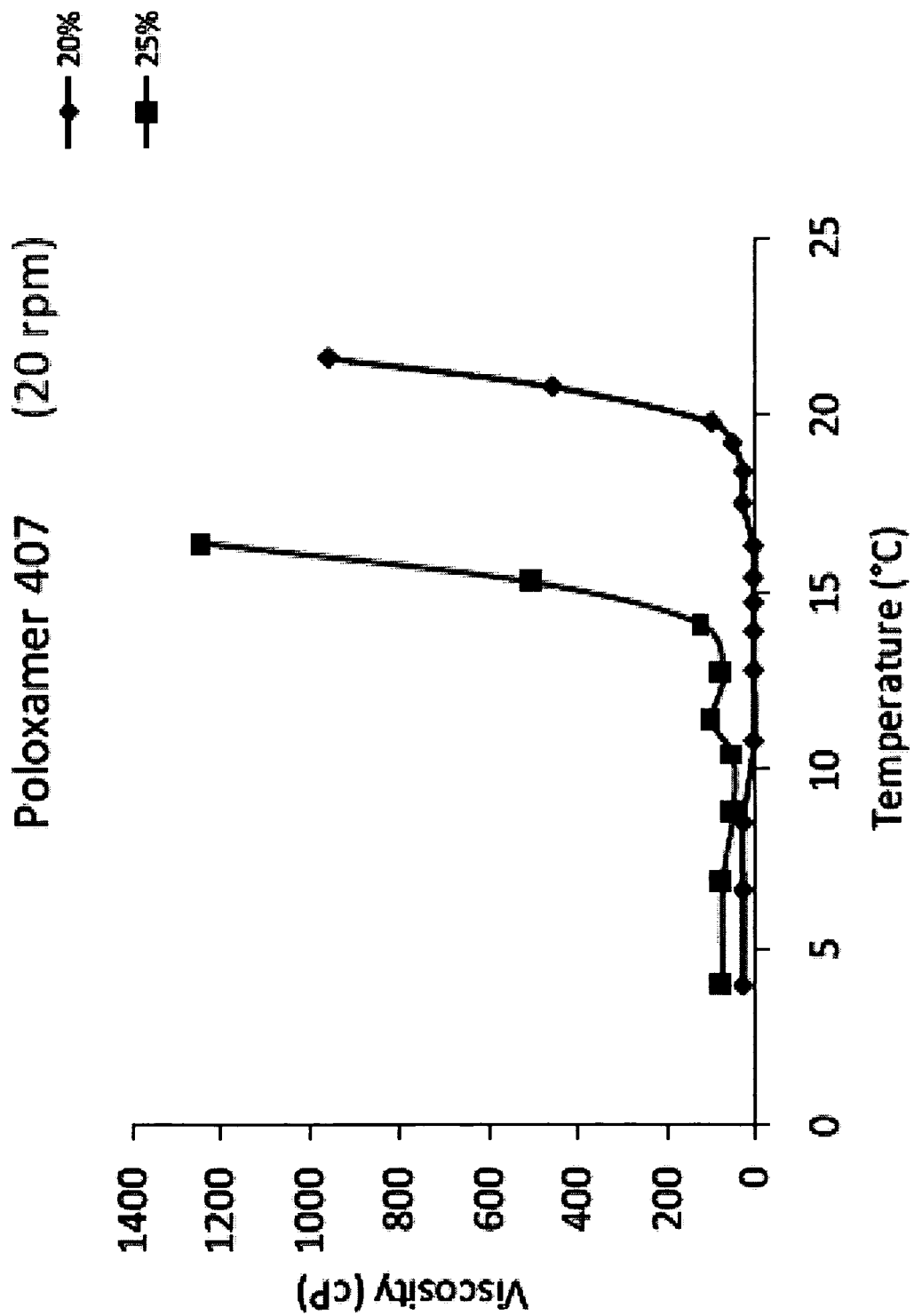
FIG. 1 shows the viscosity of systems containing different percentages of Poloxamer 407 (20% and 25%) as a function of temperature.

Decreasing the percentage of polymer, the LCST increased (see FIG. 1): at lower concentration of poloxamer, micelles require a surplus of energy to establish interactions that give semisolid consistency to the formulation. The LCST of gels containing 20 or 25% Poloxamer 407 and water as solvent are 19.93 and 13.9° C., respectively. These results are consistent with those reported in literature [A. Cabana. et al, Study of the Gelation Process of Polyethylene Oxide-Polypropylene Oxide-Polyethylene Oxide Copolymer (Poloxamer 407) Aqueous Solutions, J. COLLOID INTERFACE SCI. 190, 307-312 (1997)].

2.2.2. Viscosity of Systems Containing Poloxamer and HPMC

HPMC, in the range of concentrations considered (≤2%), is found not to modify the gel transition temperature of the formulation containing pure Poloxamer 407.

2.2.3. Viscosity of Systems Containing Poloxamer and Cyclodextrin

Figure 2:
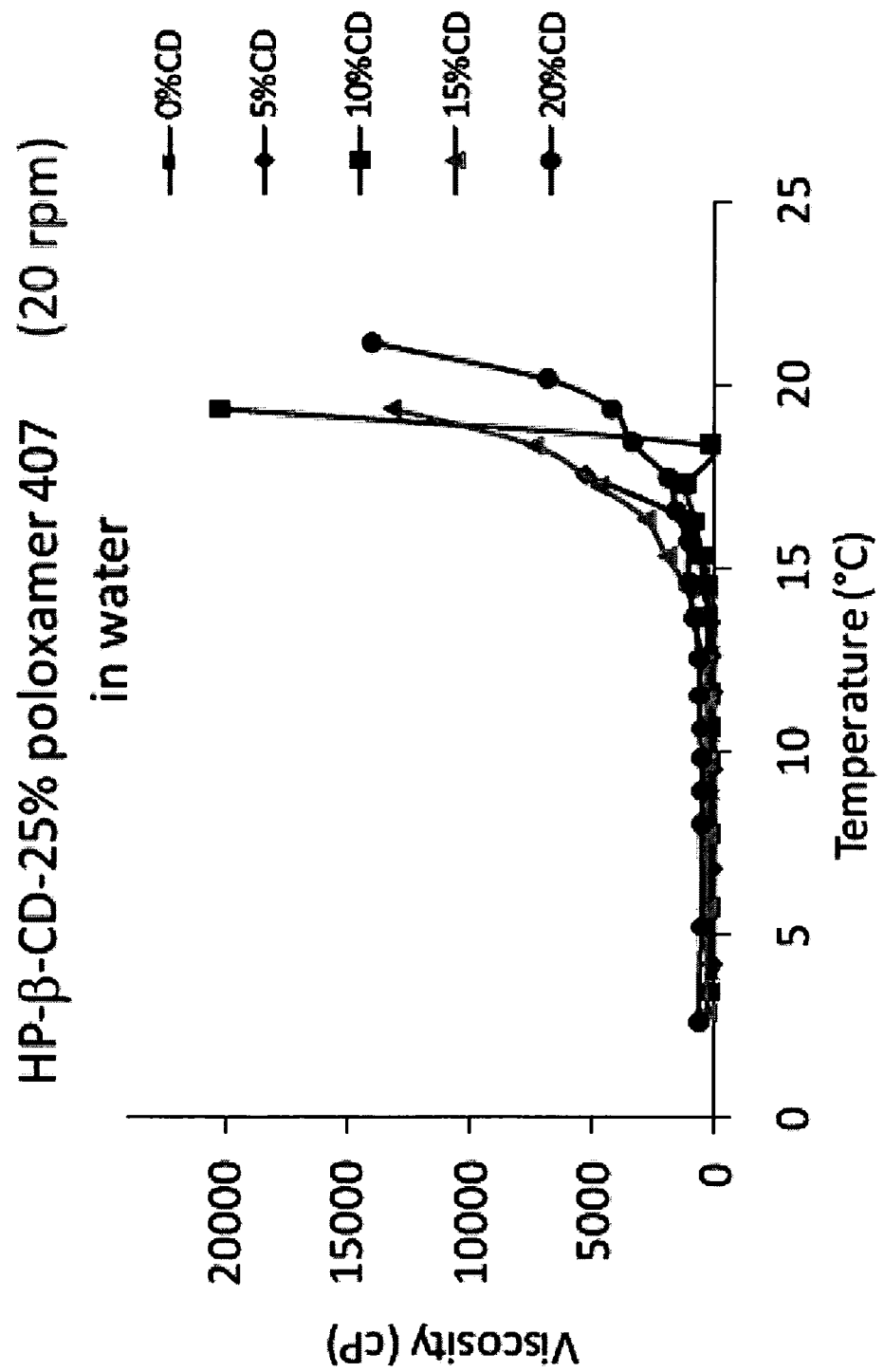
FIG. 2 shows the viscosity of systems containing different percentages of HP-β-CD (0% to 20%) as a function of temperature.

Increasing percentages of cyclodextrin (HP-β-CD) led to a slight but significant increase of LCST: the obtained results indicate a non linear relation between CD concentration and viscosity. Since CD increases the drug solubility (about 17% of increment), the use of this component in the final gel formulation may be considered (measurements on systems containing the drug were not carried out) (see FIG. 2).

2.2.4. Viscosity of Systems Containing a Mixture of Poloxamer 407 and 188

Figure 3:
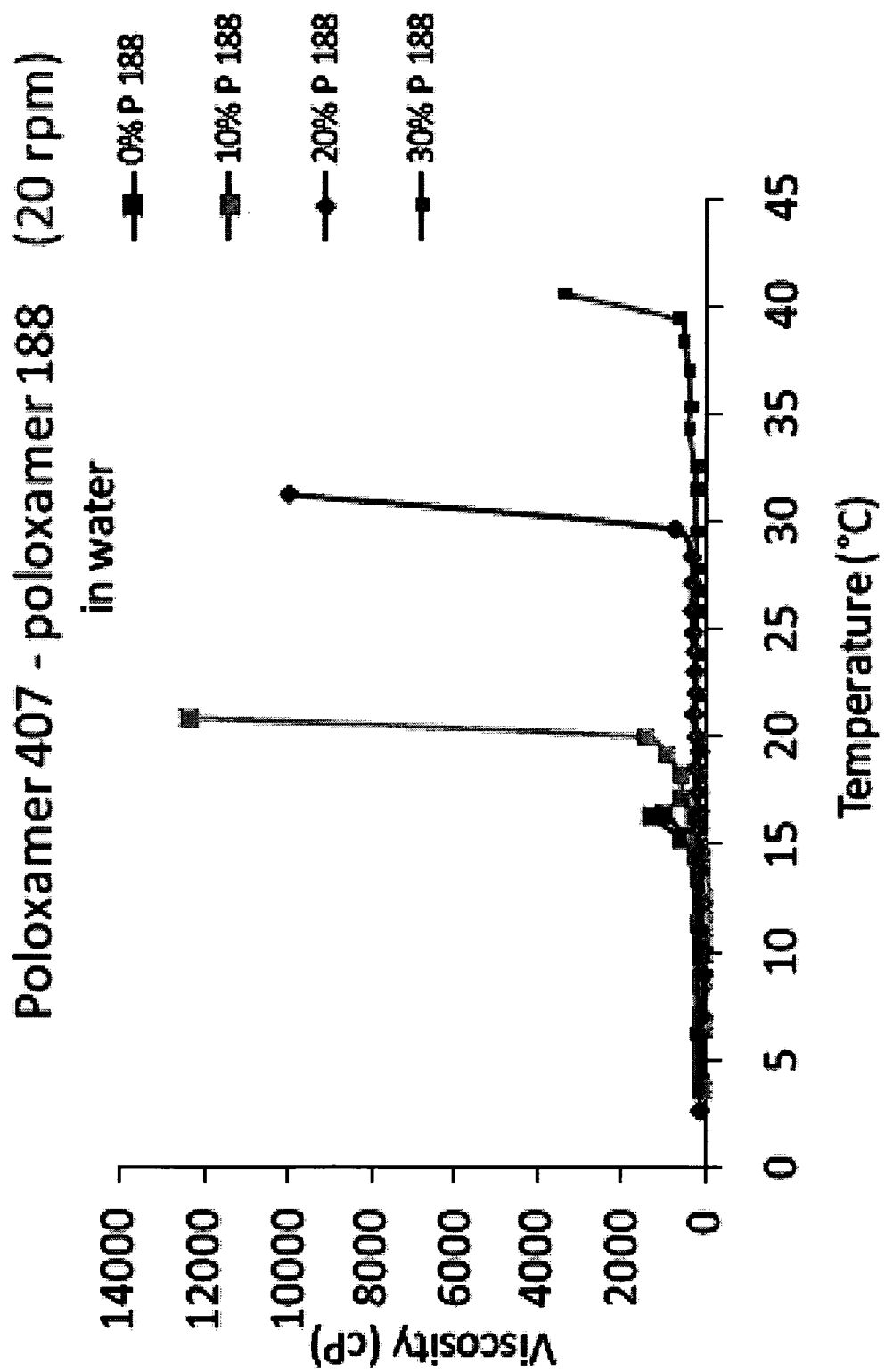
FIG. 3 shows the viscosity of systems containing different proportions of Poloxamer 407 and Poloxamer 188 (0% to 30%) as a function of temperature.

A relevant effect of Poloxamer 188 on LCST has been observed: increasing proportion of this component raises the gel transition temperature (note the linear relationship between P188 concentration and system viscosity) (see FIG. 3).

2.2.5. Viscosity of Systems Containing Acetic Acid, Lactic Acid and Imiquimod

Figure 4:
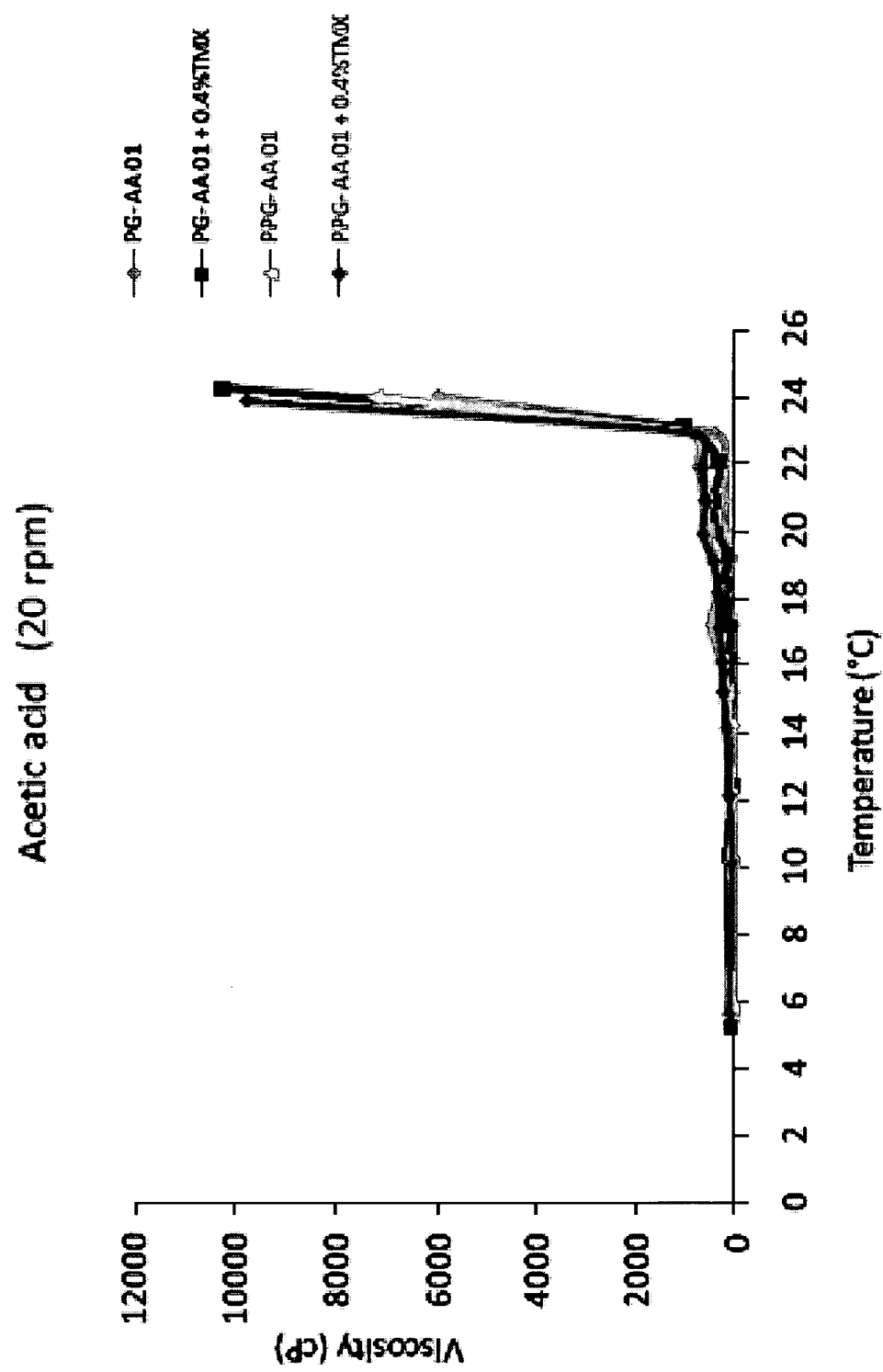
FIG. 4 shows the viscosity of systems prepared with 20% Poloxamer 407 or 25% poloxamer mixture in an acetic acid solution (AA), in presence or in the absence of imiquimod (TMX, 0.4%) as a function of temperature.
Figure 5:
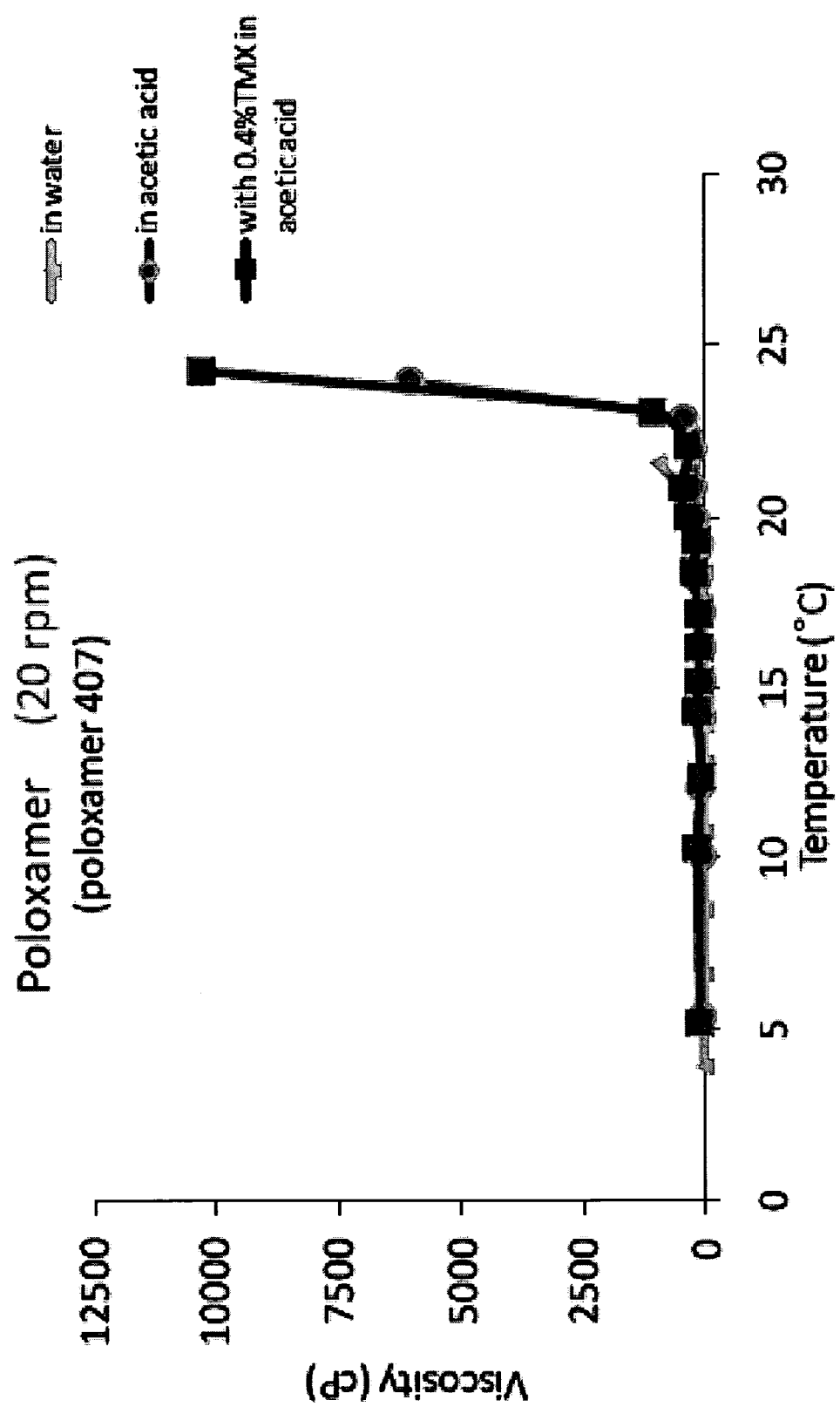
FIG. 5 shows the viscosity of systems prepared with 20% Poloxamer 407 in water or acetic acid solution (AA), or in the presence of imiquimod (TMX) in acetic acid solution as a function of temperature.
Figure 6:
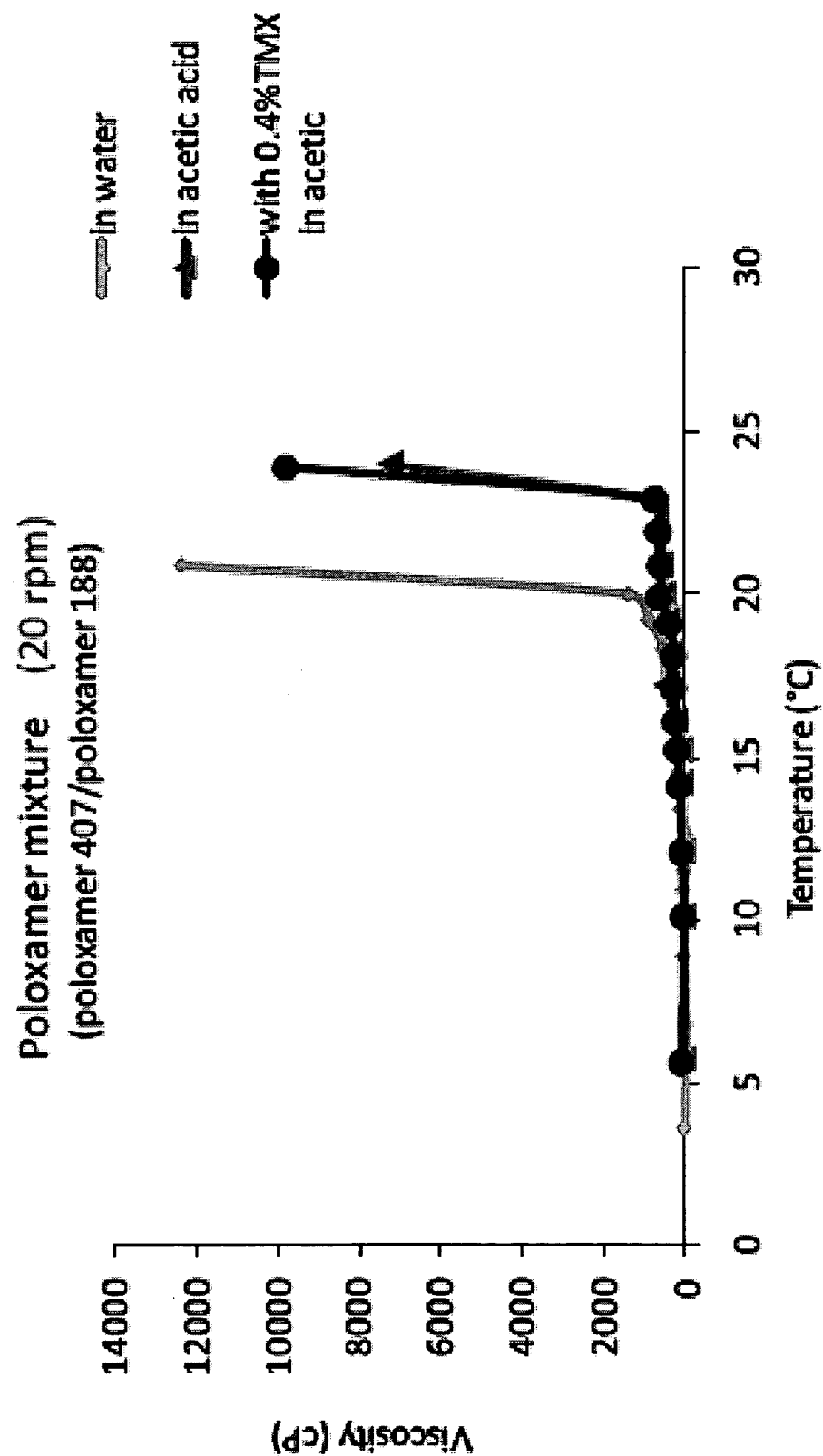
FIG. 6 shows the viscosity of systems prepared with 25% poloxamer mixture (Poloxamer 407 and Poloxamer 188) in water or acetic acid solution, in the presence of imiquimod (TMX) in acetic acid solution as a function of temperature.

It could be appreciated that, irrespective of the jellifying system, acetic acid raises the LCST of the system: this acidic component increases LCST of both imiquimod PG-AA 01 and imiquimod PPG-AA 01 to 22.85° C. Imiquimod does not significantly modify the gel transition temperature (22.95 and 23.00° C. for respectively imiquimod PG-AA 01 and imiquimod PPG-AA 01) (FIGS. 4, 5, 6).

Figure 7:
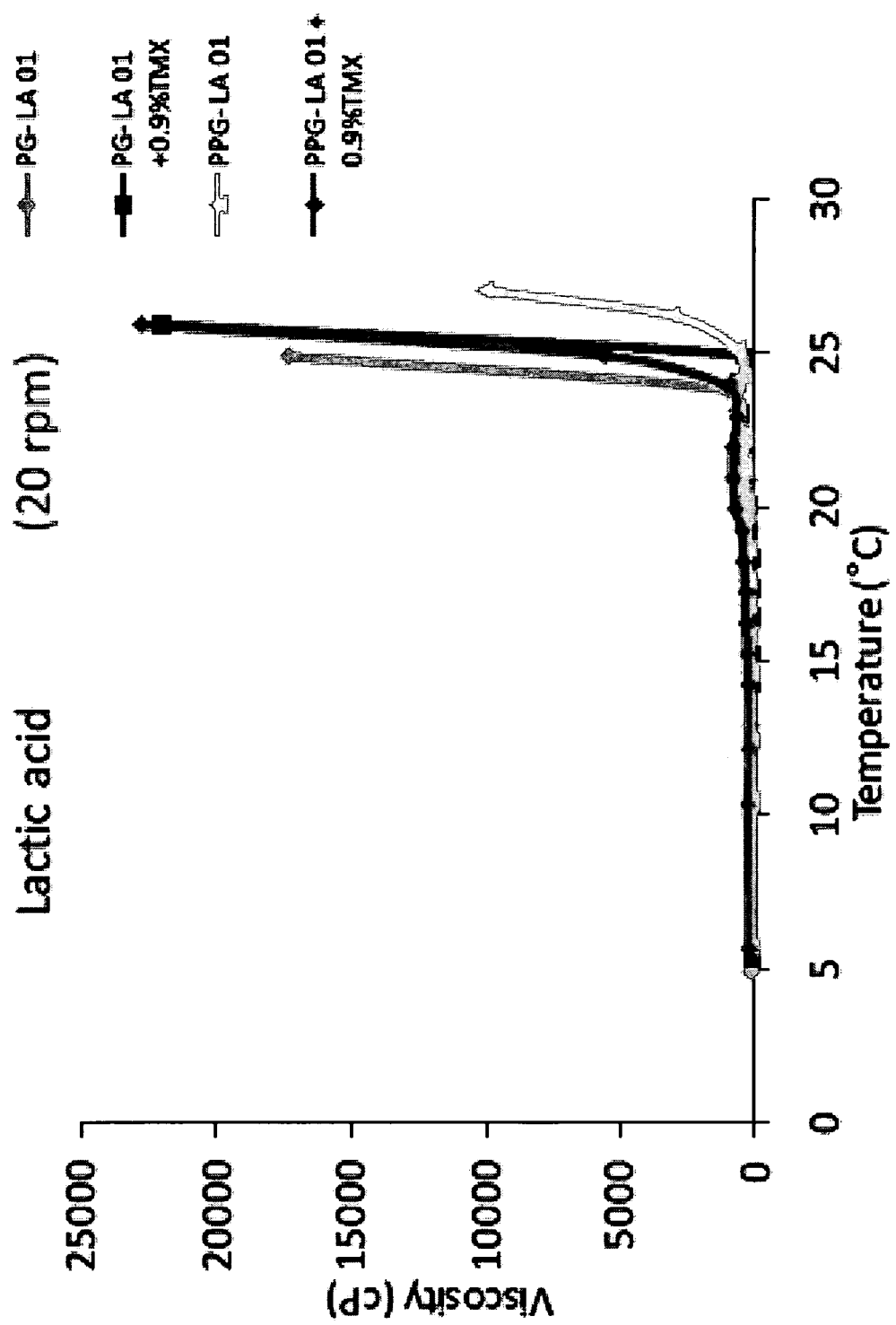
FIG. 7 shows the viscosity of systems prepared with 20% Poloxamer 407 (PG) or 25% poloxamer mixture (Poloxamer 407 and Poloxamer 188, PPG) in lactic acid solution (LA), in the presence and in the absence of imiquimod (TMX, 0.9%) as a function of temperature.
Figure 8:
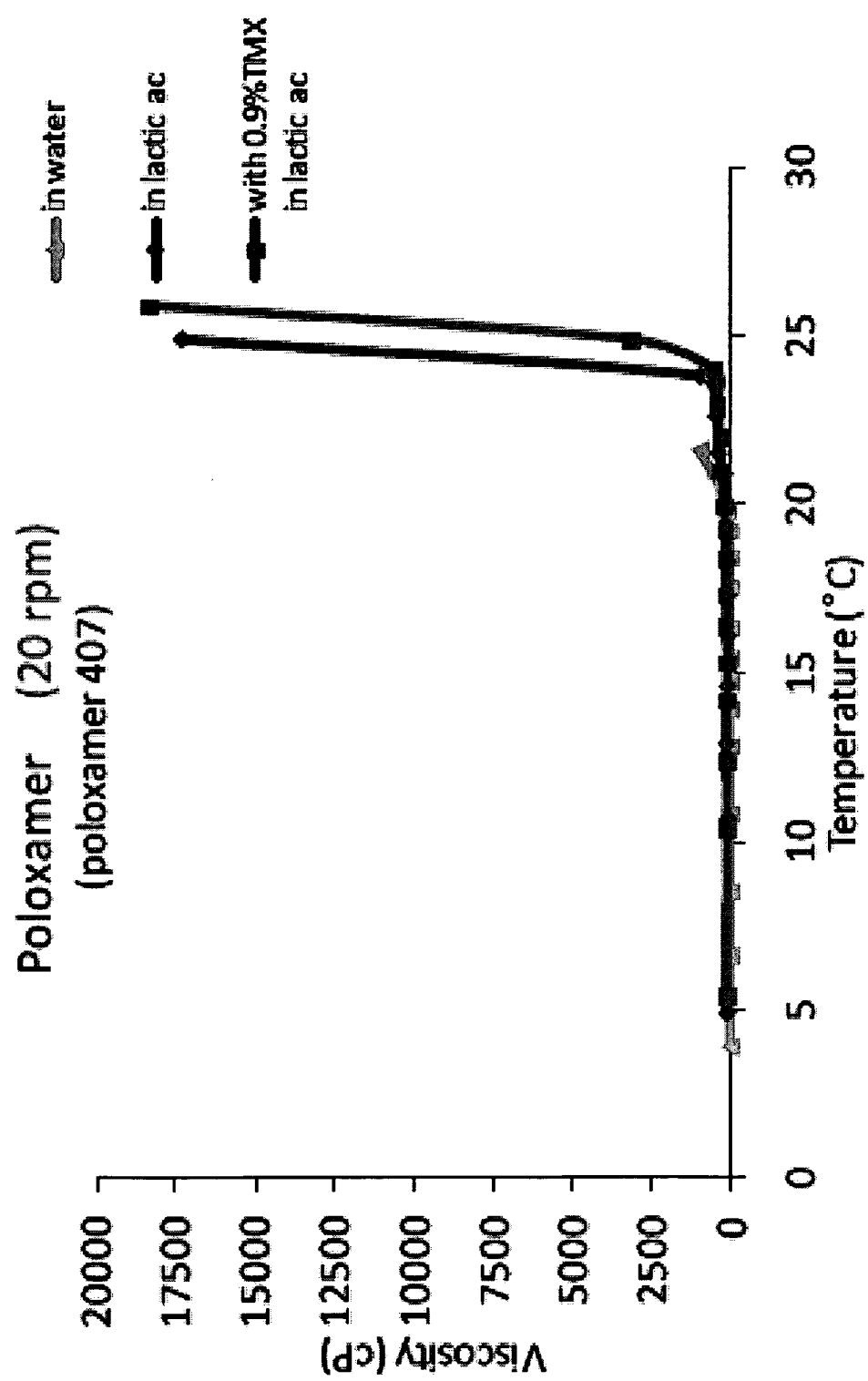
FIG. 8 shows the viscosity of systems prepared with 20% Poloxamer 407 in water or in lactic acid solution, or in the presence of imiquimod (TMX, 0.9) in lactic acid solution as a function of temperature.
Figure 9:
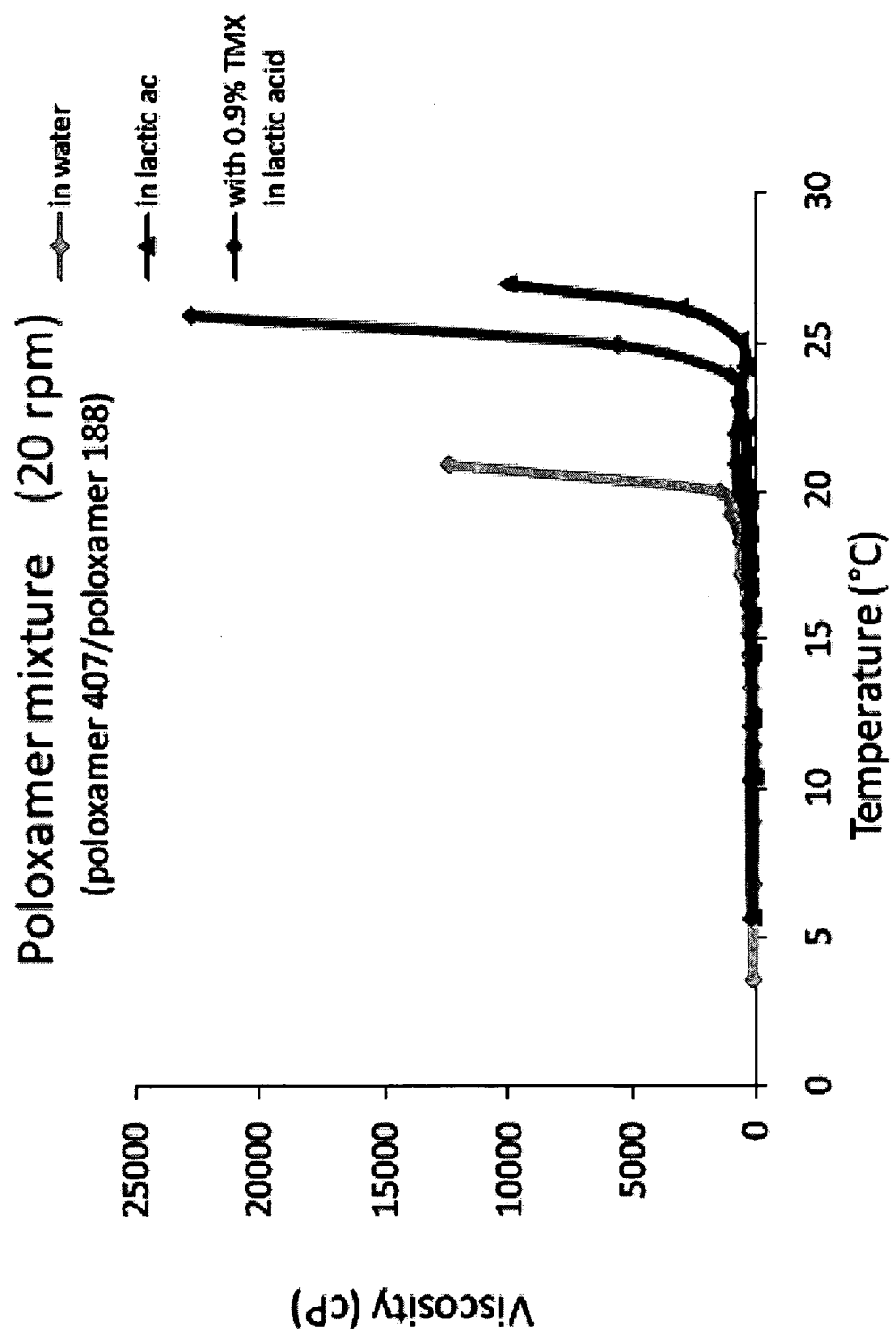
FIG. 9 shows the viscosity of systems prepared with the 25% poloxamer mixture (Poloxamer 407 and Poloxamer 188) in water or in aqueous lactic acid solution or in the presence of imiquimod (TMX, 0.9) in lactic acid solution as a function of temperature.

Also lactic acid increases the LCST of the gel formulations: as previously observed with acetic acid, the gel transition temperature of systems constituted of Poloxamer 407 is 23.8° C. With the Poloxamer 407/Poloxamer 188 mixture, in presence of lactic acid, this value is even higher (=25.9° C.) (FIGS. 7, 8, 9).

Unlike with acetic acid, imiquimod significantly affect the LCST of systems prepared with lactic acid: for imiquimod PG-LA 01 formulation (pure Poloxamer 407), the drug lead to a further, slight increase of gel transition temperature (FIG. 8); when the mixture of jellifying components was used, the temperature decreases to 24.1° C. (LCST of gel in absence of drug=25.9° C.) (FIG. 9).

3. Example

Dissolution/Erosion Test and Release Experiments of Formulations Containing Imiquimod 3.1. Compositions and Experimental Conditions
3.1.1. Compositions
An exploratory dissolution/erosion test has been performed on the following formulations:
Imiquimod PG-LA 01

| Imiquimod | 0.90 g |
| Poloxamer 407 | 20.00 g |
| Lactic acid solution (0.125M) | 79.02 g |

PG-LA01

| Poloxamer 407 | 20.00 g |
| Lactic acid solution (0.125M) | 79.02 g |

3.1.2. Experimental Conditions

The test is illustrated in "Development and in-vitro evaluation of sustained release Poloxamer 407 (P407) gel formulations of ceftiofur" by L. Zhang-J. Control. Release, 85 (2002) 73-81. The test has been carried out in 10 ml vials, closed with an elastomeric. A weighed amount of about 3 g of formulation as sol (temperature=4° C.) was transferred to the vial and the vial was stored at 37° C. until jellified. Thereafter the vial was weighed, 2 ml of acetate buffer (pH 6.0; 0.1M) were stratified onto the gel. At predetermined time intervals (after 1, 2, 3, 4 hours) the liquid phase was completely withdrawn and the vial weighed. Fresh acetate buffer was stratified onto the remaining gel. The difference of vial weight after each time interval corresponds to the amount of gel solubilized by the buffer. The percentage of dissolved gel was reported as a function of time.

For comparison, a gel studied by Zhang (J. Control. Release, 85 (2002) 73-81) was considered: this was the 25% Poloxamer 407 gel system containing ceftiofur.

3.2. Results and Discussion

Figure 10:
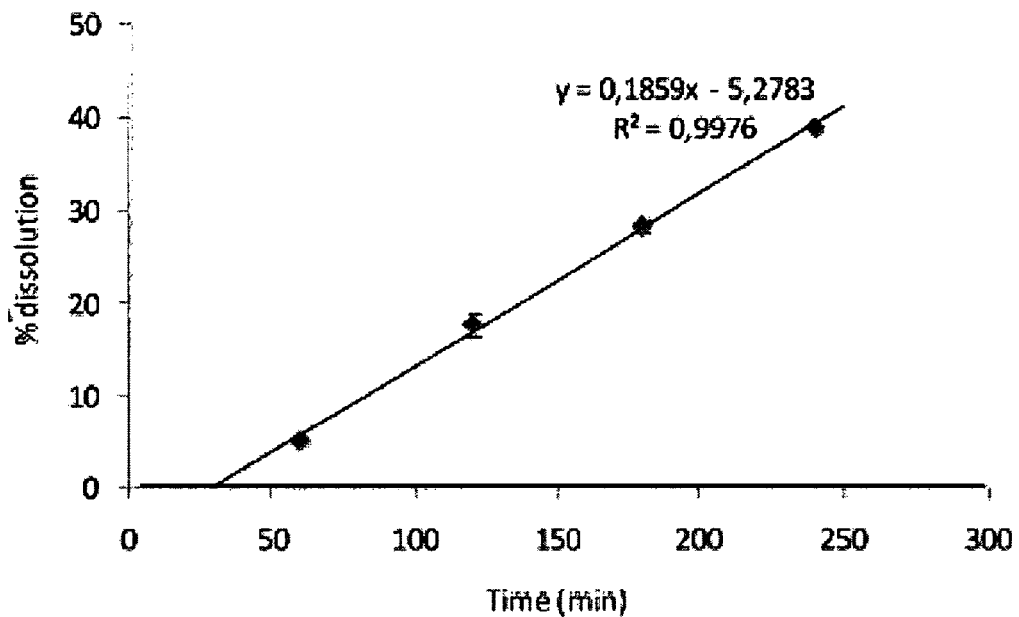
FIG. 10 shows the erosion profile (dissolution) of PG-LA1 (Poloxamer 407 in lactic acid solution) without imiquimod (top) and with imiquimod (TMX PG-LA1) (bottom) over time.
Figure 10:
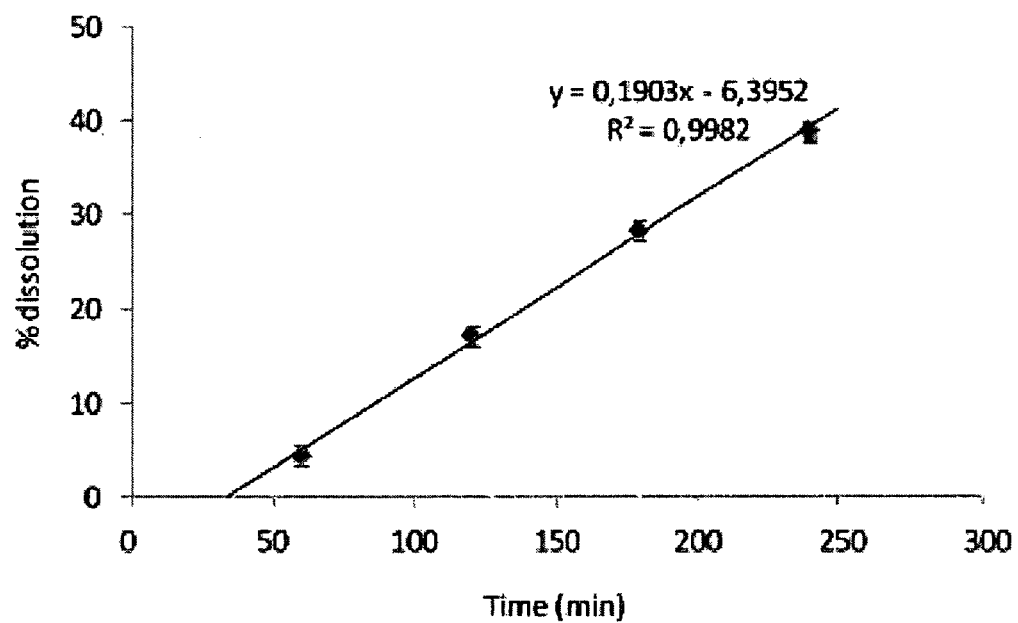

The obtained results are depicted in FIG. 10 (the values are the mean of three replicates). It can be noted that the erosion profile of the considered systems are quite similar (p>0.973), indicating that the drug does not affect the polymer erosion. The dissolution/erosion of both the systems was a zero-order kinetic process, almost up to 4 hours (about 40% of erosion): an identical kinetic was observed by Zhang, but the rate of the process was higher (about 0.26% $min^{-1}$) than that we obtained (about 0.19% $min^{-1}$). Zhang observed that the pH of the dissolution medium had a negligible influence on the gel dissolution and used phosphate buffer solutions of different pH as solvent far the polymer. The present findings could be associated to the low pH of formulations or to the interactions of lactic acid with the poloxamer.

Further, during the dissolution/erosion experiment with imiquimod PG-LA 01 formulation, no separation/precipitation of the drug could be observed.

4. Example

Imiquimod Diffusion/Release Experiments 4.1. Compositions and Experimental Conditions
4.1.1. Compositions
Imiquimod PPG-LA 01

| Imiquimod | 0.90 g |
| Poloxamer 407 | 22.50 g |
| Poloxamer 188 | 2.50 g |
| Lactic acid solution (0.135M) | 74.02 g |

Imiquimod PG-LA 01

| Imiquimod | 0.90 g |
| Poloxamer 407 | 20.00 g |
| Lactic acid solution (0.125M) | 79.02 g |

PG-LA01

| Poloxamer 407 | 20.00 g |
| Lactic acid solution (0.125M) | 79.02 g |

4.1.2. Experimental Conditions

The imiquimod diffusion/release experiments have been performed with Franz cells with an effective diffusion area of 1.76 $cm^2$ and a receiving compartment volume of 14 ml: the donor compartment contained about 2 g of gel formulation, while the receiving one was filled with 0.1 M lactic acid solution (pH=3.5). Between the two compartments, a cellulose acetate membrane (MWCO=23000) was interposed. The experiments were carried out at 37° C. using a re-circulating bath and the fluid in the receptor chamber was stirred continuously at 300 rpm.

At prefixed time intervals, the receiving phase was completely withdrawn and substituted by fresh acid solution. The receiving solution was submitted to UV analysis for imiquimod.

4.2. Results and Discussion

The flux of imiquimod trough the artificial barrier is high ($1.95 \times 10^{-6}$ g·cm$^{-2}$·s$^{-1}$) and constant (almost for the first hour) suggesting that the transfer of the drug through the membrane does not affect the imiquimod kinetics through the poloxamer gels.

Figure 11:
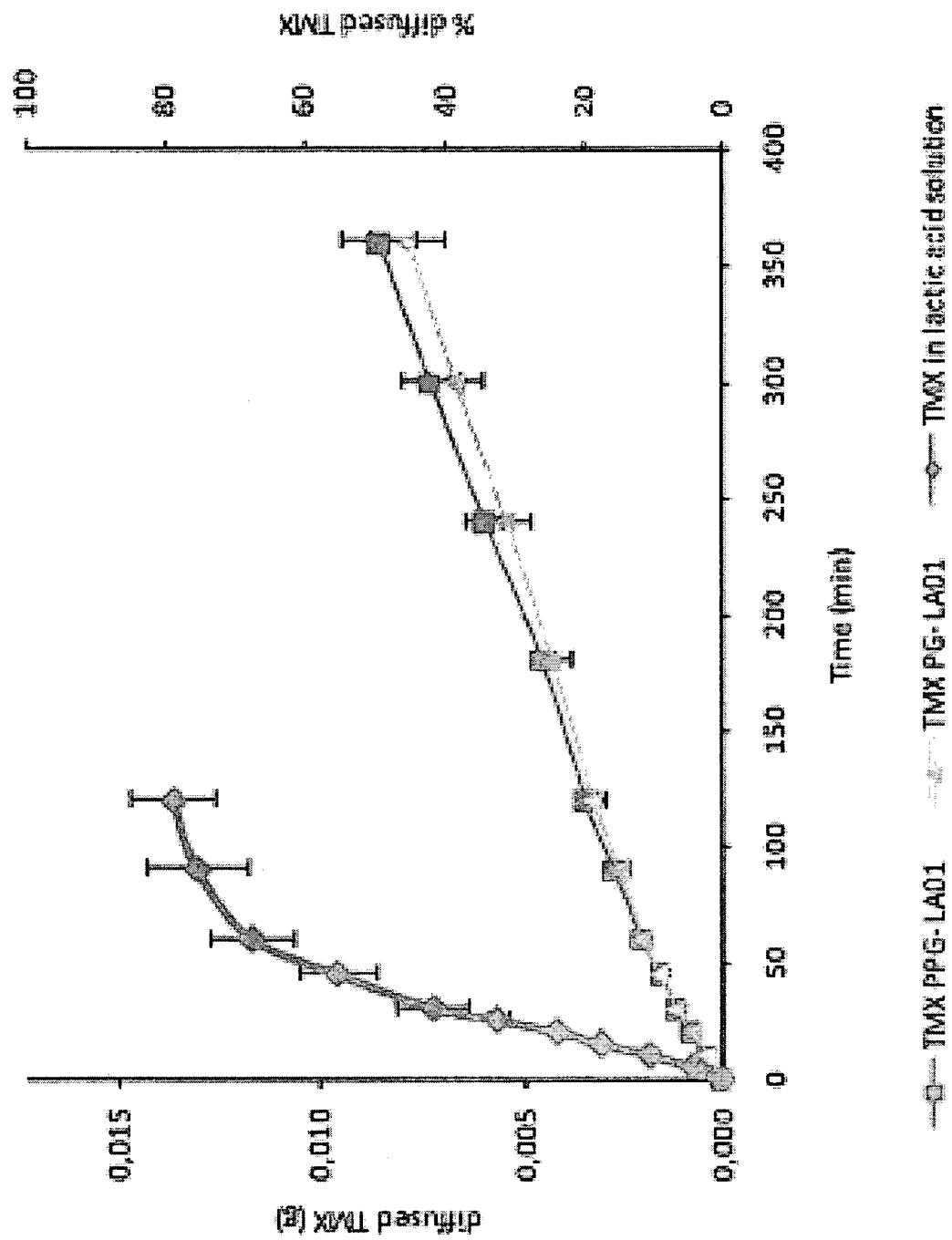
FIG. 11 shows the imiquimod (TMX) diffusion profiles (g) passing the cellulose membrane as a result of gel formulations prepared with 0.1 M lactic acid and Poloxamer 407 (PG) or Poloxamer 407/Poloxamer 188 mixture (PPG): in the same figure, the diffusion of imiquimod (TMX) in 0.1 M lactic acid solution without gel formulation is given for comparative purposes.

The imiquimod profiles of gel formulations are very different from that of the solution, but very similar between them. Imiquimod diffuses through the gel matrix with relatively high rate: after 6 hours, about 44.4% for imiquimod PG-LA 01 formulation and about 48.3% for Imiquimod PPG-LA01 was in the receiving phase of the Franz cell. The drug diffusion profiles for both the gel formulations are linear, suggesting pseudo-zero order kinetics: the imiquimod fluxes through the gel matrix are $2.00 \times 10^{-7}$ g·cm$^{-2}$·s$^{-1}$ for imiquimod PG-LA 01 and $2.19 \times 10^{-7}$ g·cm$^{-2}$·s$^{-1}$ for imiquimod PPG-LA01 system (FIG. 11).

These findings lead to the conclusion that the drug diffusion rate through both the examined systems does not differ significantly and demonstrate that the composition of the jellifying material have no relevant effect on the imiquimod diffusion in the gel: the small molecular dimensions (low molecular weight) of the active favors its movement through the micellar structure of gel.

As the experiment proceeds, the polymer gradually dissolves in the liquid that passes the membrane. The flux of the liquid, in counter-current to the drug, could alter the diffusion of the active molecule from donor to receiving compartment. However, this effect is negligible: the flux of imiquimod through the membrane is ten times higher than its flux through the poloxamer systems.

5. Example

Imiquimod Penetration Test

5.1. Compositions and Experimental Conditions

5.1.1. Compositions

The compositions submitted to the test were:
- 0.9% Imiquimod—15% HP-β-CD in 0.1 M lactic acid solution
- 0.9% Imiquimod in 19% Poloxamer 407 gel containing 15% HP-β-CD (0.1 M lactic acid)
- 0.9% Imiquimod in liposome dispersion (1% soybean lecithin in 0.1 M lactic acid solution)

5.1.2. Experimental Conditions

The bladder of 6-9 months-aged female pigs was used: immediately after the excision, the urethra was cut away and the bladder epithelium (BE) was sectioned to obtain pieces of about 3 cm$^2$ area. Each portion of epithelium was mounted between the compartments of a Franz cell with the internal surface faced up. As receiving phase (bottom compartment), 0.1 M phosphate buffer solution (pH 7.4) was used: it was maintained under stirring (about 300 rpm) at 37° C. during the experiment. One of the reported formulations represents the donor phase (top compartment): the formulation (2 g) was introduced in the donor compartment after the temperature of the apparatus attains 37° C. temperature. At the end of the experiment (4 hours after the beginning), BE removed from the diffusion cell was thoroughly washed with distilled water to remove excess formulation and carefully wiped with tissue paper. Then BE was frozen and sectioned using a cryostatic microtome. Five successive BE sections (each of 100 m thickness) were introduced in a tube, added of 5 ml lactic acid (92%) and maintained under shaking overnight. The liquid phase was filtered (0.22 μm) and assayed by HPLC for imiquimod.

5.2. Results

FIG. 12 depicts the obtained results reporting the amount of imiquimod recovered in BE after 4 hours of contact with the formulation (data are normalized for the absorption area). Data are the mean of 3 experiments (solution and liposomes) or 6 experiments (gel formulation).

The gel formulation affects the absorption of imiquimod into the bladder epithelium: the amount of active released from the gel and recovered in BE is lower than that released from the solution. It is interesting to notice that the amount of imiquimod formulated in liposomes and present in the BE is greater than that from solution: this result suggests a promotion effect of lipid vesicles on the absorption of the drug.

6. Example

Solubility, Density and Viscosity of Different Compositions Comprising Imiquimod

6.1. Solubility

6.1.1. Compositions

The solubility of imiquimod has been determined in different solvent systems:
- lactic acid solutions—0.025, 0.05, 0.1 and 0.2 M
- 0.1 M lactic acid solution containing 5 or 15% of HP-β-CD
- 0.1 M lactic acid solution containing 5, 16 and 20% Poloxamer 407
- 0.1 M lactic acid solution containing 5 or 15% of HP-β-CD and 16% Poloxamer 407
- solutions of 0.1 M glycolic acid, tartaric acid and glutamic acid
- DMSO
- N-methyl-pyrrolidone
- PEG 400

6.1.2. Experimental Conditions

An amount exceeding the drug solubility (2 g) has been added of the different solvent systems (50 ml) and stirred for 24 hours (400 rpm) at 25° C. The dispersions have been centrifuged at 10,000 rpm for 10 minutes and the liquid phases collected and stored at room temperature until analysed. The imiquimod concentration in these solutions was spectrophotometrically (λ=319 nm) determined after appropriated dilution.

6.1.3. Results and Discussion

In Table 8, the obtained results are reported. The values are the mean of 3 determinations. Imiquimod solubility in maleic acid solution will be determined in few days.

TABLE 8

Imiquimod solubility study in different solvent systems

| Formulation | % w/w imiquimod | pH |
| --- | --- | --- |
| LA 0.025M | 0.33 | 3.93 |
| LA 0.05M | 0.58 | 3.81 |
| LA 0.1M | 1.18 | 3.73 |
| LA 0.2M | 2.20 | 3.52 |
| 5% CD LA 01 | 1.23 | 3.90 |
| 15% CD LA 01 | 1.37 | 4.03 |
| 5% PF127 LA 01 | 1.19 | 3.92 |
| 16% PF127 LA 01 | 1.10 | 3.99 |
| 20% PF127 LA 01 | 1.04 | 4.16 |
| 5% CD-16% PF127 LA 01 | 1.15 | 4.05 |
| 15% CD-16% PF127 LA 01 | 1.22 | 4.25 |
| Glycolic acid 0.1M | 0.68 | 3.82 |
| Tartaric acid 0.1M | 0.01 | 2.48 |
| Glutamic acid 0.072M | 0.54 | 3.95 |
| DMSO | 0.09 | n.d. |

TABLE 8-continued

Imiquimod solubility study in different solvent systems

| Formulation | % w/w imiquimod | pH |
|---|---|---|
| N-Methyl-pyrrolidone | 0.16 | n.d. |
| PEG 400 | 0.03 | n.d. |

The obtained results indicate that:
- a linear relationship between lactic acid and imiquimod exists (FIG. 13, top): the solubility of the drug increases for increasing concentration of the carboxylic acid
- cyclodextrin increases the solubility of imiquimod: also in this case, the increment of dissolved drug is linearly related to the amount of cyclodextrin employed (FIG. 13, bottom).
- Poloxamer 407 has a negative effect on the drug solubility: as the percentage of polymer increases, the concentration of imiquimod in solution decreases.
- When both Poloxamer 407 and cyclodextrin are present in the formulation, the opposite effects of these components are balanced and imiquimod solubility was not substantially modified respect to that of 0.1 M lactic acid solution.
- In presence of carboxylic acids like glycolic, tartaric and glutamic ones the drug solubility is lower than with lactic acid (glutamic acid was used at a concentration corresponding to its solubility, i.e. 10.6 g/l). The imiquimod solubility observed in presence of tartaric acid can be explained considering the structural differences of this (di-carboxylic) acid respect to the other acidic compounds (hydroxyl-carboxylic acids): the lower solubility value suggests the involvement of the alcoholic function in the formation of drug/hydroxy-carboxylic acid adduct. For glutamic acid, the role of the hydroxyl group is played by the primary amino-group of the amino acid.
- The solubility of imiquimod in hydrophilic, non-aqueous solvent is very low.

6.2. Density 6.2.1. Compositions

The density evaluation was carried out on 5 ml of the following compositions:
- 0.1 M lactic acid solution containing 16% Poloxamer 407
- 0.1 M lactic acid solution containing 5 or 15% of HP-β-CD and 16% Poloxamer 407
- 0.1 M lactic acid solution containing 5 or 15% of HP-β-CD, 16% Poloxamer 407, and 0.5% imiquimod
- 0.1 M lactic acid solution containing 5 of HP-β-CD and 0.5% imiquimod 6.2.2. Experimental Conditions 5 measurements were done and the average values and standard deviations were calculated 6.2.3. Results

TABLE 9

Determination of the density

| formulation | density ± S.D. (g/ml) |
|---|---|
| 16% PF127 LA 01 | 1.0155 ± 0.0032 |
| 5% CD-16% PF127 LA 01 | 1.0299 ± 0.0039 |
| 15% CD-16% PF127 LA 01 | 1.0639 ± 0.0040 |
| 5% CD-16% PF127 LA 01 - 0.5% imiquimod | 1.0359 ± 0.0033 |
| 15% CD-16% PF127 LA 01 - 0.5% imiquimod | 1.0670 ± 0.0023 |
| 5% CD LA 01 - 0.5% imiquimod | 1.0158 ± 0.0036 |

6.3. Viscosity 6.3.1. Compositions

The viscosity was determined on the following compositions:
- gel containing 16% of Poloxamer 407
- gel containing 16% of Poloxamer 407 and 15% HP-β-CD
- gel containing 16% of Poloxamer 407 and 5% HP-β-CD
- 0.5% imiquimod lactic acid (0.1 M) solution containing 15% HP-β-CD
- 0.5% imiquimod lactic acid (0.1 M) solution containing 5% HP-β-CD
- 0.5% imiquimod gel formulation containing 16% of Poloxamer 407 and 15% HP-β-CD
- 0.5% imiquimod gel formulation containing 16% of Poloxamer 407 and 5% HP-β-CD 6.3.2. Results In Table 10 the viscosity of the other systems are reported. The values are the mean of 3 measurements±S.D.

TABLE 10 gel viscosity (20 RPM) at 10, 25 and 37° C.

| | Viscosity at 20 RPM (cP) ± S.D. | | |
|---|---|---|---|
| formulation | 10° C.[1] | 25° C.[1] | 37° C.[2] |
| 16% PF127 LA01 | 22.47 ± 0.45 | 63.03 ± 1.93 | 1103.00 ± 82.31 |
| 5% CD-16% PF127 LA 01 | 31.90 ± 0.35 | 65.80 ± 1.08 | 571.77 ± 94.73 |
| 15% CD-16% PF127 LA 01 | 64.27 ± 1.33 | 76.43 ± 0.47 | 573.33 ± 50.14 |
| 5% CD-16% PF127 LA 01 - 0.5% imiquimod | 32.27 ± 0.40 | 68.20 ± 1.82 | 963.05 ± 3.32 |
| 15% CD-16% PF127 LA 01 - 0.5% imiquimod | 70.33 ± 0.51 | 93.47 ± 2.64 | 795.13 ± 110.56 |

[1]Spindle SC18
[2]Spindle SC29

For the studied formulations, a significantly different behaviour has been observed at different temperatures: at 10 and 25° C., the addiction of cyclodextrin and/or imiquimod to the polymeric solution leads to the increase of the viscosity, while at 37° C., the viscosity is lowered by cyclodextrin and increased by the drug.

7. Example

Solubility of Imiquimod in Salt Solutions and in Artificial Urine Solution 7.1. Compositions The solubility of imiquimod contained in gel formulations was evaluated in several salts solutions. The study was performed on imiquimod formulations constituted of:

0.9% Imiquimod Gel

| Poloxamer 407 | mg | 160.162 |
|---|---|---|
| HPβCD | mg | 50.025 |
| Imiquimod | mg | 9.005 |
| Lactic acid (90.3%) | mg | 10.017 |
| Water for Injection q.b. | mg | 1000.000 |

0.5% Imiquimod Gel

| | | |
|---|---|---|
| Poloxamer 407 | mg | 160.157 |
| HPβCD | mg | 50.031 |
| Imiquimod | mg | 5.002 |
| Lactid acid (90.3%) | mg | 10.024 |
| Water for Injection q.b. | mg | 1000.000 |

0.1% Imiquimod Gel

| | | |
|---|---|---|
| Poloxamer 407 | mg | 160.098 |
| HPβCD | mg | 50.013 |
| Imiquimod | mg | 1.007 |
| Lactid acid (90.3%) | mg | 10.028 |
| Water for Injection q.b. | mg | 1000.000 |

As solvents for the drug the following solutions were employed:

| | |
|---|---|
| Water | |
| Na sulphate | 10 mM |
| K phosphate | 14 mM |
| Na bicarbonate | 25 mM |
| AUS | |

The pH was corrected to 6.50±0.05 with 1 HCl

Artifical Urine Solution (AUS) had the following composition:

| | |
|---|---|
| Na bicarbonate | 25 mM |
| Urea | 170 mM |
| Uric acid | 0.4 mM |
| Creatinine | 7 mM |
| Na chloride | 90 mM |
| Na sulphate | 10 mM |
| $K_2$ hydrogen phosphate | 7 mM |
| K di-hydrogen phosphate | 7 mM |
| $NH_4$ chloride | 25 mM |

The pH was corrected to 6.50±0.05 with 1M HCl]

7.2. Experimental Conditions

Prefixed volumes of formulation and solvent were transferred in a 10 ml flask in order to obtain mixtures where the solvent/formulation volume ratio were 0.5, 1, 5 and 10. These systems were maintained under agitation for different time periods (25, 50, 240 and 240 minutes for 0.5, 1, 5 and 10 solvent/formulation volume ratio systems respectively). The selected times correspond to presumable times of urine formation (urine production rate=1 ml/min) (for 10 solvent/formulation volume ratio system the applied time period of 240 minutes is lower than expected because the calculated time (500 minutes) exceeds the effective time of contact of the formulation with the bladder). After that, the pH of each system was measured. The systems were centrifuged at 5000 rpm for 15 minutes and the recovered liquid fractions submitted to spectrophotometric analysis (A=319 nm) for imiquimod content.

7.3. Results and Discussion

The results (means of 3 replicas) are reported as pH units and as imiquimod precipitated percentages in the following tables 11 and 12.

TABLE 11 pH Measurements

| Sol/formul ratio | | | | $H_2KO_4P/$ | | | |
|---|---|---|---|---|---|---|---|
| 0.9% Imiquimod gel | solution | $H_2O$ | $SO_4^{2-}$ | $HK_2O_4P$ | $HCO^{3-}$ | A.U.S. | 0.9% gel |
| 0 | | | | 6.53 | 6.50 | 6.52 | 6.51 | 3.40 |
| 1 | 0.5 | 3.34 | 3.30 | 3.38 | 3.48 | 3.56 | |
| 1 | 1 | 3.25 | 3.31 | 3.36 | 3.50 | 3.80 | |
| 1 | 5 | 4.50 | 3.28 | 3.57 | 4.49 | 5.73 | |
| 1 | 10 | 3.30 | 3.30 | 3.89 | 6.10 | 6.33 | |

| Sol/formul ratio | | | | $H_2KO_4P/$ | | | |
|---|---|---|---|---|---|---|---|
| 0.5% Imiquimod gel | solution | $H_2O$ | $SO_4^{2-}$ | $HK_2O_4P$ | $HCO^{3-}$ | A.U.S. | 0.5% gel |
| 0 | | | | 6.53 | 6.50 | 6.52 | 6.51 | 3.21 |
| 1 | 0.5 | 3.28 | 3.30 | 3.33 | 3.49 | 3.72 | |
| 1 | 1 | 3.36 | 3.35 | 3.42 | 3.66 | 4.06 | |
| 1 | 5 | 3.26 | 3.30 | 3.68 | 5.10 | 6.41 | |
| 1 | 10 | 3.33 | 3.35 | 4.08 | 6.55 | 6.60 | |

| Sol/formul ratio | | | | $H_2KO_4P/$ | | | |
|---|---|---|---|---|---|---|---|
| 0.1% Imiquimod gel | solution | $H_2O$ | $SO_4^{2-}$ | $HK_2O_4P$ | $HCO^{3-}$ | A.U.S. | 0.1% gel |
| 0 | | | | 6.53 | 6.50 | 6.52 | 6.51 | 3.21 |
| 1 | 0.5 | 2.88 | 2.85 | 2.91 | 3.06 | 3.31 | |
| 1 | 1 | 2.80 | 2.81 | 2.95 | 3.25 | 3.62 | |
| 1 | 5 | 2.90 | 2.94 | 3.34 | 4.88 | 6.14 | |
| 1 | 10 | 3.02 | 3.09 | 3.78 | 8.29 | 6.53 | |

TABLE 12

| | Imiquimod precipitation | | | | |
|---|---|---|---|---|---|
| | Imiquimod precipitated (% p/p) | | | | |
| Sol/formul ratio (v/v) | | 0.5 | 1 | 5 | 10 |
| | Sulphate Solution | | | | |
| Initial | 0.9 | 22.46 | 47.56 | 83.54 | 75.84 |
| % | 0.5 | 43.17 | 69.28 | 71.54 | 68.56 |
| Imiquimod | 0.1 | 0.00 | 0.00 | 0.00 | 0.00 |
| | Bicarbonate Solution | | | | |
| Initial | 0.9 | 0.00 | 0.00 | 43.22 | 99.76 |
| % | 0.5 | 0.00 | 0.00 | 74.82 | 99.77 |
| Imiquimod | 0.1 | 0.00 | 1.86 | 0.00 | 98.84 |
| | Phosphate Buffer Solution | | | | |
| Initial | 0.9 | 0.00 | 0.00 | 0.33 | 4.29 |
| % | 0.5 | 2.21 | 0.00 | 1.30 | 2.19 |
| Imiquimod | 0.1 | 0.00 | 0.26 | 0.00 | 1.29 |
| | Water | | | | |
| Initial | 0.9 | 30.36 | 0.00 | 2.60 | 3.06 |
| % | 0.5 | 0.39 | 0.00 | 0.74 | 2.74 |
| Imiquimod | 0.1 | 0.00 | 0.00 | 0.00 | 0.00 |
| | Artificial Urine Solution | | | | |
| Initial | 0.9 | 23.23 | 44.02 | 96.60 | 98.92 |
| % | 0.5 | 38.89 | 57.75 | 97.93 | 98.63 |
| Imiquimod | 0.1 | 0.00 | 0.00 | 84.29 | 86.35 |

The pH of the different solutions (except AUS) has been corrected to about 6.5. It has to be noted that
- a small volume of solution (irrespective of the kind of salt) is not able to control the pH of the mixture.
- A.U.S. and bicarbonate solution at high volume ratio with the formulation showed a pH not significantly different from their initial value.
- the amount of drug present in the formulation did not substantially alter the buffering ability of AU.S and Bicarbonate solution: a slight decrease of pH has been observed as the percentage of imiquimod in the formulation decreased (increase of free lactic acid).

Dilution with water did not determine a significant precipitation of the drug, independently from the gel/solution ratio: an exception is represented by the system water/0.9% imiquimod gel (0.5:1 volume ratio) for which a consistent decrease of solubilized drug concentration has been observed (more than 30%).

With phosphate buffer solution the drug precipitation was not macroscopically evident: max 4.29% of decrease of drug in solution for the formulation containing the highest amount of imiquimod (0.9%) and at the maximum dilution ratio.

Among the anions, the bicarbonate one determined the greatest precipitation of drug: at 10:1 volume ratio an almost complete precipitation of imiquimod has been observed for all formulations.

The sulphate solution separated the drug from 0.9% and 0.5% gels, but not from the 0.1% drug system: for the highest drug-containing gel, a parabolic relationship between imiquimod precipitated percentage and dilution ratio was present.

The results obtained with Artificial Urine Solution can be ascribed primarily to the presence of bicarbonate and sulphate ions, while an additive/synergistic effect of same other component of AUS cannot be excluded.

8. Example

Comparison of Imiquimod Formulations Containing Different Poloxamer Percentages 8.1. Compositions The experimental work was aimed to compare some chemico-physical characteristics of imiquimod formulations that contain different amounts of poloxamer 407 and of drug.

The investigated systems had the following compositions:
Formulation 0.5%-16

| Poloxamer 407 | 160.06 mg |
|---|---|
| Imiquimod | 5.02 mg |
| HPβCD | 50.06 mg |
| Lactic acid (90.3%) | 10.00 mg |
| Water for Injection q.b. | 1000.00 mg |

Formulation 0.1%-16

| Poloxamer 407 | 160.05 mg |
|---|---|
| Imiquimod | 1.01 mg |
| HPβCD | 50.02 mg |
| Lactid acid (90.3%) | 10.00 mg |
| Water for Injection q.b. | 1000.00 mg |

Formulation 0.5%-10

| Poloxamer 407 | 160.03 mg |
|---|---|
| Imiquimod | 5.01 mg |
| HPβCD | 50.06 mg |
| Lactid acid (90.3%) | 10.00 mg |
| Water for Injection q.b. | 1000.00 mg |

Formulation 0.1%-10

| Poloxamer 407 | 100.06 mg |
|---|---|
| Imiquimod | 1.04 mg |
| HPβCD | 50.01 mg |
| Lactid acid (90.3%) | 10.00 mg |
| Water for Injection q.b. | 1000.00 mg |

8.2. Results

The viscosity and the pH of these formulations were determined at 25 and 37° C. and the results are reported in the following table 13:

| | Viscosity at 25° C. (*) | | | Viscosity at 37° C. (**) | | | |
|---|---|---|---|---|---|---|---|
| Formulation | Rotation speed (rpm) | Torsion force (%) | Viscosity (cP) | Rotation speed (rpm) | Torsion force (%) | Viscosity (cP) | pH |
| F. 0.5%-16 | 20 | 47.8 | 2221 | 8 | 72.1 | 270.7 | 3.26 |
| F. 0.1%-16 | 20 | 50.3 | 2350 | 15 | 83.1 | 166.2 | 2.99 |
| F. 0.5%-10 | 35 | 12.5 | 334.8 | 35 | 11.9 | 10.2 | 3.23 |
| F. 0.1%-10 | 35 | 12.7 | 340.0 | 35 | 11.5 | 9.86 | 2.60 |

(*) Spindle nr. 25
(**) Spindle nr. 18

9. Example

In Vitro Evaluation of the Toxicity of Imiquimod Formulation on Pig Urinary Bladder Epithelium

9.1. Material and Methods
9.1.1. Study Design

The study was carried out on bladder epithelium from two pigs using the following treatments:
- 0.1% imiquimod formulation (a mixture of 16% Poloxamer, 5% Hydroxypropyl Beta cyclodextrin, in 0.1 M lactic acid)
- Vehicle (a mixture of 16% Poloxamer, 5% Hydroxypropyl Beta cyclodextrin, in 0.1 M lactic acid)
- 0.9% NaCl solution Portions of pig bladder were placed between the donor (treatment) and acceptor chambers of Franz cells. The receiving medium PBS (pH 7.4) was used in all the experiments. One hour after the experiment started, the receiving medium was withdrawn and analyzed for imiquimod content. The bladder was recovered; the treated portion was separated and divided in two parts: one was fixed in formalin, embedded, sectioned and stained (H&E) for histological examination; and the other part was submitted for drug extraction and analysis.

9.1.2. Peer Review

The histopathological examination was carried out on five urinary bladder sections i.e. 2 slides from pig 1 (labelled imiquimod 1 and vehicle 1), 2 slides from pig 2 (labelled imiquimod 2 and vehicle 2) and one slide with the NaCl solution (labelled control).

The slides were examined primarily for urothelial integrity and any sub-mucosal changes including inflammation.

9.2. Results and Conclusion

The urothelium and sub-mucosal tissue appeared to be normal in all slides examined. There were no significant differences between treatments (Data not shown).

9.3. Imiquimod Penetration Experiments for Toxicity Evaluation

9.3.1. Aim

In order to evaluate the penetration of the active molecule into the pig vesical epithelium, a series of in-vitro penetration experiments was carried out.

The investigated imiquimod formulations were:
- 0.5% Imiquimod in 0.1 M lactic acid solution
- 0.5% Imiquimod—5% HP-β-CD in 0.1 M lactic acid solution
- 0.5% Imiquimod in 16% poloxamer 407 gel
- 0.5% Imiquimod—5% HP-β-CD in 16% poloxamer 407 gel The composition of systems was the following:

0.5% Imiquimod in 0.1 M Lactic Acid Solution

| | |
|---|---|
| Imiquimod | 5.020 mg |
| Lactic acid (90.3%) | 10.020 mg |
| Water for Injection q.b. | 1000.00 mg |

0.5% Imiquimod—5% HP-β-CD in 0.1 M Lactic Acid Solution

| | |
|---|---|
| HP-β-CD | 50.080 mg |
| Imiquimod | 5.020 mg |
| Lactic acid (90.3%) | 10.080 mg |
| Water for Injection q.b. | 1000.000 mg |

0.5% Imiquimod in 16% Poloxamer 407 Gel

| | |
|---|---|
| Poloxamer 407 | 160.020 mg |
| Imiquimod | 5.000 mg |
| Lactic acid (90.3%) | 10.100 mg |
| Water for Injection q.b. | 1000.000 mg |

0.5% Imiquimod—5% HP-β-CD in 16% Poloxamer 407 Gel

| | |
|---|---|
| Poloxamer 407 | 160.162 mg |
| HP-β-CD | 50.025 mg |
| Imiquimod | 5.005 mg |
| Lactic acid (90.3%) | 10.017 mg |
| Water for Injection q.b. | 1000.000 mg |

9.3.2. Method

The bladder, from a 6-9 months-aged female pig, was sectioned and mounted between the compartments of a Franz cell with the internal surface faced up. In all the experiments, 0.1 M phosphate buffer solution (pH 7.4) was used as receiving phase: it was maintained under stirring (about 300 rpm) at 37° C. during the experiment. An imiquimod-containing formulation (2 g) represented the donor phase.

At the end of the experiment (4 hours after the beginning), bladder epithelium (BE) removed from the diffusion cell was thoroughly washed with distilled water to remove excess formulation and carefully wiped with tissue paper. Then BE was frozen and sectioned using a cryostatic microtome. Five successive BE sections (each of 100 μm thickness) were introduced in a tube, added of 5 ml lactic acid (92%) and maintained under shaking overnight. The liquid phase was filtered (0.22 pm) and assayed by HPLC for imiquimod.

9.3.3. Results

FIG. 15 depicts the obtained results reporting the amount of imiquimod recovered in BE after 4 hours of contact with the formulation (data are normalized for the absorption areal. Data are the mean of 3 experiments.

10. Example

Pharmacokinetics and Toxicity of Intravesical Imiquimod: a Preclinical Study in Pigs

10.1. Introduction

To test whether bladder cancer might be a suitable target for imidazoquinoline(amines) therapy TLR-7 expression in human bladder cancer and normal bladder tissue was studied. Pig tissue samples were studied for model validation. Thereafter, to test the potential and risks of imidazoquinoline(amines) when used intravesically, an animal study was performed in which three different intravesical formulations of imiquimod and a vehicle control were tested. Animal well-being, pharmacokinetic properties, cytokine production and bladder wall histology was studied.

10.2. Animals, Material and Methods
10.2.1. Detection of TLR-7 Expression Fifteen formalin-fixed, paraffin embedded human bladder cancer specimens and six normal bladder specimens were stained for TLR-7 by Mosaic Laboratories, LLC (Lake Forest, Calif., USA). Additionally, 28 different normal human tissue specimens (other than bladder) were stained for TLR-7 expression. In addition, porcine bladder, tonsil, heart, liver, spleen and kidney tissue samples were tested.

The staining intensity of each specimen was judged relative to the intensity of a control slide containing an adjacent section stained with an irrelevant species- and isotypematched antibody. Staining of the section labeled with the negative reagent control was considered "background." Sections were scored as follows: 0 no staining relative to background, 1+ weak staining, 2+ moderate staining, and 3+ strong staining. Total positive staining (the sum of all staining at 1+, 2+, and 3+ was recorded for each specimen. The H-score was calculated based on the summation of the product of percent of cells stained at each intensity using the following equation: (3×% cells staining at 3+)+(2×% cells staining at 2+)+(1×% cells staining at 1+). The H-score values ranged from 0-300.

10.2.2. Pig Model

Animal procedures were performed according to the protocol approved by the Institutional Animal Care and Use Committee (IACUC, Radboud University Nijmegen Medical Centre, The Netherlands) and in compliance with national and European regulations. Female pigs (Dutch Landrace) were used for this study. The urogenital tract of the pig closely resembles the human urogenital system, and the shape of the penis and the preputial diverticulum prevent transurethral catheterization of a male pig. The sows were housed in special swine stainless steel battery cages and fed with universal swine food. The pigs were divided into four groups of six animals. Experimental procedures were performed under general anesthesia. Premedication contained a mixture of 10 mg/kg ketamine and 0.5 to 1.0 mg/kg midazolam i.m. in one shot. Sedation maintenance was done by the same mixture in half the dosage every 45 minutes. The bladder was emptied without suction trauma prior to the start of treatment (via 12 French Foley catheter) and 50 mL of the study drug was instilled intravesically. Animals received a solution of imiquimod 0.5% dissolved in 0.1 M lactic acid (group 1); a solution of imiquimod 0.5% dissolved in 0.1 M lactic acid, poloxamer 407 16% as emulsifying agent and HPβCD (hydroxypropyl-β-cyclodextrin) 15% as stabilizing agent (group 2); a solution of imiquimod 0.5% dissolved in 0.1 M lactic acid, poloxamer 407 16% and HPβCD 5% (group 3) or a vehicle control (0.1 M lactic acid) (group 4). The catheter was clamped and the instillation fluid was retained in the bladder for 60 minutes, after which the bladder was emptied. The bladder was not rinsed after emptying.

Blood samples were obtained for pharmacokinetic analyses (PK), cytokine (IL-6) measurements, creatinine measurements and full blood cell count. The cephalic vein or internal, external, or communal jugular vein was punctured, depending on puncture angle and depth of needle penetration.

Samples for blood count and creatinine measurement were collected in 3-mL potassium EDTA tubes and 3 mL lithium heparin tubes with gel divider, respectively, before instillation and 60 minutes, 24 hours and 1 week (just before cystectomy) after the beginning of instillation. The samples were stored on ice and transferred to the laboratory for analysis.

Blood samples for pharmacokinetic analysis and cytokine measurement were collected in 4 mL lithium heparin tubes with gel divider before instillation of the study drug and 15, 30, 60, 120, 240 and 480 minutes after the beginning of drug instillation and also just before cystectomy. The samples were transferred on ice to the laboratory for plasma processing within 30 minutes. The blood was centrifuged for 15 minutes at 3,200 rpm at 4° C., plasma was collected for PK and cytokine analysis, stored at −80° C., and shipped on dry ice for analysis.

The post-treatment evacuated bladder content and the evacuated urine just before necropsy were collected for analysis of imiquimod concentration. Urine was frozen immediately and stored in plastic tubes at −80° C., and shipped on dry ice for imiquimod determination. Dipstick urinalysis was performed on the evacuated pre- and post-treatment urine and on the urine collected just before necropsy. Imiquimod concentrations in plasma and urine was determined by CHIMAN s.r.l. (Rottofreno, Italy) by liquid chromatography-mass spectroscopy/mass spectroscopy (LC-MSMS). Plasma samples for IL-6 measurement were analyzed by Areta International s.r.l. (Gerenzano, Italy) using the "Quantikine Porcine IL-6" (P6000; R&D System) kit.

Body temperature was measured rectally before and 1, 8 and 24 hours and one week after starting treatment. The well being of the animals was monitored by experienced staff by a selected protocollary list of possible signs and symptoms of toxicity before the experiment, just after the instillation and just before cystectomy.

24 hours after treatment three animals per group were sacrificed and cystectomised and 7 days after treatment the remaining animals underwent the same procedure. Material from the bladders was collected and processed for histology as follows: Bladder biopsies of 1 cm$^2$ were taken from dome, trigone, right lateral wall, and left lateral wall and transferred into 10% formalin in PBS. Material was embedded in paraffin, sectioned, and stained with H&E. The slides were evaluated for signs of inflammation and allergic reaction in submucosa and mucosa. Microscopic abnormalities were classified as no reaction, mild, moderate or severe reaction.

10.3. Results 10.3.1. TLR-7 Expression

TLR-7 expression of the 15 human bladder cancer specimens demonstrated positive staining in all samples ranging from 70% to 100% with an average of 90% (SD=9%). The most intense staining was nuclear membrane/perinuclear and weaker cytoplasmic staining (FIG. 16) The H-score ranged from 90 to 155 with an average of 127 (SD=23). Positive staining was also observed in 6 normal bladder epithelia specimens ranging from 80% to 100% with an average of 95% (SD=8%). H-score ranged from 100 to 230 with an average of 179 (80=55). TLR-7 expression was observed in almost all non-bladder tissues examined (data not shown), most prominently in lymphoid tissue. Lack of staining was observed in heart and smooth muscle. TLR-7 expression in pig tissues (FIG. 17) was similar to the corresponding human tissues.

10.3.2. Pig Experiment

Twenty-four pigs with a mean weight of 57.1 kg (range, 40.0-85.0 kg) were divided into four groups of six pigs treated with various formulations of imiquimod as a single 50-minute intravesical instillation. Throughout the one week follow-up period after instillation (3 pigs per group) no deterioration of animal well-being was observed. Minor signs of toxicity possibly due to the study drug were observed in four pigs (i.e. low food intake in three pigs, group 1, 2 and 4 and loose stool in one pig, group 1). There were no other signs of impaired animal well-being.

Post-treatment body temperature was not influenced by the instillation of the study drug and comparable with pre-treatment body temperature for all treatment groups. Although a slight increase in creatinine levels was observed one week post-instillation in group 1 and 2, possibly indicating slight kidney impairment, no obvious correlation with treatment modalities was noted.

Hematology values were within the normal range with exception of one pig in group 1 which showed abnormal hematology values (hemoglobin concentration 2.5 mmol/l, hematocrit 12%, thrombocyte count 18×10$^9$/L, leukocyte count 8.8×10$^9$/L at the end of the 50-minute instillation period). However, at T=24 h almost all hematologic values of this animal were within the normal range, except for the thrombocyte count ($53\times10^9$/L), which was within the normal range one week post-instillation.

Post-treatment urinalysis (50 minutes after beginning of instillation) showed high amounts of imiquimod (Table 14) for all treatment groups, except for the vehicle control group. The amount of imiquimod collected in the urine of animals in group 1 was almost 2-fold higher than that of animals in group 2 and 3, with no major difference between group 2 and 3. After 24 hours imiquimod levels were very low (<5 µg/mL).

TABLE 14

Per treatment group, the administered and measured end-treatment amount of Imiquimod

| Group | Administered total amount Imiquimod (µg) | End treatment total amount Imiquimod (µg, range, %) |
| --- | --- | --- |
| 1 | 268950 | 218860 (23440-320400) (81.4) |
| 2 | 257500 | 132735 (64350-176040) (51.5) |
| 3 | 247850 | 121636 (46260-219075) (49.1) |

Pharmacokinetic analyses revealed only little systemic absorption (table 15 and FIG. 18). Maximum plasma levels of animals in group 1 were threefold higher than maximum plasma levels of group 2 and 3 animals resulting in a twofold AUC. After eight hours almost no imiquimod (<2.10 ng/mL) could be detected in any pig plasma anymore.

TABLE 15

Pharamcokinetic plasma parameters of Imiquimod, per treatment group (mean ± sd)

| Group | $C_{max}$ (ng/mL) | AUC (ng*h/mL) | $T_{1/2}$ (h) |
| --- | --- | --- | --- |
| 1 | 45.17 ± 29.96 | 96.75 ± 50.42 | 1.18 ± 0.12 |
| 2 | 16.23 ± 10.22 | 45.67 ± 26.53 | 1.58 ± 1.05 |
| 3 | 17.00 ± 6.57 | 56.65 ± 24.94 | 1.90 ± 1.06 |

$C_{max}$ = Maximiun concentration; AUC = Area under the Curve; $T_{1/2}$ = half-life IL-6 cytokine levels were similar in all groups, including the vehicle control group, with maximum IL-6 levels reached eight hours after installation of the study drugs (data not shown).

Macroscopic examination of the resected bladders showed no abnormalities, except some areas with a hemorrhagic appearance in the pigs sacrificed 24 hours post-instillation of imiquimod (group 1-3), which was less apparent or absent in the pigs sacrificed after seven days.

Microscopic examination of the resected bladders revealed no difference between the four sampled regions (left lateral wall, right lateral wall, dome, trigone). In most animals of the three treatment groups a moderate, predominantly lymphocytic submucosal inflammatory reaction was seen 24 hours after intravesical instillation (FIG. 20), which decreased to mild inflammation in the pigs sacrificed after seven days. Twenty-four hours post-instillation vasculitis was observed in three pigs, equally divided over the three treatment arms (FIG. 21). Moderate myositis was observed in one pig in group 1. Mild reactive atypical bladder epithelium was observed in almost all animals sacrificed after 24 hours which disappeared in time and was not visible in the animals sacrificed after one week anymore. Erosion, submucosal edema and bleeding were mild, no allergic reaction was observed.

10.4. Discussion

As already stated in the description, imiquimod, a lead member of the imidazoquinolin(amines) family, has shown efficacy against many tumour types (Schön M P, Schön M. Imiquimod: mode of action. Br J Dermatol 2007; 157:8-13). The compound binds to TLR-7, inducting the production and secretion of pro-inflammatory cytokines, which consecutively induce a profound tumour specific cell mediated immune response, which is quite similar to the proposed working mechanism of BCG. In addition, imiquimod can exert direct apoptotic effects on tumour cells, can stimulate TLR-independent gene expression, and can interfere with adenosine receptor signaling pathways (Schön M P, Schön M. Imiquimod: mode of action. Br J Dermatol 2007; 157:8-13).

Imiquimod is effective and well tolerated as a topical agent for the treatment of various benign and malignant dermatological lesions. Local skin reactions are the most common side effects (Geisse J, Caro I, Lindholm J, Golitz L, Stampone P, Owens M. Imiquimod 5% cream for the treatment of superficial basal cell carcinoma: Results from two phase III, randomized, vehicle-controlled studies. J Am Acad Dermatol 2004; 50:722-33). Imiquimod has also been studied as systemic treatment modality: weekly administration of high dose oral imiquimod was studied in a phase I trial in cancer patients (Witt P L, Ritch P S, Reding D, McAuliffe T L, Westrick L, Grossberg S E, Borden E C. Phase I trial of an oral immunomodulator and interferon inducer in cancer patients. Cancer Res 1993; 53:5176-5180). Dose-limiting side effects were influenza-like symptoms and mild lymphocytopenia.

Bladder cancer might be an interesting target for imiquimod treatment: Intravesical administration of imiquimod resembles the topical treatment of skin lesions with direct contact with malignant cells and direct cytotoxicity or apoptosis induced by imiquimod independent of an immune response. Moreover, intravesical instillation avoids losses from first pass metabolism and allows the therapeutic effect of a drug to be localized at the desirable site with minimal systemic side effects.

Experimental evidence that imidazoquinoline(amines) may indeed be appropriate treatment modalities for bladder cancer was provided by Smith et al. These investigators showed that TLR-7 is expressed in murine and human bladder cancer cell lines and that imidazoquinoline has direct biological effects on these cell lines: cell viability was decreased and apoptosis and cytokine production was induced. In addition, initial results in an immune competent, orthotopic mouse model suggested antitumour effects in vivo (Smith E B, Schwartz M, Kawamoto H, et al. Antitumour effects of Imidazoquinolines in urothelial cell carcinoma of the bladder. J Urol 2007; 177:2347; Liu H, Schwartz M J, Hwang D H, Scherr O S. Tumour growth inhibition by an imidazoquinoline is associated with c-Myc down-regulation in urothelial cell carcinoma. BJU Int 2008; 101:894-901)

To investigate whether the target of imiquimod, TLR-7, is expressed in human bladder cancer TLR-7 expression in 15 specimens was evaluated. Positive staining was demonstrated in all samples with an average of 90%, however there was some heterogeneity in intensity leading to H-scores ranging from 90 to 165. These results demonstrate that bladder cancer may be an attractive target for imiquimod therapy.

To evaluate pharmacokinetics and possible toxicity of imiquimod installations, experiments in pigs were performed. TLR-7 expression in porcine and human bladder tissue samples was similar, corroborating the validity of the pig model. Three different intravesical solutions of imiquimod and a vehicle control (lactic acid solution) were studied. None of the tested formulations affected the pig's general well-being as judged by e.g., mucosal appearance, behaviour, food/water intake, etc. Plasma analysis showed only little systemic absorption of imiquimod after bladder instillation, regardless of the formulation used. In accordance, high amounts of imiquimod were recovered in post-instillation urine. However, the post-treatment urine imiquimod levels in animals treated with imiquimod in a simple lactic acid solution (group 1) were almost 2-fold higher than in animals treated with imiquimod formulations with poloxamer and HPβCD (group 2 and 3). Moreover, the mean maximum plasma level of imiquimod in group 1 was 3-fold higher than in group 2 and 3 animals. This difference is likely the result of the increased and prolonged bio-adhesiveness of the drug formulations with poloxamer and HPβCD to the bladder wall. However, this effect was short lived, since after eight hours almost no imiquimod could be detected in the pig plasma anymore and after 24 hours almost no imiquimod could be detected in the urine anymore in any of the animals, regardless of imiquimod formulation. It is possible that drug formulations 2 and 3 lead to longer, sustained membrane levels of imiquimod.

Plasma IL-6 levels were similar in all groups, including the vehicle control group, with maximum values being reached eight hours after bladder instillations, most likely due to the stress reaction after general anesthesia and bladder catheterization, rather than immunostimulation by imiquimod. Moreover, plasma imiquimod levels were too low to achieve a systemic cytokine response.

Histopathological examination of the bladder wall revealed the intended inflammatory reaction in the imiquimod treated groups. Apart from this intended inflammatory reaction no significant abnormalities were observed. Only the vasculitis may represent some toxic reaction, albeit transient: no vasculitis was observed in the animals sacrificed on day 7. It is not possible to make meaningful intergroup comparisons with these small numbers per group, however, no major difference between the tested imiquimod solutions was observed.

In conclusion, intravesically administered imiquimod in pigs is well tolerated, causes no bladder wall toxicity and formulations with poloxamer and HPβCD stay longer in the bladder with less systemic absorption. The safety profile of intravesical imiquimod compares favorable to that of current therapies such as BCG. Considering the very similar pharmacokinetic characteristics a phase I dose escalation marker lesion study will be initiated with imiquimod 0.5% in 0.1 M lactic acid, poloxamer 407 16% and HPβCD 5% in patients with NMIBC.

11. Example

Optimization of Intravesical Formulation of a Toll-Like Receptor 7 Agonist for Bladder Cancer Therapy 11.1. Introduction The objective of this study was to optimize the formulation of imiquimod to improve therapeutic application. The systemic and local inflammation induced by various formulations of imiquimod was compared. The anticancer efficacy of imiquimod in thermosensitive poloxamer polymer was evaluated in murine orthotopic bladder cancer models.

11.2. Material and Methods 11.2.1. Mice 6- to 8-week old female C57BL/6 mice were purchased from Charles River Laboratory (Wilmington, Mass.). TLR7 deficient mice were a gift from S. Akira (Osaka University, Osaka, Japan) and backcrossed for 10 generations onto the C57BL/6 background mice. All mice were housed under standard conditions in the University of California, San Diego Animal Facility. All procedures and protocols received prior approval by the institutional review board of UCSD.

11.2.2. Reagents

Imiquimod (TMX, TMX-101, R-837) and Lutrol®F127 were provided by Telormedix SA (Bioggio, Switzerland). Lactic acid was purchased from Fisher Scientific (Pittsburgh, Pa.). 2-(hydroxypropyl)-β-cyclodextrin (HPβCD) was purchased from Sigma Aldrich (St. Louis, Mo.). Imiquimod was solved at the final concentration of 1% (w/v, 41.7 mM) in 0.1% lactic acid (lactic acid formulation). Lutrol®F127 (poloxamer 407) was added to 0.1M lactic acid to make 20% (poloxamer formulation). 5% HPβCD was incorporated into 16% Lutrol®F127, in 0.1M lactic acid (poloxamer-HPβCD formulation). All solutions were filtered by 0.22 micron filter before administration.

11.2.3. In Vivo Pharmacological Study

Mice were anesthetized and catheterized using a 20G Teflon intravenous catheter (Terumo Co. Somerset, N.J.). 150, 500, or 1500 nmoles imiquimod in 50 or 100 μL vehicles were intravesically administered, respectively. 120 μL volume was used for installation of 5000 nmoles. The imiquimod solution was kept in the bladder for 20 min. The levels of cytokines were measured by Luminex microbead assay (Invitrogen, Carlsbad, Calif.) according to the manufacture's instruction. The minimum detection levels of TNFα, and KC were 5 pg/mL, and 25 pg/mL, respectively. The level of imiquimod in serum was analyzed by Chiman SRL (Rottofreno, Italy).

11.2.4. Histological Examination

Mice were administered 100 μL 0.1% imiquimod in poloxamer-HPβCD formulation once, or 50 μL three times at four-day intervals. 24 hours after the last administration, the bladders were collected. The fixed bladders were paraffin-embedded and were stained with hematoxylin and eosin (H&E) by UCSD Cancer Center Histology Core.

11.2.5. Implantation, Treatment and Assessment of Tumor

After 20 min-treatment with poly-L-lysine (0.1 mg/mL), $1 \times 10^6$ MB49 cells were implanted as described previously (Hegele A, Dalpke A, Barth P et al. Antineoplastic effect of immunostimulatory DNA (CpG-ODN) in a murine C57-BL6/MB-49 transitional cell carcinoma model. *Anticancer research*. 2004; 24: 2225-30). The treatment was performed on day 3, 6 and 9. MB49 implanted-mice with no treatment or vehicle treatment served as controls. Mice were sacrificed on day 11 and weight of bladder was measured.

11.2.6. Statistical Analysis

A software package (Prism 4.0, GraphPad, San Diego Calif.) was used for statistical analyses as indicated in the figure legends. A value of $p<0.05$ was considered statistically significant.

11.3. Results 11.3.1. Intravesical Administration of Imiquimod Induced Systemic Inflammation Imiquimod is known to be insoluble in water and sparingly soluble in common pharmaceutical solvents. As shown above acetic and/or lactic acid solution increases the solubility of imiquimod. Therefore, 0.1M lactic acid was used to prepare 1% imiquimod solution (~41.7 mM). Mice intravesically received 150, 500, 1500 and 5000 nmoles. Serum TNFα and KC were induced in a dose-dependent manner (0.1M lactic acid in FIGS. 22A and B). The levels of these factors in the bladder were 10 to 100 times lower than the levels in their serum ($p<0.001$ at 1500 and 5000 nmoles, FIGS. 22C and D).

11.3.2. Addition of Poloxamer Polymer Prevented Absorption of Imiquimod and Systemic Induction of Cytokines Systemic induction of proinflammatory cytokines causes anorexia and fatigue, so called "sickness syndrome" in hosts (Hayashi T, Cottam H B, Chan M et al. Mast cell-dependent anorexia and hypothermia induced by mucosal activation of Toll-like receptor 7. *Am J Physiol RegulIntegr Comp Physiol.* 2008; 295: R123-32). To avoid systemic absorption as well as increase the local contact of imiquimod to the urothelium, thermosensitive poloxamer polymer, Lutrol®F127, was added to the formulation. The levels of TNFα (FIGS. 23A and B) and KC (FIGS. 23C and D) in both serum and bladder were significantly reduced in mice that received 5000 nmoles of imiquimod in this formulation compared to the formulation with lactic acid.

To evaluate effect of the poloxamer polymer on the systemic absorption of imiquimod via bladder urothelium, the sera from mice that received 1500 nmoles imiquimod were collected at 2, 4, 6, 24 and 48 hours. In mice receiving imiquimod either in lactic acid alone or in poloxamer formulation, maximum serum concentration of imiquimod was observed 2 hours after administration (FIG. 23E) ($p<0.01$). The levels of serum imiquimod increased in a dose-dependent manner (FIG. 23F). Addition of poloxamer polymer in the formulation reduced the serum levels of imiquimod at 2 hour time points ($p<0.01$, FIG. 23E) and at 5000 nmoles ($p<0.01$, FIG. 23F). These data indicate that inclusion of poloxamer in the formulation significantly reduce systemic absorption of imiquimod.

11.3.3. Incorporation of HPβCD Restores Systemic and Local Inflammation

To improve the physical stability and achieve a clear homogeneous solution and achieve the complete release from the poloxamer polymer, imiquimod was incorporated with HPβCD to poloxamer in lactic acid (poloxamer-HPβCD formulation). The systemic levels of TNFα and KC were evaluated and compared to the other formulations (FIG. 24). Adding the poloxamer polymer reduced the serum KC levels to almost baseline levels, compared to lactic acid formulation ($p<0.001$, FIGS. 24A and 24B). Addition of HPβCD to the poloxamer formulation significantly restored the serum KC level (FIG. 24B), but not TNFα (FIG. 24A). A similar trend was seen in local levels of KC (FIG. 24C).

11.3.4. Evaluation of Local Inflammation in the Bladder by Intravesical Administration of Imiquimod in Poloxamer-HPβCD Formulation To evaluate the local inflammation in the bladder, mice received intravesically 0.1% imiquimod in poloxamer-HPβCD formulation as vehicle. Influx of inflammatory cells in the bladder was evaluated by histological examination (FIG. 25). Because patients received repeated intravesical treatments in the clinical application, we tested the effect of repeated administration of imiquimod in poloxamer-HPβCD formulation on days 0, 4, and 8. After the first instillation of imiquimod, the cell infiltration was initiated (FIG. 25C) compared to the vehicle alone (FIG. 25A). After the third treatment, substantial infiltration of mononuclear cells in the lamina propria in the bladder treated with imiquimod was observed (FIG. 25D), while few cells infiltrated in the vehicle- or saline-treated bladders (FIGS. 25B and E). Reduced cell infiltration was observed in the bladder of TLR7 deficient mice treated with imiquimod in poloxamer-HPβCD formulation similar to saline-treated mice, indicating that inflammation induced by imiquimod in the bladder was TLR7 dependent (FIG. 25F).

11.3.5. Evaluation of the Therapeutic Efficacy in Mouse Orthotopic Bladder Cancer Models Orthotopic bladder tumor models were generated using MB49, a cell line derived from transitional cell carcinoma of the murine urinary tracts. The mice bearing the MB49 bladder tumor were treated three times (days 3, 6 and 9) with 50 µL of 0.1% imiquimod in poloxamer-HP CD formulation as vehicle. The treatment group showed significantly lower average tumor loads compared to the non-treated or vehicle treated group ($p<0.01$, FIG. 26). Thus, treatment with imiquimod in poloxamer-HP CD formulation maintained the bladder weight nearly to that of non-tumor bearing (naïve) mice.

11.4. Discussion

In this study, thermosensitive poloxamer polymer was used to ensure prolonged local contact and minimize systemic absorption of imiquimod. Polymer formulation reduced systemic absorption of imiquimod from bladder urothelium with sustained local infiltration of immune cells. Incorporating HP CD in the formulation improved the physical stability, achieving a clear homogeneous solution. This formulation improved the induction of local chemokine and demonstrated anti-tumor effects in an orthotopic mouse model of bladder cancer.

Intravesical BCG administration is a well established immune therapy of superficial bladder cancer (Alexandroff A B, Jackson A M, O'Donnell M A, James K. BCG immunotherapy of bladder cancer: 20 years on. *Lancet.* 1999; 353: 1689-94). Although live BCG bacilli provides a significant advantage to evoke the immune response, use of live BCG requires careful biohazard precaution for the health care staff and patients (Games J. Nursing implications in the management of superficial bladder cancer. *Seminars in urologic oncology.* 1996; 14: 36-40). BCG remains only partially effective and serious side effects may occur, including high fever, pneumonia, hepatitis and sepsis. Efforts continue to develop safer and more effective therapy for bladder cancer. Among those, attempts to use the individual TLR agonist to treat the bladder cancer have been reported (Smith E B, Schwartz M, Kawamoto H et al. Antitumor effects of imidazoquinolines in urothelial cell carcinoma of the bladder. *The Journal of urology.* 2007; 177: 347-51; Mangsbo S M, Ninalga C, Essand M, Loskog A, Totterman T H. CpG therapy is superior to BCG in an orthotopic bladder cancer model and generates CD4+ T-cell immunity. *J Immunother.* 2008; 31: 34-42.) Repeated application of TLR9 agonist improved survival and reduced tumor loads (Mangsbo S M, Ninalga C, Essand M, Loskog A, Totterman T H. CpG therapy is superior to BCG in an orthotopic bladder cancer model and generates CD4+ T-cell immunity. *J Immunother* 2008; 31: 34-42). TLR7 agonist imiquimod directly affects human and mouse bladder cancer cells to induce chemokinesecretion, and to induce apoptosis and reduce tumor growth (Smith E B, Schwartz M, Kawamoto H et al. Antitumor effects of imidazoquinolines in urothelial cell carcinoma of the bladder. *The Journal of urology.* 2007; 177: 2347-51).

In this study it was demonstrated that imiquimod in poloxamer-HP CD formulation could initiate a substantial local innate immune reaction. Because acid formulation increased solubility of imiquimod, imiquimod was initially tested dissolved in 0.1 M lactic acid that is commonly used in the pharmaceutical industry. Imiquimod in lactic acid formulation was absorbed systemically and caused the significant induction of systemic inflammation. Live BCG bacilli adhere to surface of the bladder wall (Atkins H, Davies B R, Kirby J A, Kelly J D. Polarisation of a T-helper cell immune response by activation of dendritic cells with CpG-containing oligonucleotides: a potential therapeutic regime for bladder cancer immunotherapy. *British journal of cancer.* 2003; 89: 2312-9; Akazawa T, Masuda H, Saeki Y et al. Adjuvant-mediated tumor regression and tumor-specific cytotoxic response are impaired in MyD88-deficient mice. *Cancer research.* 2004; 64: 757-64) and provide sustained immune stimulation to urothelium and local immune cells for prolonged periods. Thermosensitive poloxamer polymer reduces the drug release and holds the drug concentration on the surface of the cells and prevents the systemic absorption of the drug (Anderson B C, Pandit N K, Mallapragada S K. Understanding drug release from poly(ethylene oxide)-b-poly(propylene oxide)-b-poly(ethylene oxide) gels. *J Control Release.* 2001; 70: 157-67). To recapitulate the advantageous pro-inflammatory properties of live BCG bacilli infection and to reduce the systemic absorption as well as to increase the surface contact of drug, thermosensitive poloxamer polymer was added to lactic acid formulation. The poloxamer formulation significantly reduced the systemic absorption of imiquimod through the bladder surface and reduced the systemic cytokine induction to baseline levels. The component of this study that was of particular interest was that the formulation including HPβCD restored the induction of KC by imiquimod compared to that of poloxamer alone. Complexation using HPβCD is a common approach for increasing drug solubility and stability in aqueous media (Brewster M E, Loftsson T. Cyclodextrins as pharmaceutical solubilizers. *Advanced drug delivery reviews.* 2007; 59: 645-66. [25] Bilensoy E, Rouf M A, Vural I, Sen M, Hincal A A. Mucoadhesive, thermosensitive, prolonged-release vaginal gel for clotrimazole:beta-cyclodextrin complex. *AAPS PharmSciTech.* 2006; 7: E38). Moreover, inclusion of HPbCD in polymers is used in vaginal delivery systems (Chang J Y, Oh Y K, Kong H S et al. Prolonged antifungal effects of clotrimazole containing mucoadhesive thermosensitive gels on vaginitis. J Control Release. 2002; 82: 39-50.) Since 20% thermosensitive poloxamer was observed to solidify in the bladder within a short time, causing the obstruction of urethra, the concentration of poloxamer was reduced to 16%. Specifically, incorporating HPβCD in the polymer formulation improved the aqueous solubility and imiquimod was effective in anti-tumor effects in an orthoptropic mouse model of bladder cancer. This finding strongly supports use of the poloxamer-HPbCD formulation for subsequent clinical studies.

Effective anti-tumor immune therapy requires an appropriate recruitment of immune cells Simons M P, O'Donnell M A, Griffith T S. Role of neutrophils in BCG immunotherapy for bladder cancer. *Urologic oncology.* 2008; 26: 341-5; Saban M R, Simpson C, Davis C et al. Discriminators of mouse bladder response to intravesical Bacillus Calmette-Guerin (BCG). *BMC immunology.* 2007; 8: 6). Histological examination shows substantial immune cell infiltration into the lamina propria by imiquimod. The cell infiltration in the bladder induced by imiquimod diminished in TLR7-deficient mice, indicating the inflammation was TLR7 dependent, not caused by vehicle or mechanical injury. The integrity of urothelium was well maintained after repeated administration of vehicle alone (poloxamer-HPβCD formulation). It was reported that 1V270, a phospholipid conjugate of a TLR7 agonist, exerts excellent and rapid Th1 adaptive immune responses 12. Because immune therapy by live BCG installation leads to a Th1 type adaptive immune activation that is tumor specific (Luo Y, Chen X, O'Donell M A. Role of Th1 and Th2 cytokines in BCG-induced IFN-gamma production: cytokine promotion and simulation of BCG effect. *Cytokine.* 2003; 21: 17-26), the phospholipid conjugate has potential to enhance the therapeutic potency of the unconjugated TLR7 agonist on bladder cancer.

In summary, these results suggest the formulation of poloxamer and HPβCD of drugs with low solubility may exert favorable properties, such as slow release profile and longer surface contact, while avoiding possible systemic adverse effects. Optimized poloxamer-HP CD formulations may increase the maximum tolerated dose of imiquimod and improve patient compliance.

The invention claimed is:

1. A pharmaceutical composition comprising imiquimod, lactic acid, a polymer and cyclodextrin, wherein the polymer consists of Poloxamer 407 in an amount of 11% (w/v) to 18% (w/v), and the composition is for bladder instillation.

2. The pharmaceutical composition of claim 1, wherein the lactic acid is at a concentration of about 0.025 M to about 0.200 M.

3. The pharmaceutical composition of claim 2, wherein the lactic acid is at a concentration of about 0.075 M to about 0.125 M.

4. The pharmaceutical composition of claim 1, wherein the imiquimod is in an amount of about 0.005% (w/v) to about 5% (w/v).

5. The pharmaceutical composition of claim 4, wherein the imiquimod is in an amount of about 0.1% (w/v) to about 1% (w/v).

6. The pharmaceutical composition of claim 1, wherein the cyclodextrin is selected from α-cyclodextrins, β-cyclodextrins, γ-cyclodextrins, δ-cyclodextrins, ε-cyclodextrins, and hydroxypropyl-β-cyclodextrin (HP-β-CD).

7. The pharmaceutical composition of claim 6, wherein the cyclodextrin is hydroxypropyl-β-cyclodextrin (HP-β-CD).

8. The pharmaceutical composition of claim 1, wherein the cyclodextrin in an amount of about 0.1% (w/v) to about 30% (w/v).

9. The pharmaceutical composition of claim 8, wherein the cyclodextrin in an amount of about 2% (w/v) to about 6% (w/v).

10. The pharmaceutical composition of claim 1, wherein the Poloxamer 407 is in an amount of 11% (w/v) to 17% (w/v).

11. The pharmaceutical composition of claim 10, wherein the Poloxamer 407 is in an amount of 11% (w/v) to 16% (w/v).

12. The pharmaceutical composition of claim 1, wherein the composition is aqueous.

13. A pharmaceutical composition comprising imiquimod in an amount of about 0.1% (w/v) to about 1% (w/v), lactic acid in a concentration of about 0.075 M to about 0.125 M, cyclodextrin in an amount of about 2% (w/v) to about 6% (w/v), and a polymer consisting of Poloxamer 407 in an amount of 11% (w/v) to 18% (w/v), and the composition is aqueous and is for bladder instillation.

* * * * *